(12) United States Patent
Loftis et al.

(10) Patent No.: US 11,571,244 B2
(45) Date of Patent: Feb. 7, 2023

(54) POSTERIOR SPINAL FIXATION SCREWS

(71) Applicant: NuVasive, Inc., San Diego, CA (US)

(72) Inventors: Chad M. Loftis, San Diego, CA (US); Matthew Tobias Jacobs, San Diego, CA (US); Robert German, San Diego, CA (US); Enrique Rayon, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 16/880,760

(22) Filed: May 21, 2020

(65) Prior Publication Data

US 2020/0367940 A1 Nov. 26, 2020

Related U.S. Application Data

(60) Provisional application No. 62/851,100, filed on May 22, 2019.

(51) Int. Cl.
| | | |
|---|---|---|
| *A61B 17/70* | (2006.01) | |
| *A61B 17/86* | (2006.01) | |
| *A61B 34/00* | (2016.01) | |
| *A61B 17/68* | (2006.01) | |

(52) U.S. Cl.
CPC ........ *A61B 17/7037* (2013.01); *A61B 17/701* (2013.01); *A61B 17/7011* (2013.01); *A61B 17/7032* (2013.01); *A61B 17/7034* (2013.01); *A61B 17/7041* (2013.01); *A61B 17/7043* (2013.01); *A61B 17/8605* (2013.01); *A61B 34/76* (2016.02); *A61B 2017/681* (2013.01)

(58) Field of Classification Search
CPC . A61B 17/70; A61B 17/7001; A61B 17/7002; A61B 17/701; A61B 17/7032–7038; A61B 17/7041; A61B 17/7043; A61B 17/7049–7052
See application file for complete search history.

(56) References Cited

U.S. PATENT DOCUMENTS

| | | |
|---|---|---|
| 6,726,689 B2 | 4/2004 | Jackson |
| 6,736,820 B2 | 5/2004 | Biedermann |
| 7,785,354 B2 | 8/2010 | Biedermann |
| 7,803,174 B2 | 9/2010 | Denis et al. |
| 7,942,902 B2 | 5/2011 | Schwab |
| 7,942,907 B2 | 5/2011 | Richelsoph |
| 7,955,359 B2 | 6/2011 | Matthis |
| 8,034,085 B2 | 10/2011 | Slivka et al. |
| 8,197,517 B1 | 6/2012 | Lab et al. |
| 8,221,472 B2 | 7/2012 | Peterson et al. |
| 8,236,028 B2 | 8/2012 | Kalfas et al. |
| 8,298,269 B2 | 10/2012 | Null et al. |
| 8,337,527 B2 | 12/2012 | Hawkins et al. |
| 8,343,191 B2 | 1/2013 | Matthis |
| 8,353,932 B2 | 1/2013 | Jackson |
| 8,409,260 B2 | 4/2013 | Biedermann |
| 8,506,610 B2 | 8/2013 | Biedermann et al. |
| 8,657,857 B2 | 2/2014 | Dall et al. |
| 8,690,925 B2 | 4/2014 | Biedermann |
| 8,696,711 B2 | 4/2014 | Jackson |

(Continued)

*Primary Examiner* — Eduardo C Robert
*Assistant Examiner* — Michelle C Eckman
(74) *Attorney, Agent, or Firm* — Hoffman Warnick, LLC

(57) ABSTRACT

The present disclosure includes bone screws and assemblies thereof for surgical procedures of the spine including but not limited to posterior spinal fixation procedures.

20 Claims, 39 Drawing Sheets

(56) References Cited

U.S. PATENT DOCUMENTS

| | | | |
|---|---|---|---|
| 8,764,805 B2 | 7/2014 | Biedermann et al. | |
| 8,795,336 B2 | 8/2014 | Biedermann et al. | |
| 8,828,060 B2 | 9/2014 | Biedermann | |
| 8,864,803 B2 | 10/2014 | Biedermann | |
| 8,870,927 B2 | 10/2014 | Matthis | |
| 8,945,194 B2 | 2/2015 | Biedermann | |
| 8,986,349 B1 | 3/2015 | German et al. | |
| 8,998,959 B2 | 4/2015 | Jackson et al. | |
| 8,998,961 B1 | 4/2015 | Ziemek et al. | |
| 9,005,259 B2 | 4/2015 | Biedermann et al. | |
| 9,066,759 B2 | 6/2015 | Biedermann et al. | |
| 9,084,634 B1 | 7/2015 | Lab et al. | |
| 9,101,405 B2 | 8/2015 | Dickinson et al. | |
| 9,144,437 B2 | 9/2015 | Matthis | |
| 9,168,069 B2 | 10/2015 | Jackson et al. | |
| 9,173,684 B2 | 11/2015 | Biedermann et al. | |
| 9,241,739 B2 | 1/2016 | Mueller et al. | |
| 9,271,760 B2 | 3/2016 | Biedermann | |
| 9,277,941 B2 | 3/2016 | Biedermann et al. | |
| 9,277,942 B2 | 3/2016 | Biedermann | |
| 9,289,246 B2 | 3/2016 | Biedermann et al. | |
| 9,333,010 B2 | 5/2016 | Matthis | |
| 9,333,011 B2 | 5/2016 | Biedermann | |
| 9,333,017 B2 | 5/2016 | Biedermann et al. | |
| 9,339,302 B2 | 5/2016 | Biedermann | |
| 9,351,766 B2 | 5/2016 | Biedermann et al. | |
| 9,445,847 B2 | 9/2016 | Biedermann | |
| 9,480,517 B2 | 11/2016 | Jackson et al. | |
| 9,486,246 B2 | 11/2016 | Biedermann et al. | |
| 9,492,205 B2 | 11/2016 | Alsup et al. | |
| 9,498,256 B2 | 11/2016 | Biedermann | |
| 9,522,021 B2 | 12/2016 | Jackson et al. | |
| 9,566,093 B2 | 2/2017 | Biedermann | |
| 9,585,698 B2 | 3/2017 | Biedermann | |
| 9,603,635 B2 | 3/2017 | Leff et al. | |
| 9,615,867 B2 | 4/2017 | Picetti et al. | |
| 9,655,652 B2 | 5/2017 | Biedermann | |
| 9,675,384 B2 | 6/2017 | Gaines et al. | |
| 9,681,894 B2 | 6/2017 | Nichols et al. | |
| 9,717,534 B2 | 8/2017 | Jackson et al. | |
| 9,730,735 B2 | 8/2017 | Mishra et al. | |
| 9,788,866 B2 | 10/2017 | Jackson | |
| 9,820,780 B2 | 11/2017 | Duncan et al. | |
| 9,833,263 B2 | 12/2017 | Chandanson et al. | |
| 9,883,892 B2 | 2/2018 | Jackson et al. | |
| 9,895,173 B2 | 2/2018 | Biedermann | |
| 9,907,574 B2 | 3/2018 | Jackson et al. | |
| 9,924,974 B2 | 3/2018 | Biedermann | |
| 9,980,754 B2 | 5/2018 | Harper et al. | |
| 10,058,353 B2 | 8/2018 | Biedermann | |
| 10,064,659 B2 | 9/2018 | Biedermann | |
| 10,105,163 B2 | 10/2018 | Keyer et al. | |
| 10,130,395 B2 | 11/2018 | Leff et al. | |
| 10,179,010 B2 | 1/2019 | Jackson et al. | |
| 10,188,431 B2 | 1/2019 | Erbulut et al. | |
| 10,238,432 B2 | 3/2019 | Carruth et al. | |
| 10,251,678 B2 | 4/2019 | Alsup et al. | |
| 10,299,843 B2 | 5/2019 | Berry et al. | |
| 10,335,200 B2 | 7/2019 | Jackson | |
| 10,405,893 B2 | 9/2019 | Laeng et al. | |
| 10,463,402 B2 | 11/2019 | Biester et al. | |
| 10,463,412 B2 | 11/2019 | Picetti et al. | |
| 10,478,227 B2 | 11/2019 | Leff et al. | |
| 10,485,594 B2 | 11/2019 | Toon et al. | |
| 10,492,835 B2 | 12/2019 | Lee et al. | |
| 10,517,648 B2 | 12/2019 | Faulhaber | |
| 10,561,444 B2 | 2/2020 | Jackson | |
| 10,568,667 B2 | 2/2020 | Biester et al. | |
| 10,575,877 B2 | 3/2020 | Harper et al. | |
| 10,588,666 B2 | 3/2020 | Samuel et al. | |
| 10,603,077 B2 | 3/2020 | Zhang et al. | |
| 10,603,081 B2 | 3/2020 | Harper et al. | |
| 10,646,260 B2 | 5/2020 | Abbasi | |
| 10,702,310 B2 | 7/2020 | Leff et al. | |
| 10,709,478 B2 | 7/2020 | Nichols et al. | |
| 10,722,272 B2 | 7/2020 | Biedermann | |
| 10,722,273 B2 | 7/2020 | Jackson | |
| 10,736,665 B2 * | 8/2020 | Bobbitt | A61B 17/7049 |
| 10,786,285 B2 | 9/2020 | Stein et al. | |
| 10,869,695 B2 | 12/2020 | Carruth et al. | |
| 11,020,152 B2 | 6/2021 | Keyer et al. | |
| 2004/0111088 A1 * | 6/2004 | Picetti | A61B 17/7037 606/279 |
| 2005/0080415 A1 | 4/2005 | Keyer et al. | |
| 2005/0171537 A1 | 8/2005 | Mazel et al. | |
| 2007/0191844 A1 | 8/2007 | Carls et al. | |
| 2009/0036929 A1 | 2/2009 | Reglos et al. | |
| 2010/0168797 A1 | 7/2010 | Graf | |
| 2013/0165977 A1 | 6/2013 | Biedermann et al. | |
| 2013/0211456 A1 | 8/2013 | Dickinson et al. | |
| 2014/0121703 A1 | 5/2014 | Jackson et al. | |
| 2014/0277157 A1 | 9/2014 | Chandanson et al. | |
| 2014/0379031 A1 | 12/2014 | Biedermann et al. | |
| 2016/0361095 A1 | 12/2016 | Burdi et al. | |
| 2017/0086886 A1 | 3/2017 | Duncan et al. | |
| 2017/0348026 A1 * | 12/2017 | Stein | A61B 17/705 |
| 2018/0092679 A1 | 4/2018 | Toon et al. | |
| 2018/0228518 A1 * | 8/2018 | Carruth | A61B 17/866 |
| 2018/0243009 A1 * | 8/2018 | Bobbitt | A61B 17/7001 |
| 2018/0325558 A1 * | 11/2018 | Yacoub | A61B 17/7056 |
| 2019/0038320 A1 | 2/2019 | Biedermann | |
| 2019/0247094 A1 | 8/2019 | Yacoub et al. | |
| 2019/0298420 A1 | 10/2019 | Mishra et al. | |
| 2019/0374260 A1 | 12/2019 | Laeng et al. | |
| 2020/0038067 A1 | 2/2020 | Errico et al. | |
| 2020/0054376 A1 | 2/2020 | Toon et al. | |
| 2020/0060730 A1 | 2/2020 | Choe et al. | |
| 2020/0093516 A1 | 3/2020 | Faulhaber | |
| 2020/0138483 A1 | 5/2020 | Zatta | |
| 2020/0155202 A1 | 5/2020 | Jackson et al. | |
| 2020/0179009 A1 | 6/2020 | Zhang et al. | |
| 2020/0179015 A1 | 6/2020 | Samuel et al. | |
| 2020/0229848 A1 * | 7/2020 | Palagi | A61B 17/7014 |
| 2020/0289166 A1 | 9/2020 | Leff et al. | |
| 2020/0305933 A1 * | 10/2020 | Zhu | A61B 17/704 |
| 2020/0315666 A1 | 10/2020 | Nichols et al. | |
| 2020/0330133 A1 | 10/2020 | Bobbitt et al. | |
| 2020/0390475 A1 | 12/2020 | Stein et al. | |
| 2021/0022779 A1 | 1/2021 | Bobbit | |
| 2021/0068872 A1 | 3/2021 | Carruth et al. | |
| 2021/0137565 A1 | 5/2021 | Palagi | |
| 2021/0153904 A1 | 5/2021 | Armstrong et al. | |
| 2021/0153905 A1 | 5/2021 | Armstrong et al. | |
| 2021/0153906 A1 | 5/2021 | Armstrong et al. | |
| 2021/0153907 A1 | 5/2021 | Armstrong et al. | |
| 2021/0251663 A1 | 8/2021 | Keyer et al. | |

* cited by examiner 401
400

402

401
400

402

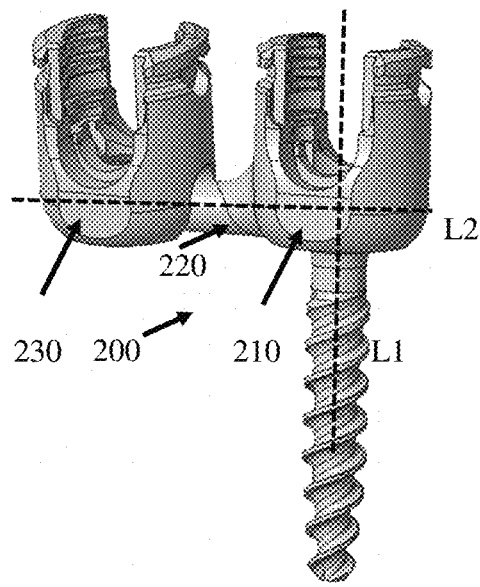
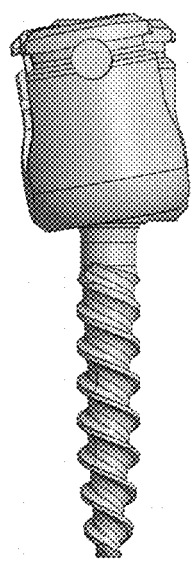
FIG. 19A
FIG. 19B
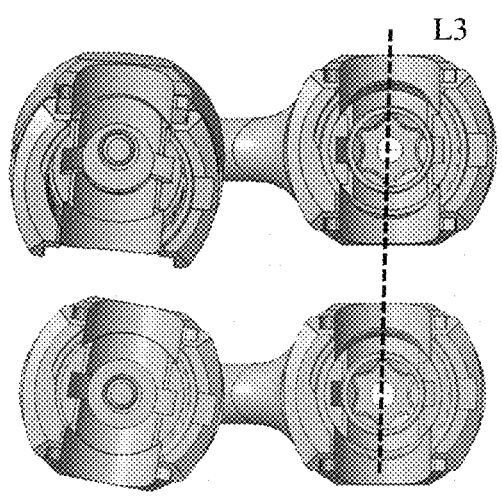
FIG. 19C
FIG. 19D

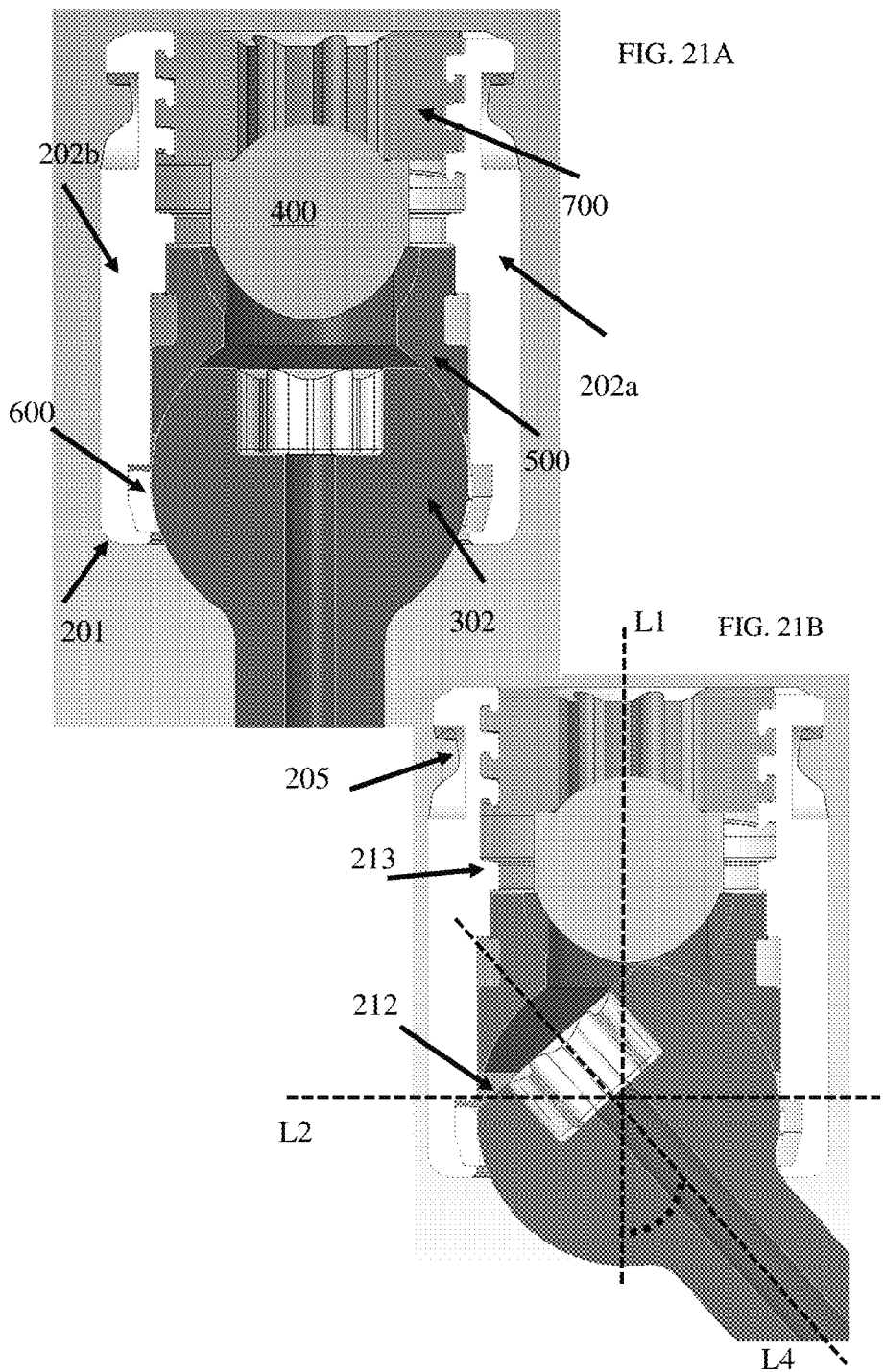

FIG. 22A
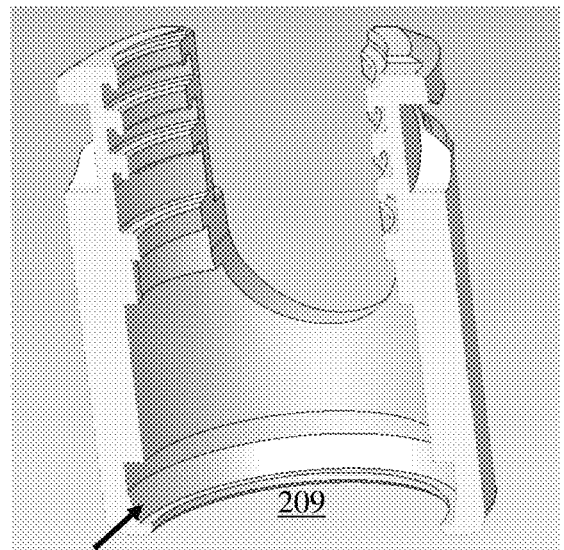
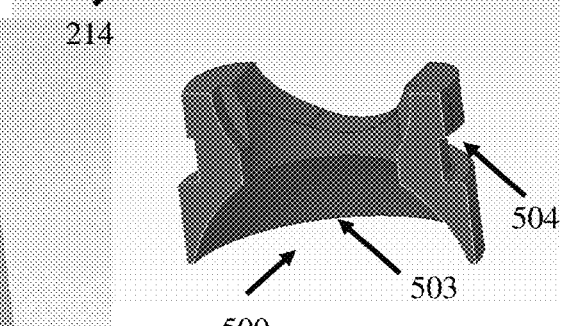
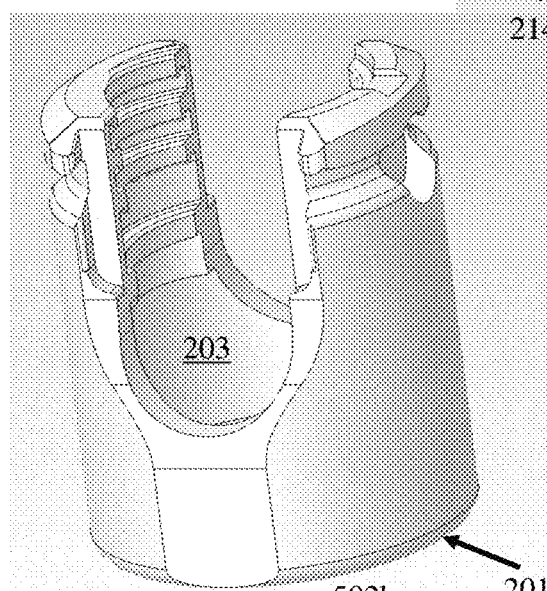
FIG. 22B
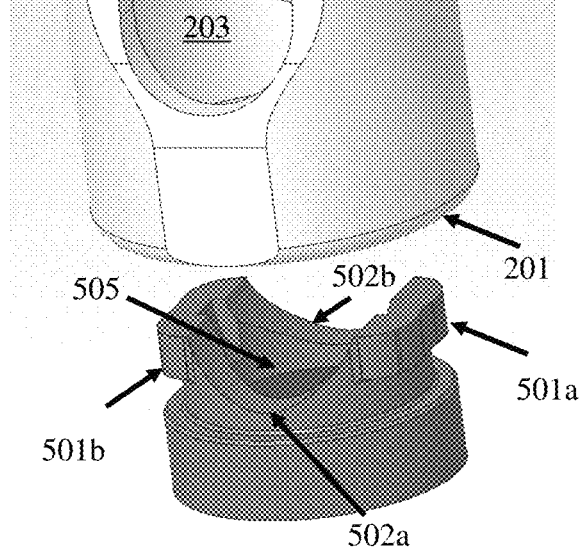

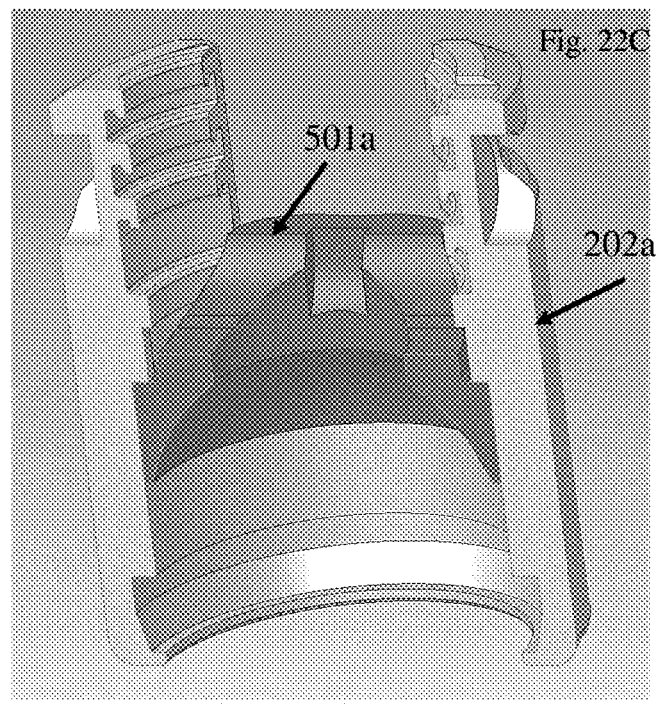
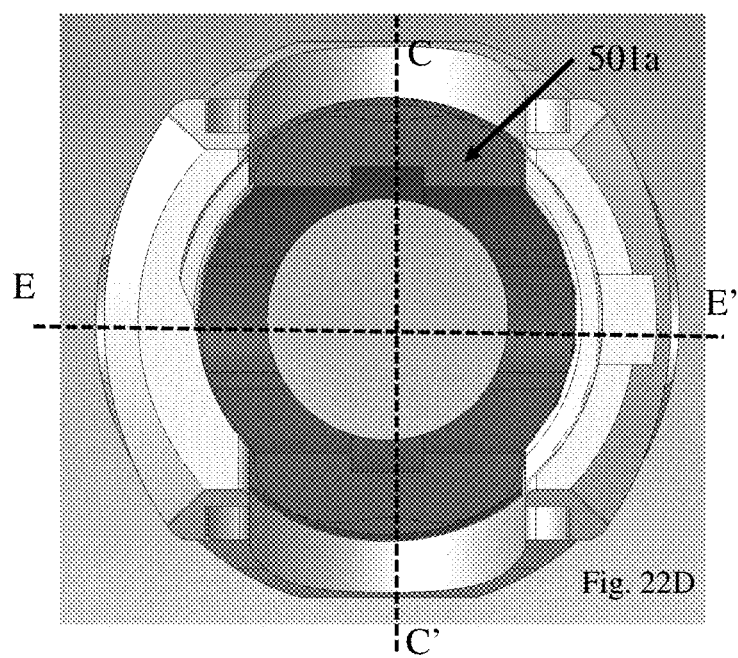

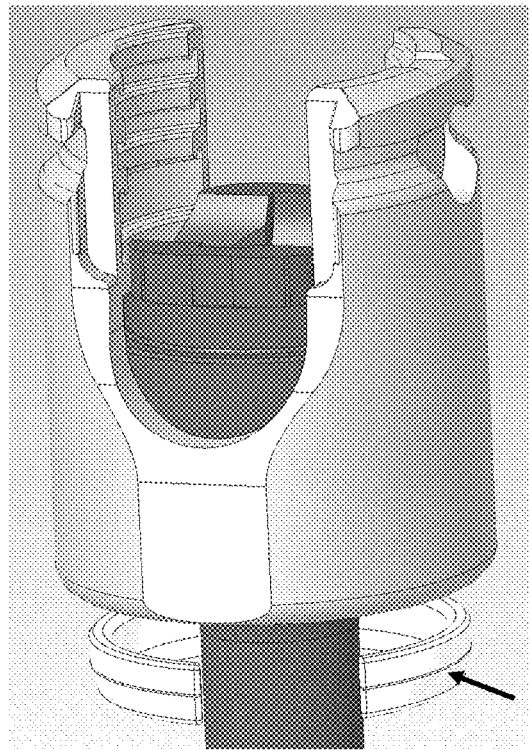
FIG. 22G
600
FIG. 22H
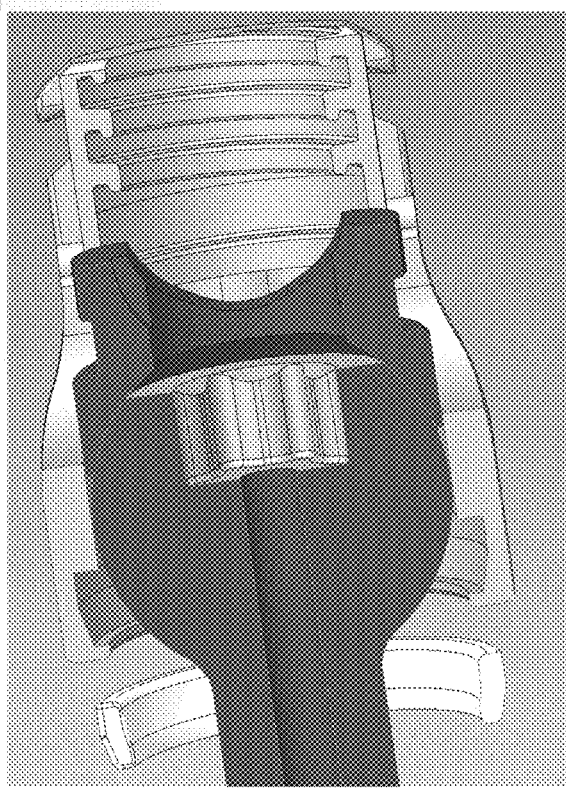

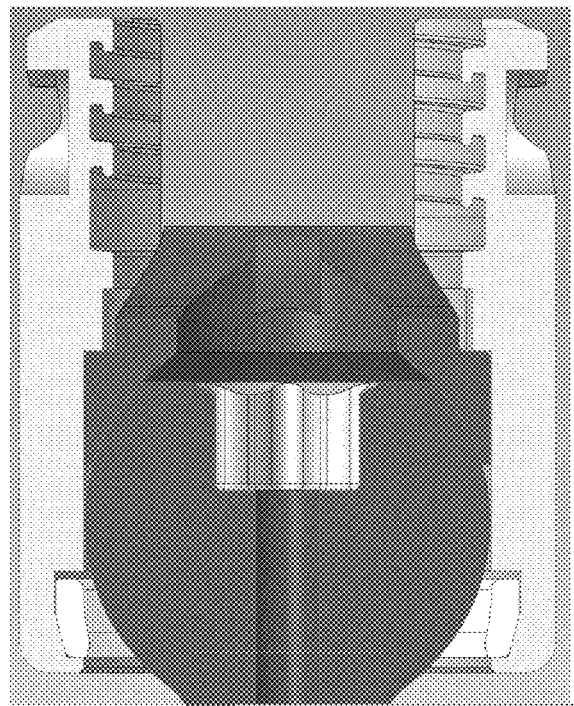
FIG. 22I
FIG. 23A
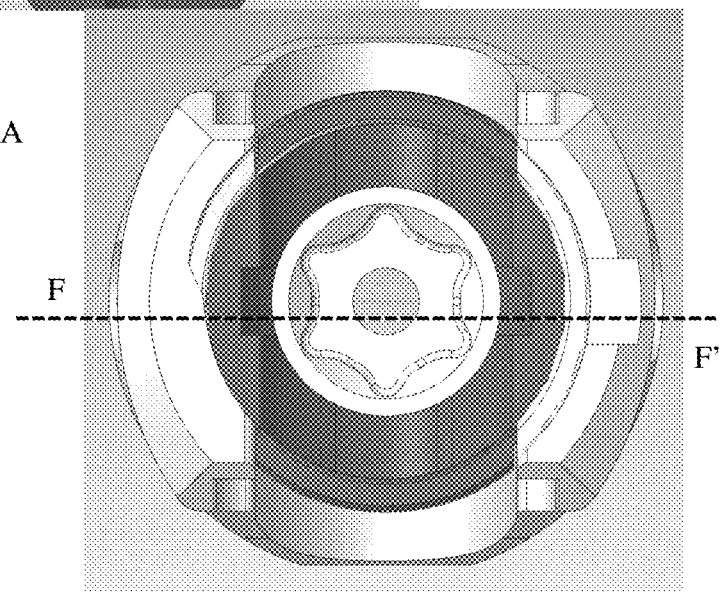

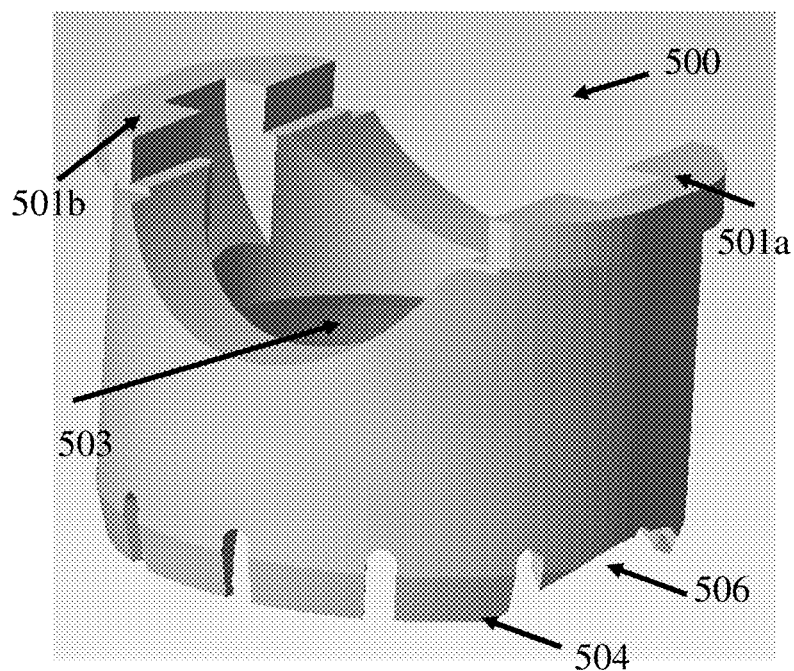
FIG. 32
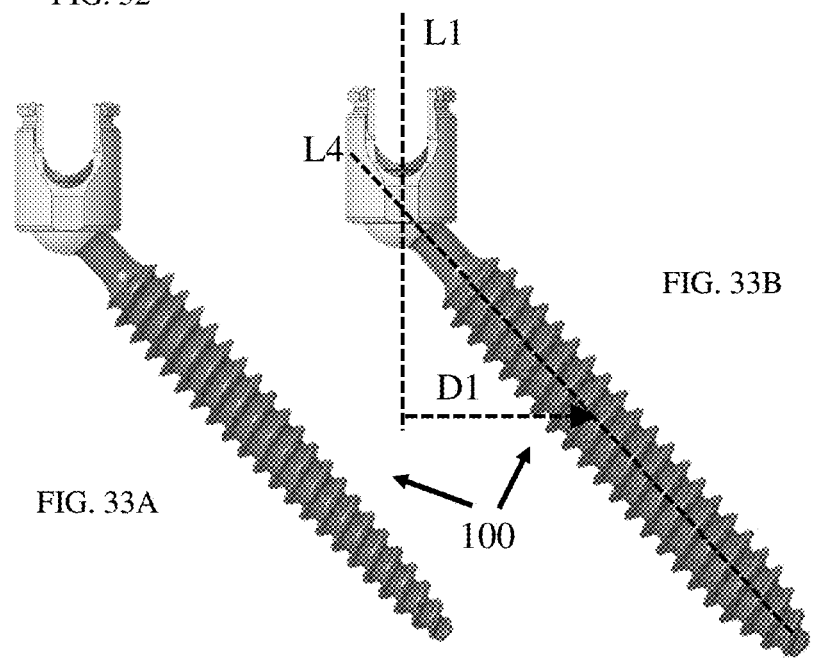
FIG. 33A
FIG. 33B

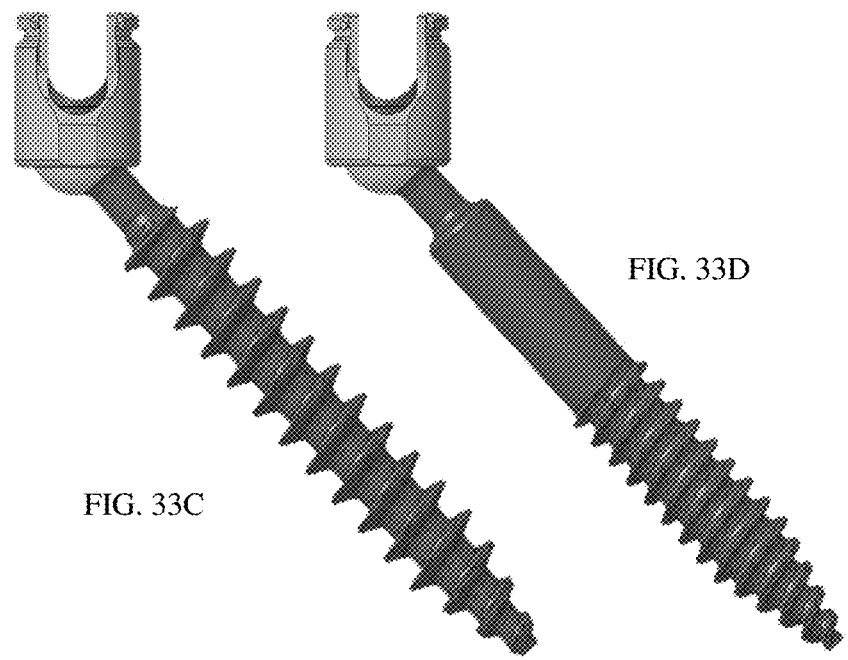
FIG. 33D
FIG. 33C
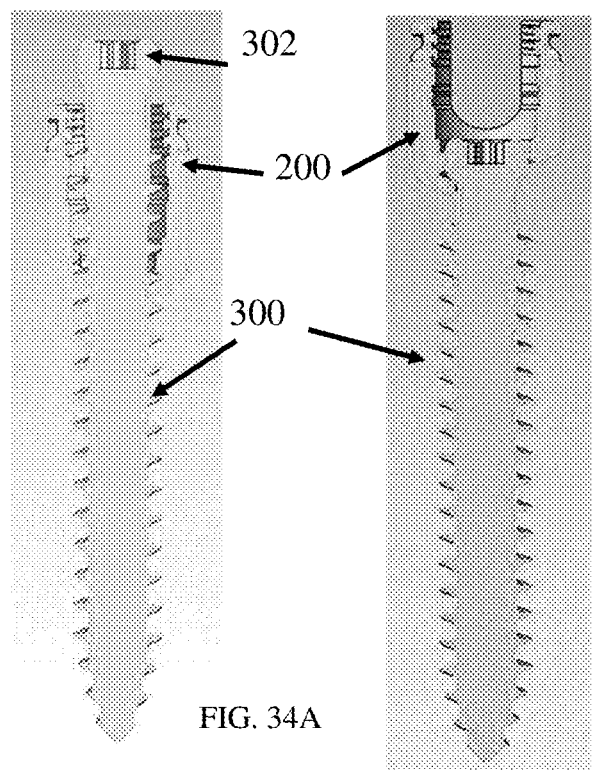
FIG. 34A
FIG. 34B

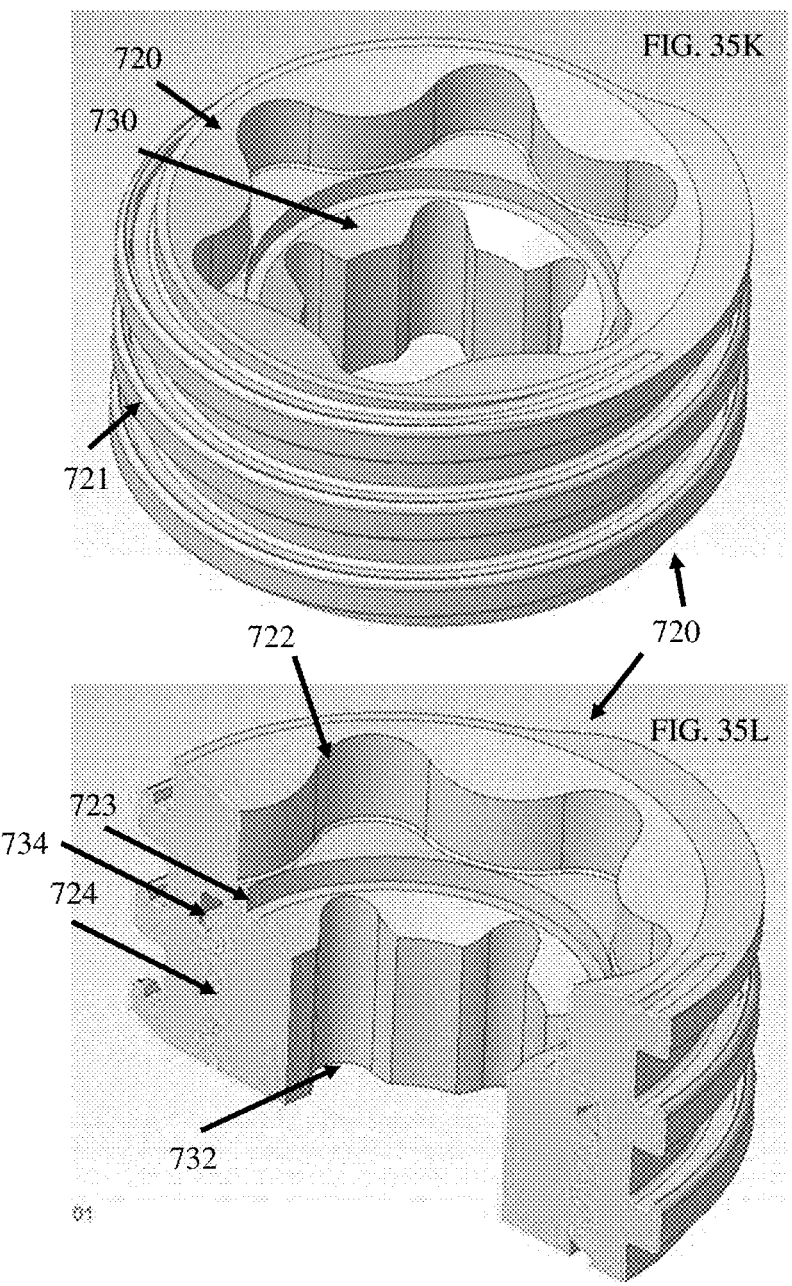

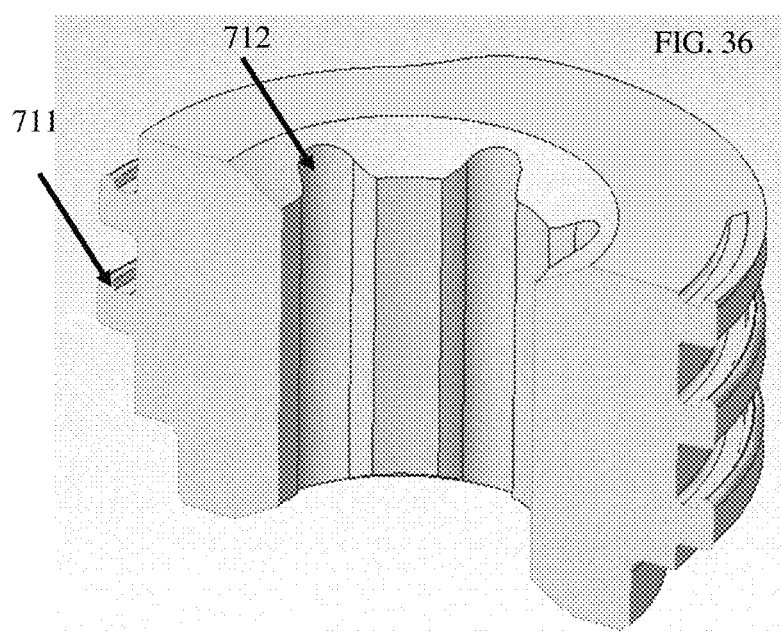

FIG. 37
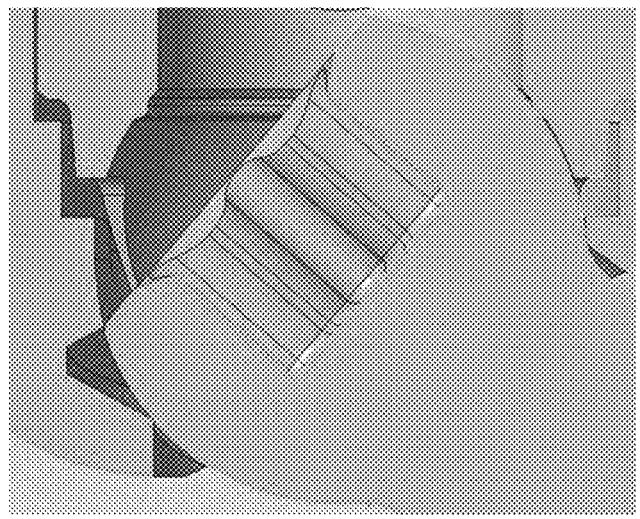
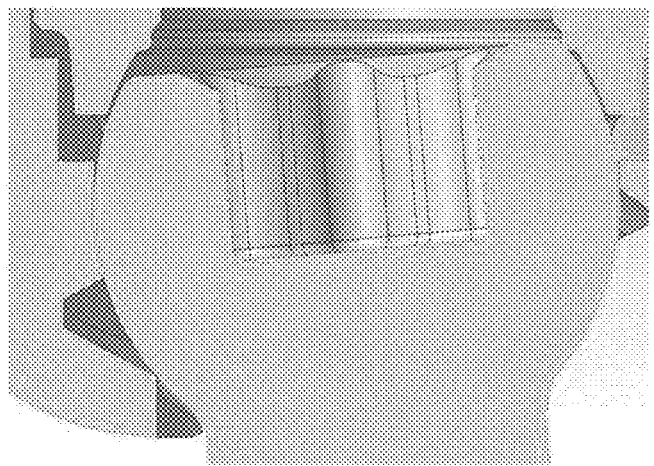
FIG. 38

POSTERIOR SPINAL FIXATION SCREWS

CROSS-REFERENCE TO RELATED APPLICATIONS

The present application is a non-provisional of, and claims the benefit of priority of U.S. Provisional Patent Application Ser. No. 62/851,100 filed May 22, 2019, the entire contents of which are incorporated herein by reference.

TECHNICAL FIELD

The present disclosure relates generally to spinal implants.

BACKGROUND OF THE DISCLOSURE

The spine is critical in human physiology for mobility, support, and balance. Spinal injuries can be debilitating or catastrophic to patients. Even small irregularities in the spine can cause devastating pain and loss of coordination.

Surgical procedures on the spine can often include application of bone anchors or bone screws that are connected by rigid spinal rods locked to each bone screw. The bone screws can often include an anchor component and a rod-housing component (or "tulip") that is often coupled to the anchor component in a manner that permits angular adjustability of the tulip relative to the anchor component.

SUMMARY OF THE DISCLOSURE

Bone screws and spinal rods are widely used in surgical procedures of the spine such as posterior spinal fixation. In certain spinal procedures, when bone screws are implanted in the desired positions, a spinal rod is seated in each tulip or receiver and locked in position. The angular adjustability of each receiver is also locked, either through the locking of the spinal rod, or independently thereof, to thus fix the connected vertebrae relative to each other. Bone screw configurations which allow increased angulation of the receiver relative to the bone screw shank are useful in certain situations where an increased pivot angle is needed (e.g. where there is an acute angle between the anchor component and rod trajectories). However, configurations that permit the increased angulation also tend to reduce the strength of the connection between the anchor component and rod-housing component. Therefore, an urgent need exists for new and improved bone screws with increased angulation housings but without the reduction in connection strength suffered in current solutions.

Existing bone screws used in spinal procedures can only be connected using a spinal rod locked in each of the receivers. There is an urgent need for improved bone screws that can be coupled or fixed in movement in specified direction(s) with freedom to move in other directions, and maintained ability to be connected to the spinal rod. Such improved bone screws can increase flexibility in surgical applications that needs complex deformity and involves trauma. There is also a need for two spinal rod connections to be included in a single bone screw in order to render flexibility in building a construct containing multiple screws and spinal rods.

In some spinal procedures, spinal rods with circular cross section may present difficulty in centering in the rod channel, limited strength and rigidity when the profile of the spinal rod is limited. Existing spinal rods may also only provide small contact surface with the closure top or set screw during lock down. Thus, there is a need for improvement of the existing spinal-rods with circular cross sections.

In certain spinal procedures focusing on ilium, sacrum, or sacroiliac regions, it is necessary to include either a sharp bend in the spinal rod to join with bone screws at superior levels or usage of a secondary rod or offset tulip connector. There is an urgent need to reduce the number of different connectors/screws and overall bulk of the construct while making a more rigid construct by reducing the number of connection points that can fail.

In some spinal procedures, increased angulation of the bone screw shank relative to the receiver may be desired. In applications related to iliac, sacrum, and/or pelvic regions, a marginal increase in tulip height can be tolerated for increased angulation that is essential to specific spinal procedures.

With traditional bone screws, once the spinal rod is placed and locked down, the construct is locked and the shank relative to the receiver is locked. However, in certain spinal procedures, e.g., a neuromuscular scoliosis case, there is a need for a simpler solution that can lock the bone screw(s) with or without a rod placed in the tulip rod slot and with or without a lock screw in the tulip. There is also a need to remove the step to provisionally lock the screw using external tools, but still maintain the capability that can be provided by the traditional provisional locking step, thereby making the procedure simpler to perform and more efficient.

Disclosed herein are bone screws and bone screw assemblies that address one or more needs for improvement on existing spinal implants, especially bone screws and their assemblies. The bone screws disclosed herein can advantageously provide better, simpler, more reliable, and more accurate performance in various spinal procedures.

In one aspect, disclosed herein is a bone screw comprising: a bone screw shank comprising a shank head; a receiver comprising: a base having a cavity therewithin, the cavity configured to securely receive the shank head; a pair of arms extending upwardly from the base; a rod channel defined between the pair of arms; and a lateral rod integral to the receiver and extending laterally away from the receiver.

In another aspect, disclosed herein is a bone screw assembly comprising: a first bone screw, the first bone screw comprising a first receiver having a first base with a first cavity therewithin, the first cavity configured to securely receive a first bone screw shank head; a first pair of arms extending upwardly from the base; a first rod channel defined between the first pair of arms; and a first lateral rod integral to the first receiver and extending laterally away from the first receiver; a second bone screw, the second bone screw comprising a second receiver having a second base with a second cavity therewithin, the second cavity configured to securely receive a second bone screw shank head; a second pair of arms extending upwardly from the second base; a second rod channel defined between the second pair of arms; and a second lateral rod integral to the second receiver and extending laterally away from the second receiver; and a rod to rod connector configured to securely receive the first lateral rod in a first bore and the second lateral rod in a second bore.

In another aspect, disclosed herein is a bone screw comprising: a bone screw shank comprising a shank head; a dual-head receiver comprising: a first receiver comprising a first base having a cavity therewithin, the cavity configured to securely receive the shank head; a first pair of arms extending upwardly from the first base; a first rod channel defined between the first pair of arms; a second receiver comprising a second base having a second rod channel defined between a second pair of arms; and a connection between the first receiver and the second receiver.

In yet another aspect, disclosed herein is a bone screw assembly comprising: a first bone screw comprising: a first bone screw shank comprising a first shank head; a first dual-head receiver comprising: a first receiver comprising a first base having a first cavity therewithin, the first cavity configured to securely receive the first shank head; a first pair of arms extending upwardly from the first base; a first rod channel defined between the first pair of arms; a second receiver comprising a second base having a second rod channel defined between a second pair of arms; and a first connection between the first receiver and the second receiver; a second bone screw comprising: a second bone screw shank comprising a second shank head; a second dual-head receiver comprising: a third receiver comprising a third base having a second cavity therewithin, the second cavity configured to securely receive the second shank head; a third pair of arms extending upwardly from the third base; a third rod channel defined between the third pair of arms; a fourth receiver comprising a fourth base having a fourth rod channel defined between a fourth pair of arms; and a second connection between the third receiver and the third receiver; and a lateral rod securely received in the second rod channel and the fourth rod channel thereby securely connecting the first bone screw and the second bone screw.

In yet another aspect, disclosed herein is a bone screw comprising: a bone screw shank comprising a shank head; a dual-head receiver comprising: a first receiver comprising a first base having a cavity therewithin, the cavity configured to securely receive the shank head; a first pair of arms extending upwardly from the first base; a first rod channel defined between the first pair of arms; a second receiver comprising a second base having a second rod channel defined between a second pair of arms; and a connection between the first receiver and the second receiver.

In yet another aspect, disclosed herein is a bone screw assembly comprising: a first bone screw comprising: a first bone screw shank comprising a first shank head; a first dual-head receiver comprising: a first receiver comprising a first base having a first cavity therewithin, the first cavity configured to securely receive the first shank head; a first pair of arms extending upwardly from the first base; a first rod channel defined between the first pair of arms; a second receiver comprising a second base having a second rod channel defined between a second pair of arms; and a first connection between the first receiver and the second receiver; a second bone screw comprising: a second bone screw shank comprising a second shank head; a second dual-head receiver comprising: a third receiver comprising a third base having a second cavity therewithin, the second cavity configured to securely receive the second shank head; a third pair of arms extending upwardly from the third base; a third rod channel defined between the third pair of arms; a fourth receiver comprising a fourth base having a fourth rod channel defined between a fourth pair of arms; and a second connection between the third receiver and the third receiver; and a rod securely received in the second rod channel and the fourth rod channel thereby securely connecting the first bone screw and the second bone screw.

In yet another aspect, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a flat top edge, two flat side edges, and a curved V-shaped bottom edge.

In yet another aspect, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a curved top edge, two curved side edges, and a curved bottom edge.

In yet another aspect, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a flat top edge and a curved or flat bottom edge.

In yet another aspect, disclosed herein is a bone screw comprising: a bone screw shank comprising a shank head; a dual-head receiver comprising: a first receiver comprising a first base having a cavity therewithin, the cavity configured to securely receive the shank head; a first top having an opening to receive a locking element therewithin thereby locking the shank head within the cavity; a second receiver comprising a second base having a rod channel defined between a pair of arms; and a connection between the first receiver and the second receiver.

In yet another aspect, disclosed herein is a bone screw comprising: a bone screw shank comprising a shank head; a receiver comprising a base having a cavity therewithin, the cavity configured to accept insertion of the shank head from a bottom of the receiver; a pair of arms extending upwardly from the base; and a rod channel defined between the pair of arms; a load ring configured to be bottom-loaded into the receiver prior to the insertion of the shank head, wherein the load ring comprises a pair of legs connected by two concave surfaces at its proximal side; and a clip ring configured to be inserted into a groove located in an inner surface at or near the bottom of the receiver in an open position when the load ring and the shank head are pushed proximal to a locking position, wherein in the open position, each of the pair of legs faces an opening of the rod channel and each of the concave surfaces is aligned with one of the pair of arms.

In yet another aspect, disclosed herein is a method of assembly of a bone screw, the method comprising: providing a bone screw shank comprising a shank head; providing a receiver comprising a base having a cavity therewithin, the cavity configured to securely accept insertion of the shank head from a bottom of the receiver; a pair of arms extending upwardly from the base; and a rod channel defined between the pair of arms; providing a load ring configured to be bottom-loaded into the receiver prior to the insertion of the shank head, wherein the load ring comprises a pair of legs connected by two concave surfaces at its proximal side; and providing a clip ring configured to be inserted into a groove located in an inner surface at or near the bottom of the receiver thereby pushing the load ring and the shank head into an open position that is proximal to a locking position, wherein in the open position, each of the pair of legs is at least partly facing an opening of the rod channel and each of the concave surfaces are aligned with the pair of arms.

In yet another aspect, disclosed herein is a method of assembly of a bone screw, the method comprising: loading a load ring from a bottom end of a receiver of the bone screw through a cavity thereof prior to the insertion of the shank head, wherein loading the load ring comprises twisting the load ring so that each of two opposing concave surfaces at a proximal surface of the load ring is aligned with an upwardly extending arm of the receiver and pushing the load ring proximally; inserting the shank head into the receiver from the bottom end thereof till access to a groove in an inner surface of the receiver at or near a distal end thereof is open; inserting a clip ring into the groove in the inner surface of the receiver; pushing the load ring and the shank head distally; and twisting the load ring in to a locked position so that each of the two concave surfaces at the top surface of the load ring is aligned with an opening of the rod channel of the receiver, wherein the load ring and the shank head is locked from distal movement.

In yet another aspect, disclosed herein is a bone screw comprising: a bone screw shank comprising a shank head; a receiver comprising a base having a cavity therewithin, the cavity configured to securely accept insertion of the shank head from a top of the receiver; a pair of arms extending upwardly from the base; and a rod channel defined between the pair of arms, wherein the base comprises a recess formed in a bottom surface thereof, wherein the base and the recess are shaped and sized to allow angulation in a range of about 0 degrees to about 60 degrees in a first lateral direction and prevent angulation of greater than about 0 degrees in a second lateral direction opposite the first lateral direction; and a load ring configured to be top-loaded into the receiver subsequent to the insertion of the shank head, wherein the load ring comprises a pair of legs connected by two concave surfaces at its proximal side.

In yet another aspect, disclosed herein is a bone screw assembly comprising: a bone screw shank comprising a shank head; a receiver comprising a base having a cavity therewithin, the cavity configured to securely accept insertion of the shank head from a top of the receiver; a pair of arms extending upwardly from the base; and a rod channel defined between the pair of arms; a compression element configured to be top-loaded into the receiver subsequent to the insertion of the shank head, wherein the compression element comprises a pair of legs connected by two concave surfaces at its proximal side, and a lock screw configured to be top-loaded into the receiver thereby locking the shank head relative to the receiver.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 19A-19B show exemplary embodiments of the dual-head bone screws disclosed herein; in this case, a perspective view (FIG. 19A) and side view (FIG. 19B) of the dual-head bone screws with the connection between the two receivers integral to the first receiver but rotatable and/or translatable relative to the second receiver; and FIGS. 19C-19D show exemplary embodiments of the dual-head bone screws disclosed herein; in this case, top views of the dual-head bone screws with a connection that is rotatable and/or translatable relative to one of the two receivers;

FIGS. 21A-21B show exemplary embodiments of the bone screw in FIG. 20 in cross-sectional views, in accordance with embodiments herein;

FIGS. 22A-22I show exemplary embodiments of the bone screws disclosed herein during the process of assembly thereof, in accordance with embodiments herein;

FIGS. 23A-23C show exemplary embodiments of the bone screw after the bone screw in FIGS. 20-22I is assembled, in accordance with embodiments herein;

FIG. 32 shows an exemplary embodiment of the load ring of the bone screws disclosed herein in a perspective view, in accordance with embodiments herein;

FIGS. 33A-33D show exemplary embodiments of the bone screws with different bone screw shanks, in accordance with embodiments herein;

FIGS. 34A-34B show exemplary embodiments of the bone screws; in this case, the receiver and the bone screw shank during top-loading assembly, in accordance with embodiments herein;

FIGS. 35H-35L show exemplary embodiments of the bone screws disclosed herein, in this case, the lock screw, in accordance with embodiments herein;

FIG. 36 shows an exemplary embodiment of the bone screws disclosed herein, in this case, the lock screw, in accordance with embodiments herein;

FIGS. 37-38 show exemplary embodiments of the bone screws disclosed herein, in this case, the receiver and the shank head bone screw disclosed herein, in accordance with embodiments herein;

DETAILED DESCRIPTION OF THE DISCLOSURE

Figure 1:
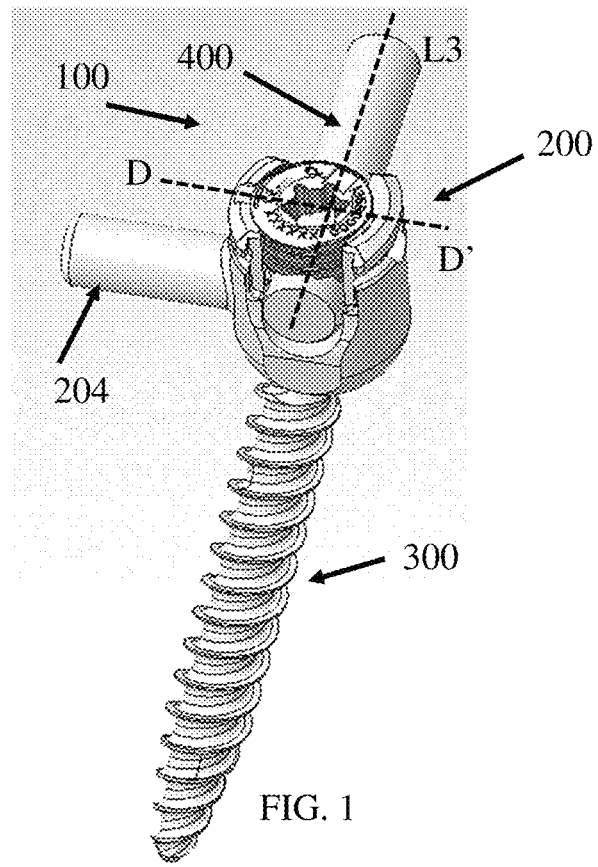
FIG. 1 shows an exemplary embodiment of the bone screws; in this case, a bone screw with a lateral rod in a perspective view, in accordance with the embodiments herein.

In certain embodiments, disclosed herein is a bone screw comprising: a bone screw shank comprising a shank head; a receiver comprising: a base having a cavity therewithin, the cavity configured to securely receive the shank head; a pair of arms extending upwardly from the base; a rod channel defined between the pair of arms; and a lateral rod integral to the receiver and extending laterally away from the receiver. In some embodiments, the lateral rod extends laterally from an outer surface of one of the pair of arms. In some embodiments, the receiver comprises a longitudinal axis extending through a bottom end of the base toward a top end of the pair of arms, and wherein the lateral rod extends perpendicular to the longitudinal axis of the receiver. In some embodiments, the lateral rod is perpendicular to a first direction of extension of the rod channel, or wherein the lateral rod is tilted by an angle from the first direction of extension of the rod channel. In some embodiments, the lateral rod is straight, curved, or bent. In some embodiments, the lateral rod comprises a size that is configured to be received in a rod to rod connector or a rod channel of a second bone screw. In some embodiments, the lateral rod comprises a cross-sectional shape that is identical to a spinal rod that is configured to be received in the rod channel of the bone screw. In some embodiments, the lateral rod comprises a substantially cylindrical shape. In some embodiments, the receiver comprising a tool engagement groove at an outer surface of the pair of arms at or near a top end thereof, and wherein a top edge of the lateral rod is distal to the tool engagement groove. In some embodiments, a bottom edge of the lateral rod is proximal to a bottom surface of the base. In some embodiments, the bone screw is a poly-axial screw.

In certain embodiments, disclosed herein is a bone screw assembly comprising: a first bone screw, the first bone screw comprising a first receiver having a first base with a first cavity therewithin, the first cavity configured to securely receive a first bone screw shank head; a first pair of arms extending upwardly from the base; a first rod channel defined between the first pair of arms; and a first lateral rod integral to the first receiver and extending laterally away from the first receiver; a second bone screw, the second bone screw comprising a second receiver having a second base with a second cavity therewithin, the second cavity configured to securely receive a second bone screw shank head; a second pair of arms extending upwardly from the second base; a second rod channel defined between the second pair of arms; and a second lateral rod integral to the second receiver and extending laterally away from the second receiver; and a rod to rod connector configured to securely receive the first lateral rod in a first bore and the second lateral rod in a second bore. In some embodiments, the first bore and the second bore of the rod to rod connector are substantially parallel to each other. In some embodiments, the first rod channel and the second rod channel are configured to receive a longitudinal rod therewithin. In some embodiments, the first bone screw is anchored in a first vertebral bone, and the second bone screw is anchored in a second vertebral bone. In some embodiments, the first bone screw or the second bone screw is a poly-axial screw. In some embodiments, the rod to rod connector comprises a first opening at a top thereof, the first opening connected to the first bore. In some embodiments, the first opening is configured to receive a closure top that presses against the first lateral rod thereby securing the first lateral rod to the rod to rod connector. In some embodiments, the rod to rod connector comprises a second opening at a top thereof, the second opening connected to the second bore. In some embodiments, the second opening is configured to receive a closure top that presses against the second lateral rod thereby securing the second lateral rod to the rod to rod connector.

In certain embodiments, disclosed herein is a bone screw comprising: a bone screw shank comprising a shank head; a dual-head receiver comprising: a first receiver comprising a first base having a cavity therewithin, the cavity configured to securely receive the shank head; a first pair of arms extending upwardly from the first base; a first rod channel defined between the first pair of arms; a second receiver comprising a second base having a second rod channel defined between a second pair of arms; and a connection between the first receiver and the second receiver. In some embodiments, the connection is integral to the first and second receivers, or the connection is integral to one of the first or second receiver but movable relative to the other one of the first or second receiver. In some embodiments, the first rod channel extends in a first direction, and the second rod channel extends in a second direction substantially perpendicular to the first direction, or wherein the second rod channel extends in a second direction that is tilted by an angle from the first direction. In some embodiments, at least part of the first pair of arms face an opening of the second channel. In some embodiments, a bottom surface of the second base is proximal to a bottom surface of the first base. In some embodiments, the first receiver comprises a longitudinal axis extending in a proximal to distal direction, and wherein the connection between the first receiver and the second receiver extends substantially perpendicular to the longitudinal axis of the first receiver. In some embodiments, the connection between the first receiver and the second receiver extends in a direction that is perpendicular to a direction of extension from the first rod channel or tilted by an angle from the direction of extension from the first rod channel. In some embodiments, the connection between the first receiver and the second receiver extends laterally from an outer surface of one of the first pair of arms. In some embodiments, the connection between the first receiver and the second receiver extends laterally from an outer surface of an opening of the second rod channel. In some embodiments, the first rod channel and the second rod channel comprise an identical size or shape. In some embodiments, the first receiver comprising a first tool engagement groove at an outer surface of the first pair of arms at or near a top surface thereof, and wherein a top edge of the connection between the first receiver and the second receiver is distal to the first tool engagement groove. In some embodiments, the second receiver comprising a second tool engagement groove at an outer surface of the second pair of arms at or near a top surface thereof, and wherein a top edge of the connection between the first receiver and the second receiver is distal to the second tool engagement groove. In some embodiments, a bottom surface of the connection between the first receiver and the second receiver is proximal to a bottom surface of the first base. In some embodiments, the first receiver is configured to receive a first closure top that presses against a first rod within the first rod channel thereby securing the first rod therewithin. In some embodiments, the second receiver is configured to receive a second closure top that presses against a second rod within the second rod channel thereby securing the second rod therewithin. In some embodiments, the first receiver comprises a U-shape opening defined by at least part of an edge of each of the first pair of arms. In some embodiments, the second receiver comprises a U-shape opening defined by at least part of an edge of each of the second pair of arms. In some embodiments, the connector is narrower than the first receiver along a direction of extension of the first rod channel or the second rod channel. In some embodiments, second receiver is shorter than the first receiver along a proximal to distal direction. In some embodiments, the second rod channel extends laterally beyond an edge of each of the second pair of arms. In some embodiments, the second rod channel extends laterally beyond a lateral edge of the second receiver. The bone screw can be a polyaxial screw. In some embodiments, the second rod channel comprises a half-moon opening at a lateral edge of the second receiver. In some embodiments, the first and second rod channels are at an identical level along the proximal to distal direction. In some embodiments, the first and second rod channels are at two different levels along the proximal to distal direction.

In certain embodiments, disclosed herein is a bone screw assembly comprising: a first bone screw comprising: a first bone screw shank comprising a first shank head; a first dual-head receiver comprising: a first receiver comprising a first base having a first cavity therewithin, the first cavity configured to securely receive the first shank head; a first pair of arms extending upwardly from the first base; a first rod channel defined between the first pair of arms; a second receiver comprising a second base having a second rod channel defined between a second pair of arms; and a first connection between the first receiver and the second receiver; a second bone screw comprising: a second bone screw shank comprising a second shank head; a second dual-head receiver comprising: a third receiver comprising a third base having a second cavity therewithin, the second cavity configured to securely receive the second shank head; a third pair of arms extending upwardly from the third base; a third rod channel defined between the third pair of arms; a fourth receiver comprising a fourth base having a fourth rod channel defined between a fourth pair of arms; and a second connection between the third receiver and the third receiver; and a lateral rod securely received in the second rod channel and the fourth rod channel thereby securely connecting the first bone screw and the second bone screw. In some embodiments, the first rod channel extends in a first direction, and the second rod channel extends in a second direction substantially perpendicular to the first direction or at an acute angle to the first direction. In some embodiments, at least part of the first pair of arms face an opening of the second channel. In some embodiments, a bottom surface of the second base is proximal to a bottom surface of the first base. In some embodiments, the first receiver comprises a longitudinal axis extending in a proximal to distal direction, and wherein the connection between the first receiver and the second receiver extends substantially perpendicular to the longitudinal axis of the first receiver. In some embodiments, the connection between the first receiver and the second receiver extends laterally from an outer surface of one of the first pair of arms. In some embodiments, the connection between the first receiver and the second receiver extends laterally from an outer surface of an opening of the second rod channel. In some embodiments, the first rod channel and the second rod channel comprise an identical size or shape. In some embodiments, the first receiver comprising a first tool engagement groove at an outer surface of the first pair of arms at or near a top surface thereof, and wherein a top edge of the connection between the first receiver and the second receiver is distal to the first tool engagement groove. In some embodiments, the second receiver comprising a second tool engagement groove at an outer surface of the second pair of arms at or near a top surface thereof, and wherein a top edge of the connection between the first receiver and the second receiver is distal to the second tool engagement groove. In some embodiments, a bottom surface of the connection between the first receiver and the second receiver is proximal to a bottom surface of the first base. In some embodiments, the first receiver is configured to receive a first closure top that presses against a first rod within the first rod channel thereby securing the first rod therewithin. In some embodiments, the second receiver is configured to receive a second closure top that presses against a second rod within the second rod channel thereby securing the second rod therewithin. In some embodiments, the first receiver comprises a U-shape opening defined by at least part of an edge of each of the first pair of arms. In some embodiments, the second receiver comprises a U-shape opening defined by at least part of an edge of each of the second pair of arms. In some embodiments, the connector is narrower than the first receiver. In some embodiments, second receiver is shorter than the first receiver along a proximal to distal direction. In some embodiments, the second rod channel extends laterally beyond an edge of each of the second pair of arms. In some embodiments, the second rod channel extends laterally beyond a lateral edge of the second receiver. The bone screw can be a polyaxial screw. In some embodiments, the second rod channel comprises a half-moon opening at a lateral edge of the second receiver. In some embodiments, the first connection is integral to the first and second receivers, or the first connection is integral to one of the first or second receiver but movable relative to the other one of the first or second receiver. In some embodiments, the second connection is integral to the third and fourth receivers, or the connection is integral to one of the first or second receiver but movable relative to the other one of the first or second receiver.

In certain embodiments, disclosed herein is a bone screw comprising: a bone screw shank comprising a shank head; a dual-head receiver comprising: a first receiver comprising a first base having a cavity therewithin, the cavity configured to securely receive the shank head; a first pair of arms extending upwardly from the first base; a first rod channel defined between the first pair of arms; a second receiver comprising a second base having a second rod channel defined between a second pair of arms; and a connection between the first receiver and the second receiver. In some embodiments, the connection is integral to the first and second receivers, or the connection is integral to one of the first or second receiver but movable relative to the other one of the first or second receiver. In some embodiments, the first rod channel extends in a first direction, and the second rod channel extends in a second direction substantially parallel to the first direction. In some embodiments, the first rod channel extends in a first direction, and the second rod channel extends in a second direction that is tilted by an angle with the first direction. In some embodiments, the first rod channel and the second rod channel are at an identical level along a proximal to distal direction. In some embodiments, the first rod channel and the second rod channel are at two different levels along a proximal to distal direction. In some embodiments, the first pair of arms face the second pair of arms. In some embodiments, a bottom surface of the second base is proximal to a bottom surface of the first base. In some embodiments, the first receiver comprises a longitudinal axis extending in a proximal to distal direction, and wherein the connection between the first receiver and the second receiver extends substantially perpendicular to the longitudinal axis of the first receiver. In some embodiments, the connection between the first receiver and the second receiver extends in a direction that is perpendicular to a direction of extension of the first rod channel or tilted by an angle from the direction of extension of the first rod channel. In some embodiments, the connection between the first receiver and the second receiver extends laterally from an outer surface of one of the first pair of arms. In some embodiments, the connection between the first receiver and the second receiver extends laterally from an outer surface of one of the second pair of arms. In some embodiments, the connection between the first receiver and the second receiver extends laterally from an outer surface of the first base to an outer surface of the second base. In some embodiments, the first rod channel and the second rod channel comprise an identical size or shape. In some embodiments, the first receiver comprising a first tool engagement groove at an outer surface of the first pair of arms at or near a top surface thereof, and wherein a top edge of the connection between the first receiver and the second receiver is proximal to the first tool engagement groove. In some embodiments, the second receiver comprising a second tool engagement groove at an outer surface of the second pair of arms at or near a top surface thereof, and wherein a top edge of the connection between the first receiver and the second receiver is distal to the second tool engagement groove. In some embodiments, a bottom surface of the connection between the first receiver and the second receiver is proximal to a bottom surface of the first base. In some embodiments, the first receiver comprises a proximal opening that is configured to receive a first closure top that presses against a first rod within the first rod channel thereby securing the first rod therewithin. In some embodiments, the second receiver comprises a proximal opening that is configured to receive a second closure top that presses against a second rod within the second rod channel thereby securing the second rod therewithin. In some embodiments, the first receiver comprises a U-shape opening defined by at least part of an edge of each of the first pair of arms. In some embodiments, the second receiver comprises a U-shape opening defined by at least part of an edge of each of the second pair of arms. In some embodiments, the second receiver is shorter than the first receiver along a proximal to distal direction. In some embodiments, the first rod channel and the second rod channel are at an identical level along a proximal to distal direction. In some embodiments, the bone screw is a polyaxial screw.

In certain embodiments, disclosed herein is a bone screw assembly comprising: a first bone screw comprising: a first bone screw shank comprising a first shank head; a first dual-head receiver comprising: a first receiver comprising a first base having a first cavity therewithin, the first cavity configured to securely receive the first shank head; a first pair of arms extending upwardly from the first base; a first rod channel defined between the first pair of arms; a second receiver comprising a second base having a second rod channel defined between a second pair of arms; and a first connection between the first receiver and the second receiver; a second bone screw comprising: a second bone screw shank comprising a second shank head; a second dual-head receiver comprising: a third receiver comprising a third base having a second cavity therewithin, the second cavity configured to securely receive the second shank head; a third pair of arms extending upwardly from the third base;

a third rod channel defined between the third pair of arms; a fourth receiver comprising a fourth base having a fourth rod channel defined between a fourth pair of arms; and a second connection between the third receiver and the fourth receiver; and a rod securely received in the second rod channel and the fourth rod channel thereby securely connecting the first bone screw and the second bone screw. In some embodiments, the first rod channel extends in a first direction, and the second rod channel extends in a second direction substantially parallel to the first direction. In some embodiments, the first pair of arms faces the second pair of arms. In some embodiments, a bottom surface of the second base is proximal to a bottom surface of the first base. In some embodiments, the first receiver comprises a longitudinal axis extending in a proximal to distal direction, and wherein the connection between the first receiver and the second receiver extends substantially perpendicular to the longitudinal axis of the first receiver. In some embodiments, the connection between the first receiver and the second receiver extends laterally from an outer surface of one of the first pair of arms. In some embodiments, the connection between the first receiver and the second receiver extends laterally from an outer surface of one of the second pair of arms. In some embodiments, the first rod channel and the second rod channel comprise an identical size or shape. In some embodiments, the first receiver comprising a first tool engagement groove at an outer surface of the first pair of arms at or near a top surface thereof, and wherein a top edge of the connection between the first receiver and the second receiver is proximal to the first tool engagement groove. In some embodiments, the second receiver comprising a second tool engagement groove at an outer surface of the second pair of arms at or near a top surface thereof, and wherein a top edge of the connection between the first receiver and the second receiver is proximal to the second tool engagement groove. In some embodiments, a bottom surface of the connection between the first receiver and the second receiver is proximal to a bottom surface of the first base. In some embodiments, the first receiver is configured to receive a first closure top that presses against a first rod within the first rod channel thereby securing the first rod therewithin. In some embodiments, the second receiver is configured to receive a second closure top that presses against a second rod within the second rod channel thereby securing the second rod therewithin. In some embodiments, the first receiver comprises a U-shape opening defined by at least part of an edge of each of the first pair of arms. In some embodiments, the second receiver comprises a U-shape opening defined by at least part of an edge of each of the second pair of arms. In some embodiments, the second receiver is shorter than the first receiver along a proximal to distal direction. In some embodiments, the bone screw is a polyaxial screw. In some embodiments, the first rod channel and the second rod channel are at an identical level or at two different levels along a proximal to distal direction. In some embodiments, the first connection is integral to the first and second receivers, or the first connection is integral to one of the first or second receiver but movable relative to the other one of the first or second receiver. In some embodiments, the second connection is integral to the third and fourth receivers, or the connection is integral to one of the first or second receiver but movable relative to the other one of the first or second receiver.

In certain embodiments, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a flat top edge, two flat side edges, and a curved V-shaped bottom edge. In some embodiments, the non-circular cross section comprises curved corners. In some embodiments, the spinal rod further comprises a protrusion extending from an end surface of the elongate body, the protrusion integral to the elongate body. In some embodiments, the protrusion comprises a second non-circular cross section that is smaller than the non-circular cross section of the elongate body. In some embodiments, the second non-circular cross section has a shape that is different from the non-circular cross section of the elongate body. In some embodiments, the second non-circular cross section comprises a hexagon shape with rounded corners. In some embodiments, the protrusion is configured to be grabbed by a tool for positioning the spinal rod within the spinal rod channel. In some embodiments, the resistance to torsion of the elongate body is greater than a spinal rod of circular cross section that fits into the spinal rod channel of the bone screw receiver. In some embodiments, the flat top edge, the curved V-shaped bottom edge, or both are configured to increase a contacting surface to the spinal rod channel, a closure top, or both.

In certain embodiments, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a curved top edge, two curved side edges, and a curved bottom edge. In some embodiments, the non-circular cross section comprises curved connection between the curved edge and either one of the two curved side edges, and between the curved bottom edge and either one of the two curved side edges. In some embodiments, the spinal rod further comprises a protrusion integral to the elongate body, the protrusion extending from an end surface of the elongate body. In some embodiments, the protrusion comprises a second non-circular cross section that is smaller than the non-circular cross section of the elongate body. In some embodiments, the second non-circular cross section has a shape that is different from the non-circular cross section of the elongate body. In some embodiments, the second non-circular cross section comprises a hexagon shape with rounded corners. In some embodiments, the resistance to torsion of the elongate body is greater than a spinal rod of circular cross section that fits into the spinal rod channel of the bone screw receiver. In some embodiments, one or more of the curved top edge, curved bottom edge, and two curved side edges are convex.

In certain embodiments, disclosed herein is a spinal rod, comprising: an elongate body with a non-circular cross section, wherein elongate body is configured to be slidely insertable into a spinal rod channel of a bone screw receiver, and is configured to be secured within the spinal rod channel of the bone screw receiver by a closure top pressing against the elongate body, wherein the non-circular cross section comprises a flat top edge and a curved or flat bottom edge. In some embodiments, the non-circular cross section comprises curved connection between adjacent edges. In some embodiments, the spinal rod further comprises a protrusion integral to the elongate body, the protrusion extending from an end surface of the elongate body. In some embodiments, the protrusion comprises a second non-circular cross section that is smaller than the non-circular cross section of the elongate body. In some embodiments, the second non-circular cross section has a shape that is different from the non-circular cross section of the elongate body. In some embodiments, the second non-circular cross section comprises a hexagon shape with rounded corners. In some embodiments, the resistance to torsion of the elongate body is greater than a spinal rod of circular cross section that fits into the spinal rod channel of the bone screw receiver. In some embodiments, one or more of edges are convex. In some embodiments, the non-circular cross section comprises 10 edges including 5 flat edges and 5 convex edges. In some embodiments, the non-circular cross section comprises 12 edges including 6 flat edges and 6 convex edges. In some embodiments, comprises a polygon shape with rounded connections between two adjacent edges.

In certain embodiments, disclosed herein is a bone screw comprising: a bone screw shank comprising a shank head; a dual-head receiver comprising: a first receiver comprising a first base having a cavity therewithin, the cavity configured to securely receive the shank head; a first top having an opening to receive a locking element therewithin thereby locking the shank head within the cavity; a second receiver comprising a second base having a rod channel defined between a pair of arms; and a connection between the first receiver and the second receiver.

In some embodiments, the connection is integral to the first and second receivers, or the connection is integral to one of the first or second receiver but movable relative to the other one of the first or second receiver. In some embodiments, a bottom surface of the second base is proximal or distal to a bottom surface of the first base. In some embodiments, a bottom surface of the second base and a bottom surface of the first base sit at an identical level along a proximal to distal direction. In some embodiments, a top surface of the first top is distal to a top surface of the pair of arms of the second receiver. In some embodiments, the first receiver has a lower profile than the second receiver along a proximal to distal direction. In some embodiments, the first receiver comprises a longitudinal axis extending in a proximal to distal direction, and wherein the connection between the first receiver and the second receiver extends substantially perpendicular to the longitudinal axis of the first receiver. In some embodiments, the second receiver comprises a longitudinal axis extending in a proximal to distal direction, and wherein the connection between the first receiver and the second receiver extends substantially perpendicular to the longitudinal axis of the second receiver. In some embodiments, the rod channel extends in a first direction, wherein the connection between the first receiver and the second receiver extends in a direction that is perpendicular to the first direction, or wherein the connection between the first receiver and the second receiver extends in a direction that is tilted by an angle from the first direction. In some embodiments, the connection between the first receiver and the second receiver extends laterally from an outer surface of one of the pair of arms. In some embodiments, the connection between the first receiver and the second receiver extends laterally from an outer surface of the first top, the first base, or both of the first receiver. In some embodiments, the second receiver comprising a tool engagement groove at an outer surface of the second pair of arm at or near a top of the second receiver, and wherein a top edge of the connection between the first receiver and the second receiver is distal to the second tool engagement groove. In some embodiments, a bottom surface of the connection between the first receiver and the second receiver is proximal to a bottom surface of the first base. In some embodiments, the second receiver is configured to receive a closure top that presses against a rod within the rod channel thereby securing the rod therewithin. In some embodiments, the locking element is a lock screw or a second closure top that is smaller in its longitudinal cross section than the closure top of the second receiver. In some embodiments, the connector is narrower than the first receiver. In some embodiments, second receiver is longer than the first receiver along a proximal to distal direction. In some embodiments, a maximal dimension in a longitudinal cross section of the first base is smaller than a maximal dimension in the longitudinal cross section of the second base. In some embodiments, the bone screw is a polyaxial screw. In some embodiments, the bone screw is an iliac screw.

In certain embodiments, disclosed herein is a bone screw comprising: a bone screw shank comprising a shank head; a receiver comprising a base having a cavity therewithin, the cavity configured to accept insertion of the shank head from a bottom of the receiver; a pair of arms extending upwardly from the base; and a rod channel defined between the pair of arms; a load ring configured to be bottom-loaded into the receiver prior to the insertion of the shank head, wherein the load ring comprises a pair of legs connected by two concave surfaces at its proximal side; and a clip ring configured to be inserted into a groove located in an inner surface at or near the bottom of the receiver in an open position when the load ring and the shank head are pushed proximal to a locking position, wherein in the open position, each of the pair of legs faces an opening of the rod channel and each of the concave surfaces is aligned with one of the pair of arms. In some embodiments, the bone screw is a polyaxial screw. In some embodiments, the bone screw shank is configured to rotate about a longitudinal axis of the receiver for about 0 degrees to about 40 degrees before a rod is secured in the rod channel. In some embodiments, a maximal polyaxial angulation between the bone screw shank and a longitudinal axis of the receiver is greater than 40 degrees. In some embodiments, the load ring is configured to be pushed proximally and rotated away from the locked position during insertion of the shank head into the receiver. In some embodiments, the load ring is configured to be pushed distally and rotated to the lock position subsequent to insertion of the clip ring. In some embodiments, the load ring is configured to rotate about a longitudinal axis of the receiver for about 90 degrees from the open position to the lock position. In some embodiments, the shank head is configured to be pushed distally from the open position to the lock position subsequent to insertion of the clip ring. In some embodiments, the load ring comprises an inner surface and a distal portion thereof accommodates a shape of at least part of the shank head. In some embodiments, the load ring comprises a top opening allowing access to the shank head from a top of the receiver. In some embodiments, the load ring comprises an outer groove between the pair of legs and a bottom portion thereof. In some embodiments, the bottom portion of the load ring is substantially cylindrical. In some embodiments, a cross section at the bottom portion of the load ring is greater than a cross section at the pair of legs thereof. In some embodiments, the pair of arms comprises a protrusion on an inner surface thereof, the protrusion configured to prevent proximal translation of the load ring. In some embodiments, at least part of the shank head extends beyond the distal portion of the inner surface of the load ring when the bone screw shank is rotated from the longitudinal axis of the receiver. In some embodiments, the bone screw is an iliac screw or a sacral screw. In some embodiments, the receiver comprises a longitudinal axis extending through a bottom of the base toward a top of the pair of arms. In some embodiments, the receiver comprising a tool engagement groove at an outer surface of the pair of arms at or near a top thereof. In some embodiments, the bone screw head comprises a maximal outer diameter that is greater than or equal to an outer diameter of a closure top that is configured to lock a spinal rod within the rod channel.

In certain embodiments, disclosed herein is a method of assembly of a bone screw, the method comprising: providing a bone screw shank comprising a shank head; providing a receiver comprising a base having a cavity therewithin, the cavity configured to securely accept insertion of the shank head from a bottom of the receiver; a pair of arms extending upwardly from the base; and a rod channel defined between the pair of arms; providing a load ring configured to be bottom-loaded into the receiver prior to the insertion of the shank head, wherein the load ring comprises a pair of legs connected by two concave surfaces at its proximal side; and providing a clip ring configured to be inserted into a groove located in an inner surface at or near the bottom of the receiver thereby pushing the load ring and the shank head into an open position that is proximal to a locking position, wherein in the open position, each of the pair of legs is at least partly facing an opening of the rod channel and each of the concave surfaces are aligned with the pair of arms.

In certain embodiments, disclosed herein is a method of assembly of a bone screw, the method comprising: loading a load ring from a bottom end of a receiver of the bone screw through a cavity thereof prior to the insertion of the shank head, wherein loading the load ring comprises twisting the load ring so that each of two opposing concave surfaces at a proximal surface of the load ring is aligned with an upwardly extending arm of the receiver and pushing the load ring proximally; inserting the shank head into the receiver from the bottom end thereof till access to a groove in an inner surface of the receiver at or near a distal end thereof is open; inserting a clip ring into the groove in the inner surface of the receiver; pushing the load ring and the shank head distally; and twisting the load ring in to a locked position so that each of the two concave surfaces at the top surface of the load ring is aligned with an opening of the rod channel of the receiver, wherein the load ring and the shank head is locked from distal movement.

In certain embodiments, disclosed herein is a bone screw comprising: a bone screw shank comprising a shank head; a receiver comprising a base having a cavity therewithin, the cavity configured to securely accept insertion of the shank head from a top of the receiver; a pair of arms extending upwardly from the base; and a rod channel defined between the pair of arms, wherein the base comprises a recess formed in a bottom surface thereof, wherein the base and the recess are shaped and sized to allow angulation in a range of about 0 degrees to about 60 degrees in a first lateral direction and prevent angulation of greater than about 0 degrees in a second lateral direction opposite the first lateral direction; and a load ring configured to be top-loaded into the receiver subsequent to the insertion of the shank head, wherein the load ring comprises a pair of legs connected by two concave surfaces at its proximal side. In some embodiments, the receiver comprises a pocket in connection with the cavity at a distal portion thereof, the pocket configured to receive the shank head and allow directional rotation therewithin. In some embodiments, the pocket comprises a pocket surface having at least part of a spherical surface that accommodates a spherical outer surface of the shank head. In some embodiments, the bone screw shank is configured to rotate about a transverse axis of the receiver in the first lateral direction before a rod is secured in the rod channel. In some embodiments, a maximal angulation between the bone screw shank and a longitudinal axis of the receiver is in a range of about 0 degrees to about 60 degrees. In some embodiments, a maximal angulation between the bone screw shank and a longitudinal axis of the receiver is greater than 55 degrees. In some embodiments, when a longitudinal axis of the receiver and a longitudinal axis of the bone screw shank are aligned, the bone screw is configured to allow derotation movement in the second lateral direction to aid capture of a rod. In some embodiments, when a longitudinal axis of the receiver and a longitudinal axis of the bone screw shank are aligned, the receiver is configured to provide a hard stop to rotational movement of the bone screw shank relative to the receiver in the second lateral direction without using a rod, a closure top, or any other locking element external to the bone screw. In some embodiments, the load ring comprises a top opening allowing access to the shank head from a top of the receiver. In some embodiments, the load ring comprises an inner surface and a distal portion of the inner surface accommodating a shape of at least part of the shank head. In some embodiments, the load ring comprises a plurality of fingers at its distal end, and wherein the plurality of fingers is configured to impart a frictional fit on the shank head. In some embodiments, the load ring comprises a distal recess at its distal end, the distal recess aligned with the recess of the receiver. In some embodiments, the distal recess is configured to aid angulation of the bone screw shank in the first lateral direction. In some embodiments, the angulation of the bone screw shank comprises movement in a medial to lateral direction (e.g., along D1) and/or movement in a cranial to caudal direction (e.g., along L3 axis). In some embodiments, the pair of arms comprises a first protrusion on an inner surface thereof, the first protrusion configured to prevent proximal translation of the load ring. In some embodiments, the pair of arms comprises a second protrusion on an inner surface thereof, the second protrusion configured to prevent distal translation of the load ring, the second protraction distal to the first protrusion. In some embodiments, at least part of the shank head extends beyond the distal portion of the inner surface of the load ring when the bone screw shank is rotated from the longitudinal axis of the receiver. In some embodiments, the receiver comprises a longitudinal axis extending through a bottom of the base toward a top of the pair of arms. In some embodiments, the receiver comprising a tool engagement groove at an outer surface of the pair of arms at or near a top thereof. In some embodiments, the cavity comprises at least two bottom edges that are substantially flat. In some embodiments, each of the at least two bottom edges are connected with a curved edge of the recess. In some embodiments, the shank head comprises a head diameter in a range from about 4.0 mm to about 8.0 mm. In some embodiments, the bone screw shank comprises a length from about 20 mm to about 120 mm. In some embodiments, the bone screw shank is configured to be rotatable about a longitudinal axis of the bone screw shank when the bone screw shank is rotated from a longitudinal axis of the receiver.

In certain embodiments, disclosed herein is a bone screw assembly comprising: a bone screw shank comprising a shank head; a receiver comprising a base having a cavity therewithin, the cavity configured to securely accept insertion of the shank head from a top of the receiver; a pair of arms extending upwardly from the base; and a rod channel defined between the pair of arms; a compression element configured to be top-loaded into the receiver subsequent to the insertion of the shank head, wherein the compression element comprises a pair of legs connected by two concave surfaces at its proximal side, and a lock screw configured to be top-loaded into the receiver thereby locking the shank head relative to the receiver. In some embodiments, the base comprises a recess formed in a bottom surface of the base, wherein the base is shaped and sized to allow angulation in a range of about 0 degrees to about 60 degrees in a first lateral direction. In some embodiments, the bone screw assembly comprises a favored angle screw that favors angulation in the first lateral direction. In some embodiments, the base is shaped and sized to prevent angulation of greater than about 0 degrees in a second lateral direction opposite to the first lateral direction. In some embodiments, the compression element or the receiver comprises a coaxial indicator configured to provide a feedback when a longitudinal axis of the bone screw shank is aligned with a longitudinal axis of the receiver. In some embodiments, the feedback is a tactile feedback. In some embodiments, the feedback is prevention of rotation in a second lateral direction. In some embodiments, the compression element is configured to be loaded with each of the pair of legs facing an opening of the rod channel. In some embodiments, the compression element is configured to be rotated so that each of the pair of legs faces one of the pair of arms subsequent to the loading, and then pushed distally into a secured position relative to the receiver. In some embodiments, the compression element is configured to be rotated when at a first location, wherein the first location is proximal to a second location where the compression element is in the secured position. In some embodiments, the compression element comprises a barb feature on each of the pair of legs, the barb feature configured to interact with a corresponding protrusion on an inner surface of each of the pair of arms thereby allowing distal insertion and preventing proximal movement of the compression element relative to the receiver. In some embodiments, the compression element comprises a through bore from a proximal end to a distal end thereof, the through bore configured to allow access of a drive tool to the bone screw shank. In some embodiments, the cavity is sized and shaped to prevent pulling off of the shank head from a bottom of the cavity. In some embodiments, the bone screw is a polyaxial screw. In some embodiments, the lock screw is a dual lock screw. In some embodiments, the dual lock screw comprises an outer element that couples with an inner surface of the pair of arms, and an inner element that is configured to be inserted within the outer element and couples with the outer element. In some embodiments, the outer element comprises a helical flange threadform that couples with a matching helical flange threadform on the inner surface of the pair of arms. In some embodiments, the outer element comprises an outer drive feature at or near a proximal end thereof, the outer drive feature configured to engage a driver tool. In some embodiments, the outer drive feature comprises a hexalobe at an inner surface of the outer element, the hexalobe extending distally but remaining proximal to a proximal end of the inner element. In some embodiments, the outer element comprises a protrusion located between the hexalobe and a matching inner threading configured to couple to the inner element. In some embodiments, the inner element comprises an inner drive feature, the inner drive feature configured to engage a second driver tool. In some embodiments, the inner drive feature comprises a second hexalobe at an inner surface of the inner element, the second hexalobe extending from at or near a distal end to at or near a proximal end of the inner element. In some embodiments, the inner element comprises an outer threading that couples to an inner threading of the outer element. In some embodiments, the dual lock screw is configured to provisionally lock the bone screw head relative to the receiver prior to inserting a rod in the rod channel of the bone screw assembly. In some embodiments, the lock screw is a single lock screw. In some embodiments, threadform that couples with a matching helical flange threadform on the inner surface of the pair of arms. In some embodiments, the single lock screw comprises a drive feature extending from at or near a proximal end to at or near a distal end thereof, the drive feature configured to engage a driver tool. In some embodiments, the single lock screw is configured to lock the shank head relative to the receiver when a rod is inserted in the rod channel of the bone screw assembly. In some embodiments, the receiver comprises a pocket in connection with the cavity at a distal portion thereof, the pocket configured to receive the shank head and allow directional or polyaxial rotation therewithin. In some embodiments, the pocket comprises a pocket surface having at least part of a spherical surface that accommodates a spherical outer surface of the shank head. In some embodiments, the bone screw shank is configured to rotate about a transverse axis of the receiver in the first lateral direction. In some embodiments, a maximal angulation of the shank head and a longitudinal axis of the receiver is greater than 55 degrees. In some embodiments, a maximal angulation of the shank head and a longitudinal axis of the receiver is in a range of about 0 degrees to about 60 degrees. In some embodiments, when a longitudinal axis of the receiver and a longitudinal axis of the bone screw shank are aligned, the bone screw is configured to allow derotation movement in the second lateral direction to aid for capture of a rod within the rod channel prior to derotation. In some embodiments, the compression element comprises an inner surface and a distal portion of the inner surface accommodating a shape of at least part of the shank head. In some embodiments, the compression element comprises a plurality of fingers at its distal end, and wherein the plurality of fingers is configured to impart a frictional fit on the shank head. In some embodiments, the compression element comprises a distal recess at its distal end, the distal recess aligned with the recess of the receiver when the compression element is in a secured position. In some embodiments, the distal recess is configured to aid angulation of the bone screw shank in the first lateral direction. In some embodiments, the angulation of the bone screw shank comprises movement in a medial to lateral direction (e.g., along D1) and/or movement in a cranial to caudal direction (e.g., along L3 axis). In some embodiments, at least part of the shank head extends beyond the distal portion of the inner surface of the compression element when the bone screw shank is rotated from the longitudinal axis of the receiver. In some embodiments, the receiver comprises a longitudinal axis extending through a bottom of the base toward a top of the pair of arms. In some embodiments, the receiver comprises a tool engagement groove at an outer surface of the pair of arms at or near a top thereof. In some embodiments, the shank head comprises a head diameter in a range from about 4.0 mm to about 8.0 mm. In some embodiments, the bone screw shank comprises a length from about 20 mm to about 120 mm. In some embodiments, a diameter or a maximal dimension of a cross section of the dual lock screw is in a range of about 5.5 mm to 6.0 mm. In some embodiments, a diameter or a maximal dimension of a cross section of the single lock screw is in a range of about 5.5 mm to 6.0 mm. In some embodiments, the rod channel is configured to receive a spinal rod therewithin, wherein the spinal rod comprises a non-circular cross section.

Overview

As disclosed herein, "bone screws" are interchangeable with or equivalent to "bone anchors," "fixation screws," and "pedicle screws." A "receiver" of the bone screw is interchangeable with or equivalent to a "tulip" herein. As disclosed herein, a bone screw "assembly" is interchangeable with or equivalent to a bone screw "construct." Disclosed herein, in some embodiments, are spinal fixation screws, bone anchors, bone screws, or use of the same.

As disclosed herein, "proximal direction" indicates the direction away from attachment of an element to the subject, while "distal direction" indicates the direction opposite proximal direction and toward attachment of an element to the subject.

As disclosed herein, "integral" to a bone screw may indicate the element is fixedly attached to the bone screw and does not allow rotational, translational, or perceivable deformable movement relative to the bone screw.

As disclosed herein, the "load ring" is interchangeable with or equivalent to a "compression element."

As disclosed herein, L2 and L3 axes are perpendicular to each other, and both axes are perpendicular to the longitudinal axis, L1, of the receiver of the bone screw. L3 axis is along the direction of extension of the rod channel in the receiver.

In some embodiments, the bone screws, spinal rods, rod to rod connectors or other devices are made of one or more of biocompatible materials including, but not limited to, titanium, stainless steel, cobalt chrome, ceramics and/or thermoplastic materials. In some embodiments, the bone screws disclosed herein are polyaxial. In some embodiments, the bone screw may favor angulation in one single direction, e.g., along a lateral direction. In some embodiments, the bone screw may favor angulation in a couple of direction that are not parallel to each other.

In some embodiments, the bone screws herein can be either preassembled or modular, e.g. parts of the bone screw may be assembled immediately pre-operatively or intraoperatively according to the needs of a specific user. The bone screws herein may be modular for ease of placement but can also be made as a preassembled variant.

Bone Screws with Fixed Lateral Rod

Disclosed herein, in some embodiments, are bone screws with a lateral rod. The lateral rod can be fixed or integral to the receiver of the bone screw. Such bone screws disclosed herein may include a bone screw shank comprising a shank head, a receiver having a base having a cavity therewithin, the cavity configured to securely receive the shank head, a pair of arms extending upwardly from the base, a rod channel defined between the pair of arms, and a lateral rod integral to or fixedly attached to the receiver and extends laterally away from the receiver.

Figure 2:
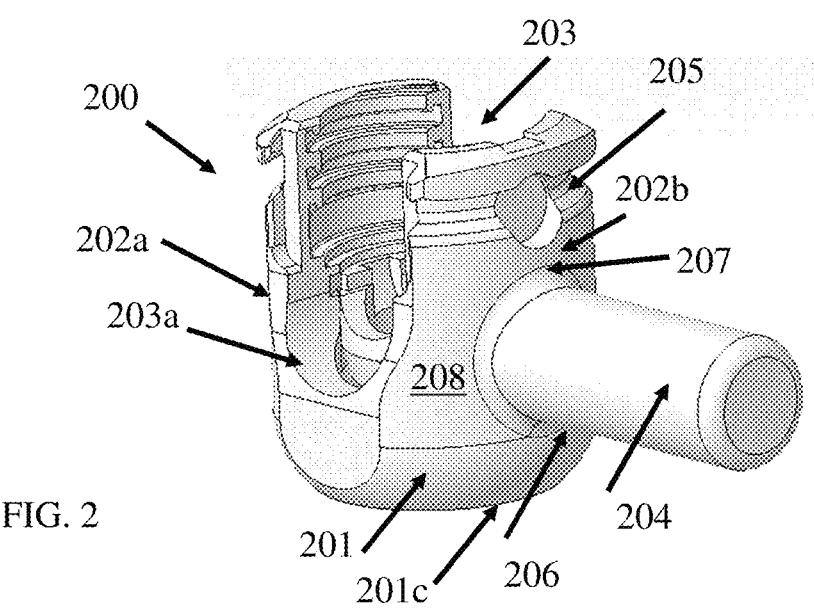
FIG. 2 shows an exemplary embodiment of the receiver of the bone screw in FIG. 1, in accordance with the embodiments herein.
Figure 3:
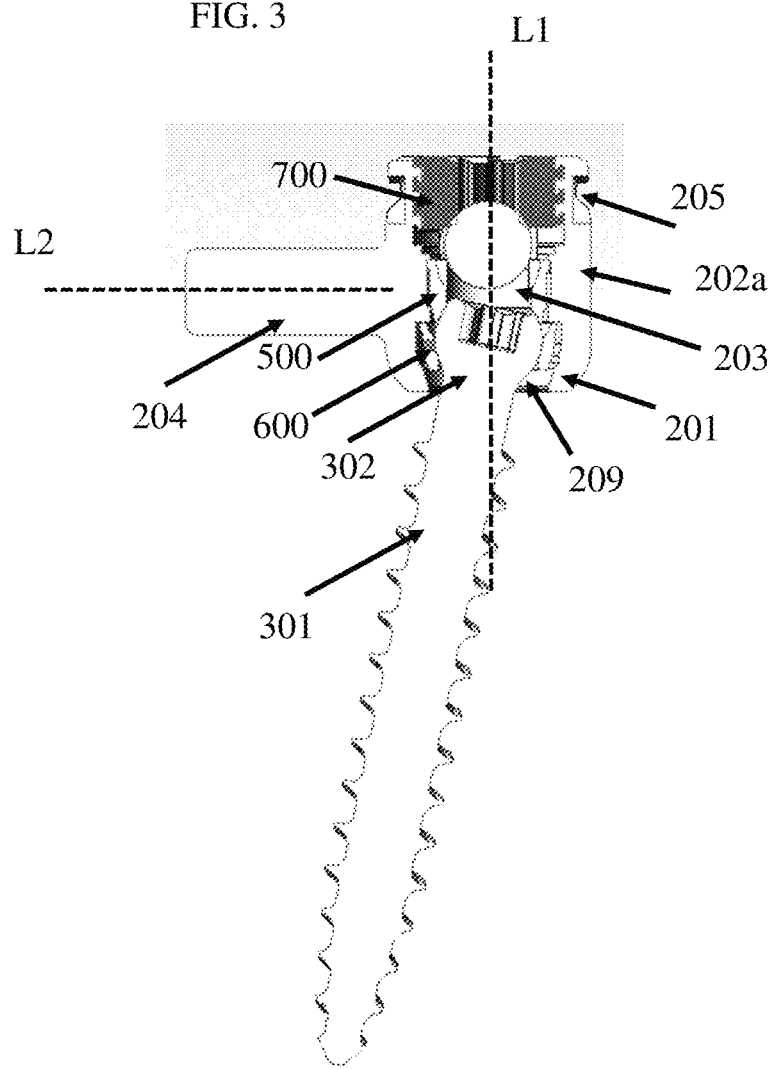
FIG. 3 shows an exemplary embodiment of a cross section from D-D' of the bone screw in FIGS. 1-2, in accordance with the embodiments herein.

FIGS. 1-3 show an exemplary embodiment of the bone screws with lateral rod in a perspective view (FIGS. 1-2) and cross-sectional view (FIG. 3) cutting from D-D' in FIG. 1. Referring to FIGS. 1-3, in this particular embodiment, the bone screw 100 includes a bone screw shank 300 that can be securely inserted into a receiver or a tulip 200. The bone screw shank 300 can include a shank head 302 and a shank body 301 that may be threaded for at least a portion thereof. The shank head can have a larger cross section that the shank body 301. The shank head may be bottom loaded through a cavity 209 located at a base 201 of the receiver 200. Alternatively, the shank head may be top-loaded into the receiver during assembly as disclosed herein in certain cases.

A pair of arms 202a, 202b can extend upwardly from the base, the pair of arms 202a, 202b may be positioned opposite to each other and may be positioned to define a rod channel 203 therebetween. The rod channel 203 can have two channel openings 203a, each channel opening determined by an edge of each of the pair of arms. The bone screw receiver includes a longitudinal axis, L1 that extends along the proximal to distal direction, as shown in FIG. 3. In some embodiments, the longitudinal axis, L1, of the receiver extends through a distal end or a bottom end of the base toward a proximal end or top end of the pair of arms 202a, 202b. The bone screw 100 can be a polyaxial screw. Alternatively, the bone screw 100 can be with a favored direction of angulation.

In some embodiments, the bone screw 100 may include a load ring 500, a lock ring 600, or both, that may be inserted into the bone screw and facilitate secured positioning and angulation of the bone screw shank 300 to the receiver 200. In some embodiments, the bone screw may include a closure top 700 that can be inserted from a top opening of the receiver connected to the rod channel 203. The closure top may be pressed against a spinal rod 400 thereby locking the shank head 302 relative to the receiver 200. Alternatively, the closure top 700, e.g., a lock screw, may be used to lock the shank head 302 to the receiver without presence of a spinal rod in the rod channel.

Continuing on referring to FIGS. 1-3, in this embodiment, the bone screw 100 includes a lateral rod 204 that is fixedly attached to or integral to the receiver 200. The lateral rod can extend substantially in a direction, e.g., L2 axis that is substantially perpendicular to the direction of extension of the rod channel, e.g., L3 axis.

In some embodiments, the lateral rod may be substantially straight, as shown in FIG. 1. In some embodiments, the lateral rod contains a curved portion, a bent portion, or a portion that is not substantially straight.

In some embodiments, the lateral rod may be extending along the L2 axis, as shown in FIG. 3. L2 axis is substantially parallel to the direction of extension of the rod channel 303, e.g., L3 axis. In some embodiments, the lateral rod may be tilted away from the L2 axis for an acute angle, e.g., about 10-20 degrees, but remain perpendicular to L1 axis. In some embodiments, the lateral rod may be tilted away from the L3 axis for an acute angle, but remain perpendicular to L1 axis. In some embodiments, the direction along which the lateral rod is extending may be in the plane determined by L2 and L3 axes, so that the direction of extension of the lateral rod remains substantially perpendicular to the L1 axis.

In some embodiments, the direction along which the lateral rod is extending may be in the plane determined by L1 and L2 axes, thus it remains perpendicular to L3 axis instead. In some embodiments, the lateral rod may be tilted away for different acute angle(s) from any one, two, or three of the L1, L2, and L3 axes dependent on the need of the spinal applications.

In some cases, the lateral rod 204 extends laterally from an outer surface 208 of one of the arms, e.g., 202b, of the receiver 200. In some embodiments, the outer surface 208 can be partly or entirely on the arm 202b. The outer surface may be partly or entirely on the base 201. The lateral rod 204 may comprise a cross-sectional shape that is identical to that of a spinal rod 400 that is configured to be received in the rod channel 203 of the bone screw. In this particular embodiment, the lateral rod 204 comprises a substantially cylindrical shape. In this embodiment, the lateral rod 204 includes a circular cross section perpendicular to L2. In some embodiments, the lateral rod may comprise a non-circular cross section including but not limited to the non-circular cross sections disclosed herein, perpendicular to L2. The lateral rod may include a length that can be customized. For example, the lateral rod may include a length in a range of about 1 cm to about 20 cm.

Figure 4:
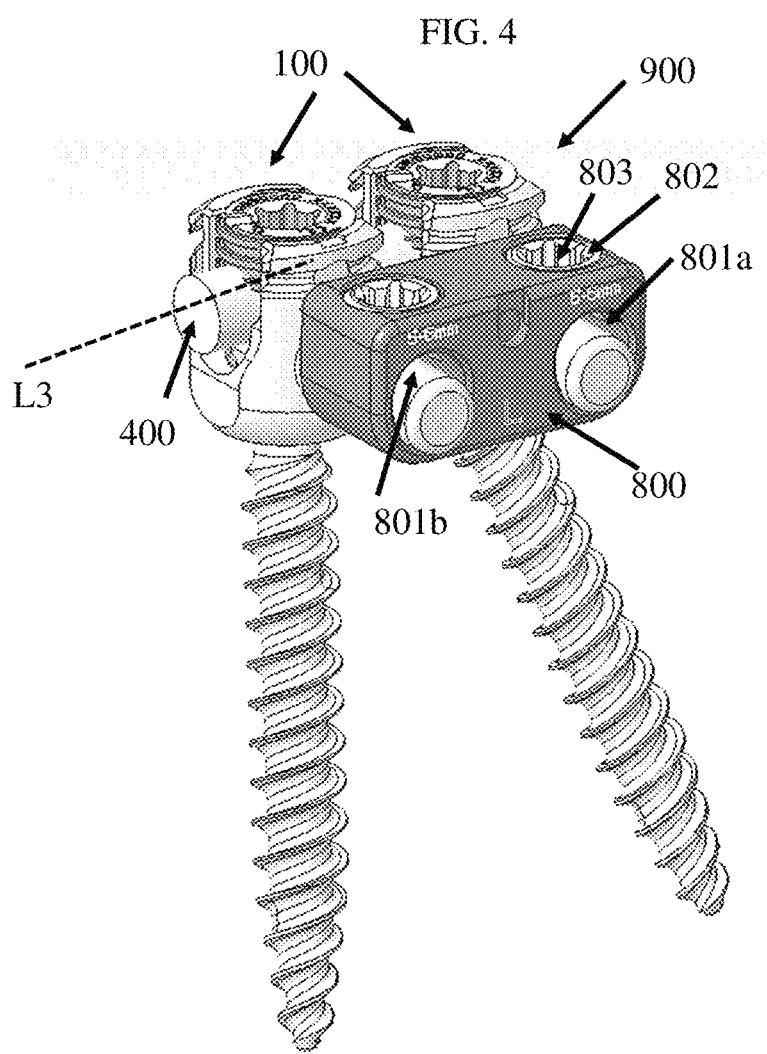
FIG. 4 shows an exemplary embodiment of a bone screw assembly including two bone screws in FIGS. 1-3 in a perspective view, in accordance with embodiments herein.
Figure 5:
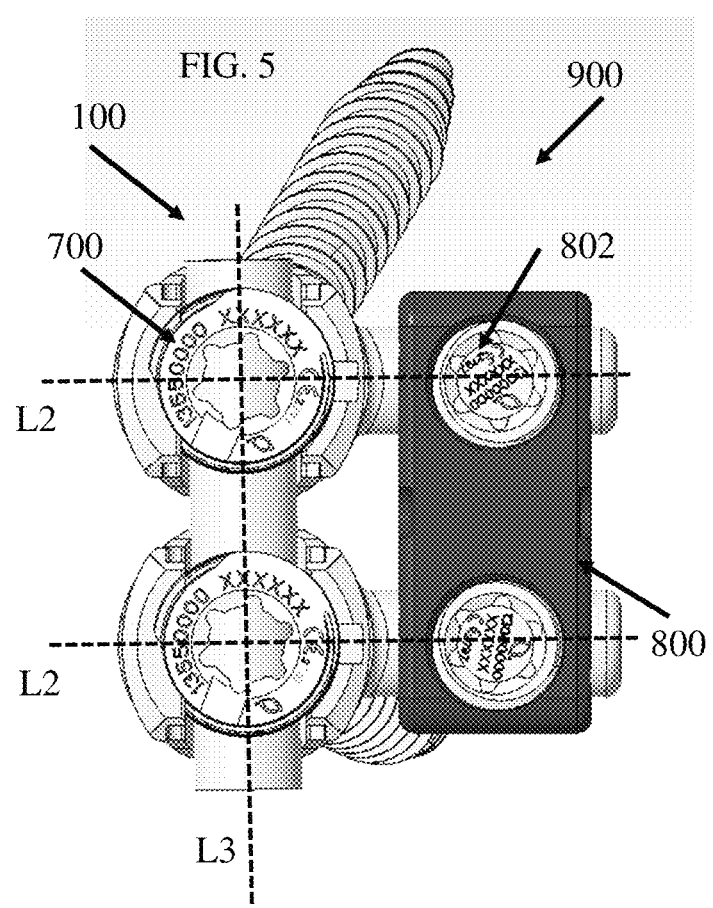
FIG. 5 shows an exemplary embodiment of the bone screw assembly in FIG. 4 in a top view, in accordance with embodiments herein.

In some embodiments, the lateral rod 204 includes a size that can be received in a rod to rod connector 800. FIGS. 4-5 show an exemplary embodiment of two bone screws 100 that are connected together into an assembly 900 with a spinal rod 400 extending in a first direction, L3 axis, through the rod channel of each of the bone screws. FIG. 4 shows a perspective view of the assembly 800, and FIG. 5 shows a top view of the assembly. In this embodiment, a rod to rod connector 800 can securely receive the first lateral rod 204 in a first bore 801*a* and the second lateral rod in a second bore 801*b* of the rod to rod connector 800. The first bore and the second bore of the rod to rod connector can be substantially parallel to each other.

In some embodiments, the first bone screw is anchored to a first vertebral bone, and the second bone screw is anchored to a second vertebral bone. In some embodiments, the first bone screw or the second bone screw is a poly-axial screw. The rod to rod connector 800 can comprises a first opening 803 at a top thereof, the first opening connected to the first bore and the first opening is configured to receive a closure top 802 that can press against the first lateral rod thereby securing the first lateral rod to the rod to rod connector 800. Similarly, the rod to rod connector can have a second opening 803 at a top thereof, the second opening connected to the second bore 801*b*. In some embodiments, the rod to rod connector may include more than two bores that can be used to include more than two lateral rods of bone screws or a combination of lateral rod(s) 204 of bone screws and conventional spinal rods 400.

In some embodiments, the receiver 200 includes a tool engagement groove 205 at an outer surface of the pair of arms 202*a*, 202*b* at or near a top end thereof, and wherein a top edge of the lateral rod 207 is distal to the tool engagement groove. In some embodiments, a bottom edge 206 of the lateral rod is proximal to a distal end 201*c* of the base.

In some embodiments, the bone screws 100 disclosed herein have a protruding rod portion or a lateral rod 204 off the tulip or receiver 200 on the medial or lateral side to allow for connection with other devices, e.g., with existing rod to rod connectors 800. In some embodiments, two bone screws placed adjacent to each other can be coupled using a "H" style rod to rod connector, e.g., in FIGS. 4-5. For example, the two bone screws may be anchored on two different vertebrae on adjacent vertebral levels. This may advantageously allow for the two bone screws on each side of two adjacent fixated levels to be coupled, making the segment a solid construct, thereby minimizing or eliminating relative movements between the two levels along the cranial to caudal direction (e.g., along L3 axis) and/or along other directions. Once the lateral rods 204 between the adjacent bone screws are coupled using a rod-rod connector 800, the tulip or receiver 200 of the bone screws can still accept a spinal rod 400 in order to be tied into the long construct. Once the desired vertebral levels, for example levels above and below a pedicle subtraction osteotomy (PSO) or unstable junction between adjacent levels caused by osteotomies, revision, corpectomy in trauma or tumor, or resection, are secured to one another using the implant and rod to rod connectors, then a spinal rod 400 can be placed bilaterally and used as template to further control or assist the relative kyphosis or lordosis between the two levels without causing rotation or slipping between the two unstable levels in order to prevent damage to the spinal cord/caudal equina. The two converging bone screws and connectors together may create a stronger segment across the unstable bodies to allow for correction and safety during sagittal and corona alignment during correction of a complex deformity.

In some embodiments, this bone screw design advantageously allows for the coupling of two adjacent level pedicle screws on the same side of a construct using rod-rod connections, e.g., left or right side of the construct. The implant can allow two levels to be coupled to minimize or eliminate vertical translation, e.g., along L3 axis, along caudal to cranial direction but may provide freedom in varying lordosis kyphosis as well as some degree of medial or lateral angulation. The coupled bone screws can still be connected to other bone screws or bone screw assemblies using connection to the same spinal rod 400. The bone screws 200 or bone screw assemblies 900 may give flexibility in building constructs for complex deformity and trauma applications where connection(s) to a spinal rod may be needed. The implant may take the place of using multiple satellite rods or rod-rod connectors along with pedicle screws and allow the ability to tie-in a PSO level to the entire implant construct or a spinal rod.

Dual-Head Screw Connectors

Figures 7, 8:
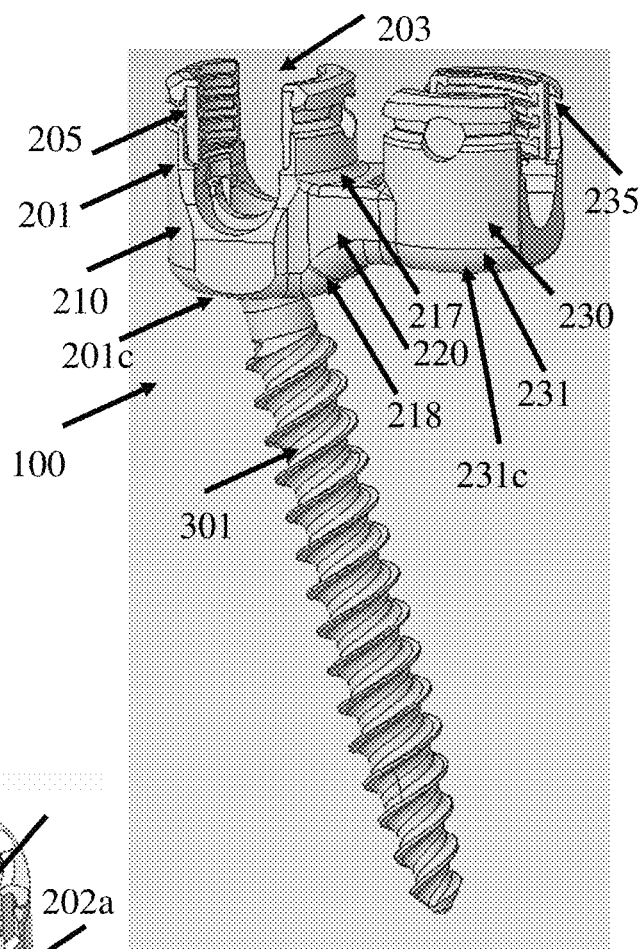
FIGS. 7-8 show exemplary embodiments of a dual-head bone screw in different views, in accordance with embodiments herein.
Figure 9:
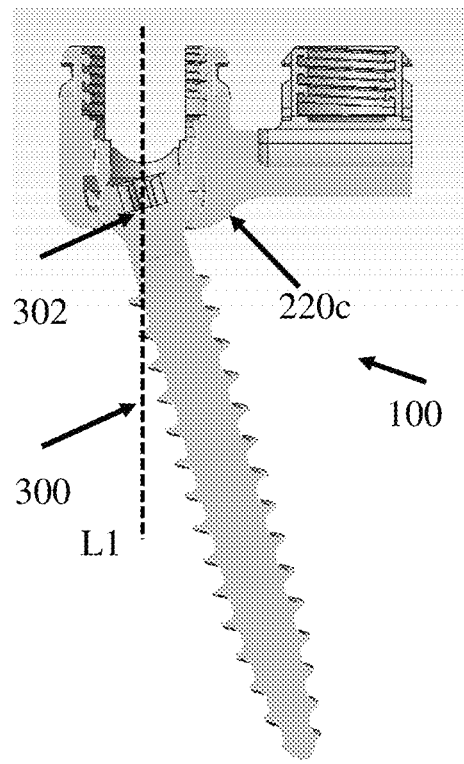
FIG. 9 shows a cross section view of the dual-head bone screw in FIGS. 7-8, in accordance with embodiments herein.

Disclosed herein, in some embodiments are bone screws with a dual-head. Referring to FIGS. 7-9, in a particular embodiment, the bone screw 100 includes a single bone screw shank 300 having a shank head 302 and a shank body 301. The dual-head receiver 200 may include a first receiver 200 with a first base 201 having a cavity 209 therewithin. The cavity can be configured to securely receive the shank head 302. The first receiver can include a first pair of arms 202*a*, 202*b* extending upwardly from the first base. The bone screw may include a first rod channel 203 defined between the first pair of arms. The bone screw 100 may also include a second receiver 230 with a second base 231 having a second rod channel 233 defined between a second pair of arms 232*a*, 232*b*. There can be a connection 220 between the first receiver 200 and the second receiver 230. The connection can be integral to the first and second receivers or movable relative to the first or the second receiver. In some embodiments, the first rod channel 203 extends in a first direction, L3, and the second rod channel 233 extends in a second direction, L2, substantially perpendicular to the first direction. In some embodiments, at least part of the first pair of arms 202*a*, 202*b* face an opening of the second channel 233 while at least part of the second pair of arms 232*a*, 232*b* face an opening of the first channel 203. In some cases, a bottom 231*c* of the second base is proximal to a bottom surface of the first base 201*c*.

Continuing referring to FIGS. 7-9, in the same embodiment, the first receiver 200 comprises a longitudinal axis L1 extending in a proximal to distal direction, and wherein the connection 220 between the first receiver and the second receiver extends in a different direction along L2 axis. The L2 axis may be substantially perpendicular to the longitudinal axis of the first receiver, L1. The connection 220 between the first receiver and the second receiver can extend laterally from an outer surface of one of the first pair of arms 202*b*. In the same embodiment, the connection between the first receiver and the second receiver may extend laterally from an outer surface of an opening of the second rod channel 233*b*. In some embodiments, the first rod channel 203 and the second rod channel 233 comprise an identical size, shape, or both. In alternative embodiments, the first rod channel and the second rod channel have a different size or shape.

Figure 39A:
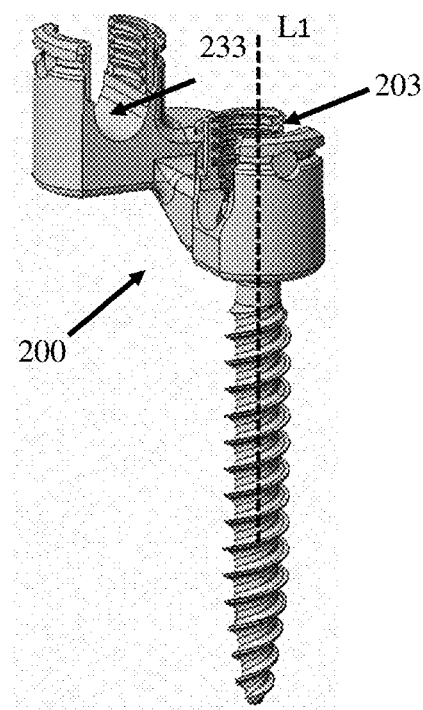
FIG. 39A shows an exemplary embodiment of the dual-head bone screws disclosed herein; in this case, a perspective view of the dual-head bone screws with two spinal rod channels at different levels along the proximal to distal direction.
Figure 39B:
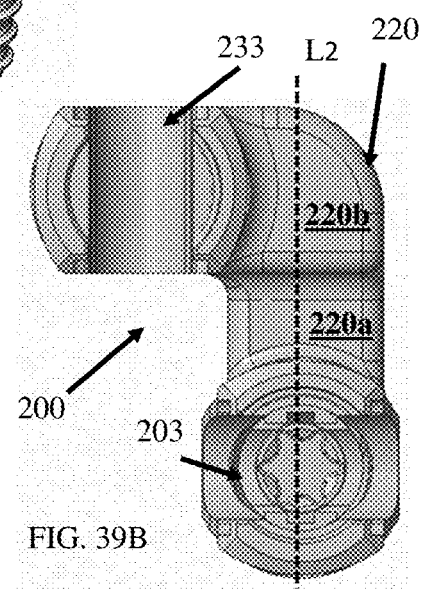
FIG. 39B shows an exemplary embodiment of the dual-head bone screws disclosed herein; in this case, a top view of the dual-head bone screw in FIG. 39A with a connection that includes a curved portion.

In some embodiments, the connection 220 may be substantially straight and extending along L2 axis. L2 axis can be substantially to the direction of extension of one of the rod channels, 203, 233, e.g., L3. In some embodiments, the connection 220 may not be substantially straight. For example, the connection may include a curved portion or a bend portion. Referring to FIGS. 39A-39B, in a particular embodiment, the connection 220 may include a portion that is substantially straight and extending along L2 axis, 220a. In the same embodiment, the connection 220 may also include a curved portion, 220b, connecting the straight portion and the second receiver 230.

In some embodiments, the connection 220 may be extending along the L2 axis. In some embodiments, the connection may be extending in a direction that is tilted from L2 axis. The connection may also be configured to include a different thickness along L2 axis so that the first rod channel 203 and the second rod channel 233 may be at two different levels along the L1 axis. In this particular case, the second rod channel is proximal to the first rod channel as shown in FIG. 39A.

In some embodiments, the first receiver 200 has a first tool engagement groove 205 at an outer surface of the first pair of arms at or near a top surface thereof, and wherein a top edge of the connection 217 between the first receiver and the second receiver is distal to the first tool engagement groove 205. The second receiver 230 can include a second tool engagement groove 235 at an outer surface of the second pair of arms at or near a top surface thereof, and wherein a top edge 217 of the connection between the first receiver and the second receiver is distal to the second tool engagement groove 235.

In some embodiments, a bottom surface 218 of the connection 220 between the first receiver and the second receiver is proximal to a bottom of the first base 201c.

In some embodiments, the first receiver is configured to receive a first closure top 700 that presses against a first rod 400 within the first rod channel 203 thereby securing the first rod 400 therewithin. The second receiver 230 can be configured to receive a second closure top 700 that presses against a second rod within the second rod channel 233 thereby securing the second rod therewithin.

In the same embodiments, the first receiver 200 may comprise a U-shape opening 203b defined by at least part of an edge of each of the first pair of arms 202a, 202b. Similarly, the second receiver 230 comprises a U-shape opening 233b defined by at least part of an edge of each of the second pair of arms. In some embodiments, the connector 220 is narrower than the first receiver 200 along the L3 axis. The second receiver 230 is shorter than the first receiver 200 along a proximal to distal direction, L1. Referring to FIG. 8, in the same embodiment, the second rod channel 233 extends laterally beyond an edge of each of the second pair of arms 232a, 232b. In this specific embodiment, the second rod channel 233 extends laterally beyond a lateral edge of the second receiver 230.

In some embodiments, the bone screw 100 is polyaxial. In some embodiments, the bone screw may favor angulation in one or more directions, e.g., along a lateral direction.

In some embodiments, the second receiver 230 may or may not include a cavity that is configured to receive a bone screw shank therein.

As can been seen in FIG. 8, the second rod channel 233 comprises a half-moon opening at a lateral edge of the second receiver 230.

Figure 10:
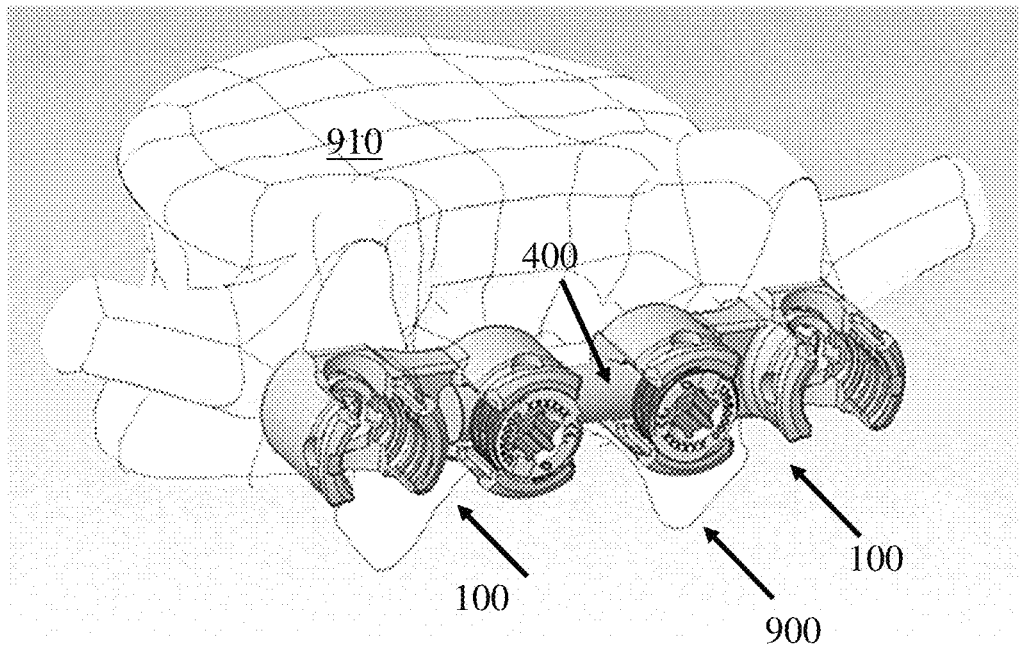
FIG. 10 shows an exemplary embodiment of a bone screw assembly containing two dual-head bone screws in FIGS. 7-9 in a perspective view, in accordance with embodiments herein.
Figure 11:
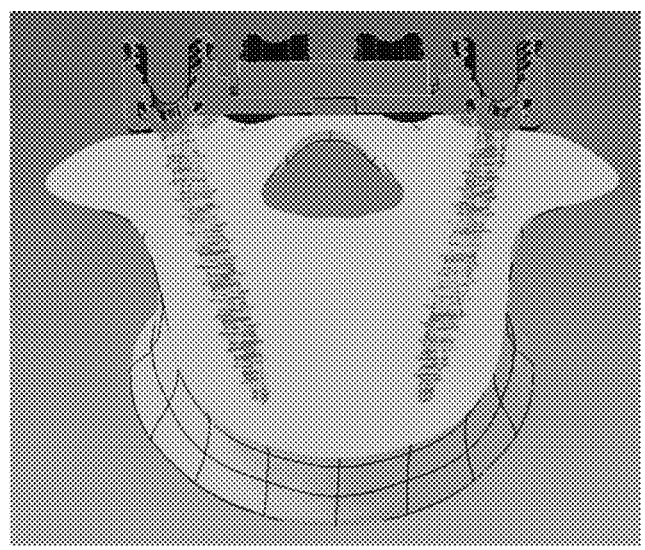
FIG. 11 shows an exemplary embodiment of a bone screw assembly containing two dual-head bone screws in FIGS. 7-9 in a cross-sectional view, in accordance with embodiments herein.

In some embodiments, the dual head bone screw 100 may be connected to another bone screw 200, either conventional or dual head screw, to form a bone screw construct or assembly. Referring to FIGS. 10-11, in a particular embodiment, two dual head bone screw 100 are connected using a spinal rod 400, into a bone screw assembly 900. In this embodiment, the bone screw assembly may have a first bone screw 100 as shown in FIGS. 7-9. This first bone screw may include a first dual-head receiver 200. In addition to the first bone screw, the assembly 900 may also include a second bone screw 100 as shown in FIGS. 7-9, and similar to the first bone screw. The first bone screw and the second bone screw may be anchored to a vertebral body 910 at an identical level but at two different lateral sides of the medial line of the vertebra. FIG. 10 shows a perspective view of an exemplary embodiment of the bone screw assembly 900, and FIG. 11 shows a cross-sectional view of the exemplary embodiment of the bone screw assembly 900. The spinal rod 400 connecting the two dual head bone screws 100 may be extending substantially lateral, along L2 axis. In some embodiments, the spinal rod may have a length along L2 that can be customized to fit in the rod channel 233 of each of the both bone screws 100.

In some cases, the dual head screw 100, when implanted in the patient, has one rod channel that can be running vertical and in the plane determined by cranial to caudal (e.g., along L3 axis) and left to right directions while the other is running orthogonal to the first rod slot, e.g., horizontal, as shown in FIGS. 10-11. This can allow a horizontal rod 400 to be placed across a vertebral body or segment between the two bilateral dual headed screws 100. Once the horizontal rod 400 is locked between the two screws 100, the shank heads 302 of the screws can still rotate in the cranial to caudal direction.

In some embodiments, the bone screw assembly 900 may run a diagonal crossing rod across two adjacent vertebral levels to secure torsional resistance but the goal may be to connect screws at the same level. Once the levels above and below the PSO or unstable junction caused by osteotomies, revision, resection, or a combination thereof are secured with crossing rods, then a rod can be placed bilaterally and used as template to control or assist compression of the two levels together without causing rotation or slipping between the two unstable levels in order to prevent damage to the spinal cord/caudal equina. The two converging screws and a rod spanning the median distance between them may create a triangle that is rigid to torsion and medial/lateral splay but allows for rotation in the cranial to caudal direction (e.g., along L3 axis).

The dual headed screw may allow for dual rod connections from one placed pedicle screw shank in order to give improved flexibility in building constructs for complex deformity and trauma applications where connection to both the longitudinal rod, e.g., along L3 axis, and lateral rod, e.g., along L2 axis, may be needed. The single dual head connector may take the place of using multiple rod to rod connectors along with pedicle screws and allows the ability to tie-in a PSO level to the entire construct or longitudinal rod.

In some embodiments, the dual head bone screws disclosed herein may include two rod channels that are substantially parallel to each other.

Figure 12:
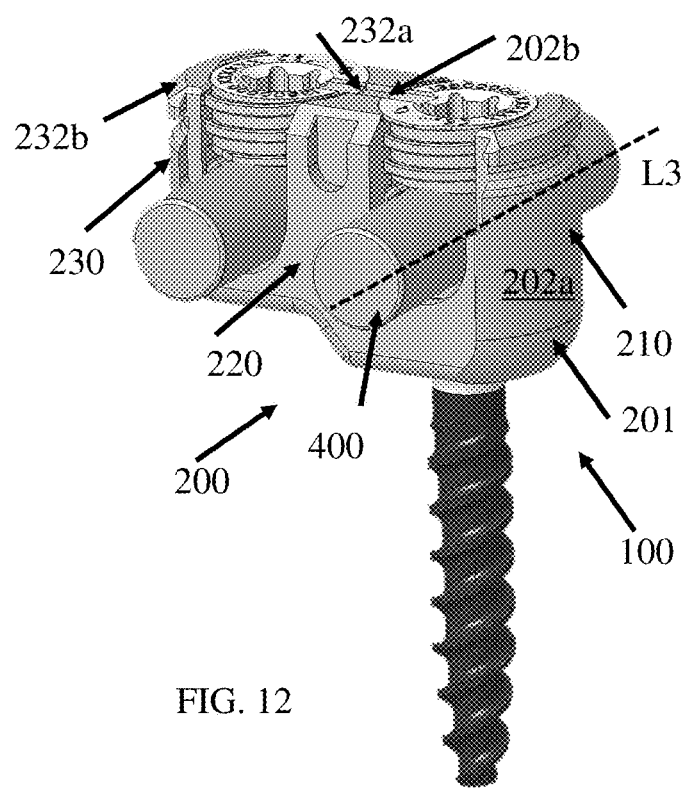
FIG. 12 shows an exemplary embodiment of a dual-head bone screw, in accordance with embodiments herein.
Figure 13:
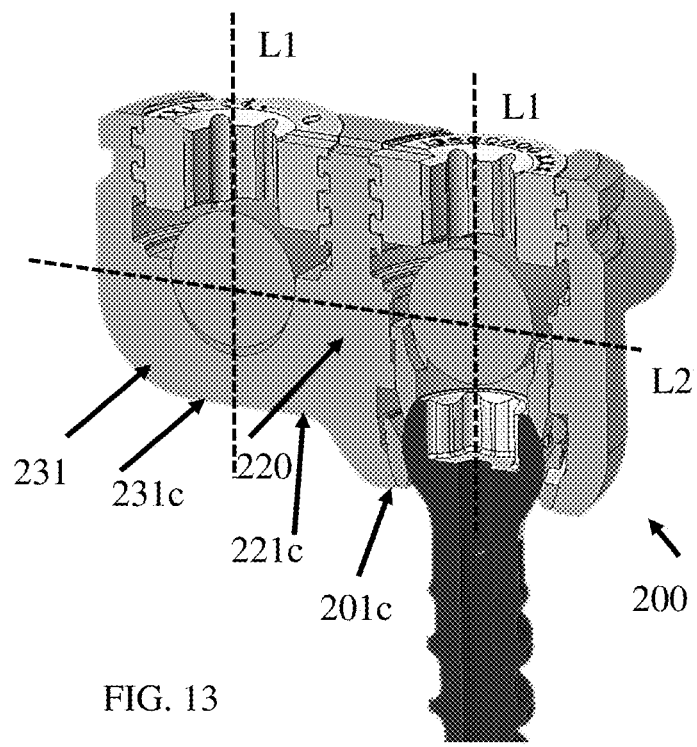
FIG. 13 shows a cross section of the dual-head bone screw in FIG. 12, in accordance with embodiments herein.
Figure 14:
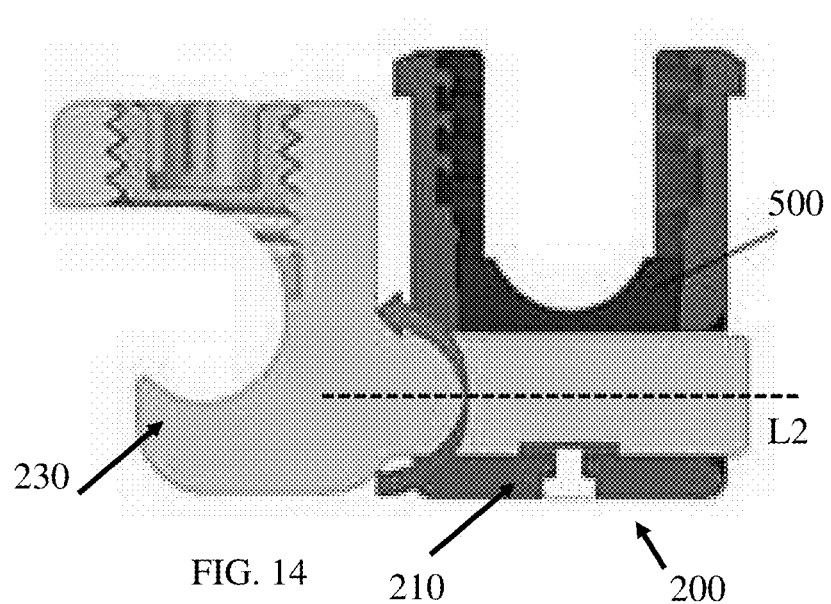
FIG. 14 shows an exemplary embodiment of a receiver of a dual-head bone screw disclosed herein, in accordance with embodiments herein.

Referring to FIGS. 12-14, in a particular embodiment, the dual head bone screw 100 includes similar structural elements to the bone screw shown in FIGS. 7-9, except that the rod channels are substantially parallel to each other.

In this particular embodiment, the bone screw 100 comprises a bone screw shank 300 comprising a shank head 302, a dual-head receiver 200 having a first receiver 210 comprising a first base 201 having a cavity 209 therewithin, a first pair of arms 202a, 202b extending upwardly from the first base 201, a first rod channel 203 defined between the first pair of arms. The bone screw also may include a second receiver 230 comprising a second base 231 having a second rod channel 233 defined between a second pair of arms 232a, 232b; and a connection 220 between the first receiver and the second receiver, the connection integral to the first and second receivers, or movable relative to one or both of the receivers. In some embodiments, the connection 220 may be formed by one of the first pair of arms 201b and one of the second pair of arms 232a. In this particular embodiment, the first rod channel 203 extends in a first direction, e.g., along L3 axis, and the second rod channel extends in a second direction substantially parallel to the first direction, e.g., also along L3 axis. In the same embodiment, the first pair of arms 202a, 202b, faces the second pair of arms 232a, 232b.

In some embodiments, the first and second rod channels are extending in two directions that are tilted by an acute angle from each other. As an example, the first channel can be extending along L3 axis, and the second rod channel extending in a direction that is tilted by 15 degrees from L3 axis, but both directions are still perpendicular to L1 axis. In some embodiments, one or both of the rod channels, 203 and 233 may extend in a direction that is tilted from one or more of the L1, L2, L3 axes, and the three axes shown in FIGS. 12-13.

Figure 40A:
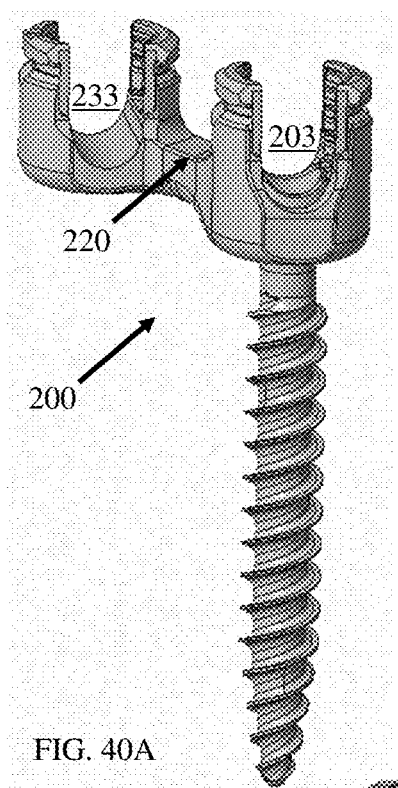
FIG. 40A shows an exemplary embodiment of the dual-head bone screws disclosed herein; in this case, a perspective view of the dual-head bone screws with two spinal rod channels that extend in directions that are substantially parallel to each other.
Figure 40B:
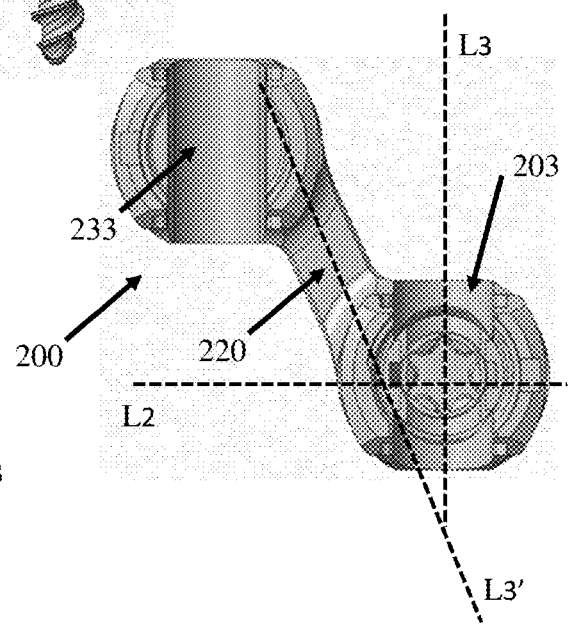
FIG. 40B shows an exemplary embodiment of the dual-head bone screw shown in FIG. 40A; in this case, a top view of the dual-head bone screws with a connection that extends in a direction that is titled from a direction of extension of the first rod channel or the second rod channel.
Figures 41A, 41B:
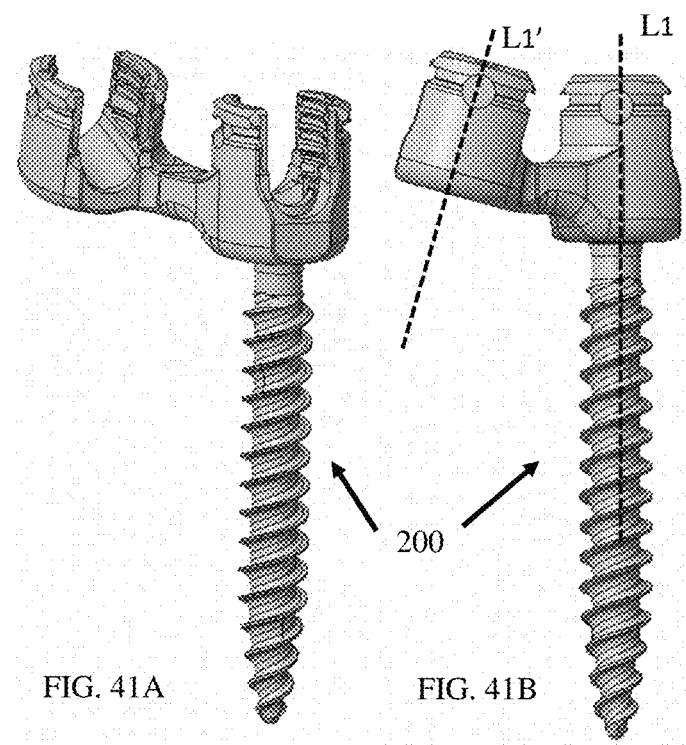
FIGS. 41A-41B show exemplary embodiments of the dual-head bone screws disclosed herein; in this case, a perspective view (FIG. 41A) and side view (FIG. 41B) of the dual-head bone screws with the longitudinal axes of the two receivers form an acute angle therebetween.
Figure 41C:
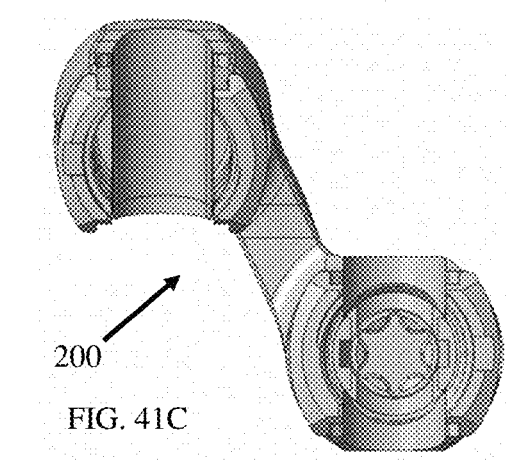
FIG. 41C shows an exemplary embodiment of the dual-head bone screws disclosed herein; a top view of the dual-head bone screws with a connection that extends in a direction that is titled from a direction of extension of the first rod channel or the second rod channel.

In some embodiments, the connection 220 may be substantially straight and extending in a direction perpendicular to L3, e.g., along L2 axis as in FIGS. 11-12. In some embodiments, the connection 220 may not be substantially straight. For example, the connection may include a curved portion or a bend portion. In some embodiments, the connection 220 may be extending along the L2 axis. In some embodiments, the connection may be extending in a direction that is tilted from L2 axis or L3 axis, e.g., L3' axis. Referring to FIGS. 40A-40B, the connection 220 may be extending in a direction that is within a plane determined by L3 and L2 axes, thus it may remain perpendicular to L1. The angle between the L3 and L3' axes may be acute, for example, it may be within a range from about 5 degrees to about 40 degrees. In some embodiments, the angle between the L3 and L3' axes may be within a range of about 15 degrees to about 30 degrees. In some embodiments, the connection may be extending in a direction that is tilted from one or more of the L1, L2, and L3 axes.

The connection may also be configured to include a different thickness at different portions thereof, the thickness can be along L1 axis. The thickness of the connection may not be uniform so that the first rod channel 203 and the second rod channel 233 may be at two different levels along the L1 axis. In this particular case, the second rod channel is positioned proximal to the first rod channel as shown in FIG. 39A.

In some embodiments, a bottom surface 231c of the second base is proximal to a bottom surface of the first base 201c. In this embodiment, the connection 220 between the first receiver and the second receiver extends substantially perpendicular to the longitudinal axis, L1, of the first receiver or the second receiver. In some embodiment, the connection 220 extends along L2. The connection 220 between the first receiver and the second receiver may extend laterally from an outer surface of one of the first pair of arms 201b on one side and from an outer surface of one of the second pair of arms 232a on the other side. In some embodiments, the connection may extend laterally from an outer surface of the first base 201 to an outer surface of the second base 231. The two rod channels, 203, 233 can comprise an identical size or shape. A bottom surface of the connection 221c can be proximal to a bottom surface 201c of the first base, a bottom surface of the second base 231c, or both. The first receiver 210 may include a proximal or top opening that is configured to receive a first closure top 700 that presses against a first rod 400 within the first rod channel 203 thereby securing the first rod therewithin, and the second receiver may have a second proximal opening that is configured to receive a second closure top 700 that presses against a second rod 400 within the second rod channel 233 thereby securing the second rod therewithin. In some embodiments, the first receiver 210 comprises a U-shape opening 203a defined by at least part of an edge of each of the first pair of arms 202a, 202b, and the second receiver 230 comprises a U-shape opening 233b defined by at least part of an edge of each of the second pair of arms 232a, 232b. The second receiver can be shorter than the first receiver along a proximal to distal direction, e.g., L1 axis. In some embodiments, the first rod channel and the second rod channel are at an identical level along a proximal to distal direction, L1. The bone screws can be polyaxial or with favored angulation in one or more directions.

In some embodiments, the dual head bone screw 100 with parallel rod channels may be connected with another bone screw, e.g., a dual head bone screw, any other bone screw disclosed herein, or any traditional bone screw, to form a bone screw assembly.

In some embodiments, the dual head bone screw 100 may include two rod channels 203, 233 that are not parallel to each other. In some embodiments, the dual head bone screw may include a second rod channel 233 that may be translatable or rotatable relative to the first rod channel 203 in different directions. As a non-limiting example, the connection between the first and the second receiver can be rotatablely connected to the first receiver and can be rotated so that the second rod channel may become side-loading as shown in FIG. 14. In this particular embodiment, the first receiver and the second receiver are not fixedly connected or integral to each other, and include a connection that can be rotatable about L2 axis and/or translatable along L2 axis. The second receiver 230 can be rotated for loading a spinal rod from its side. The second receiver can include a rod channel that is parallel to the first rod channel before any movement, and may still be parallel to the first rod channel after movement as shown in FIG. 14.

Referring to FIGS. 19A-19D, in some embodiments, the connection 220 may be integral to one of the first receiver 210 and the second receiver 230, but rotatable and/or translatable to the other one of the first and second receivers. In these particular embodiments, the connection may be integral to the first receiver 210, but the second receiver is movable relative to the connection 220 and the first receiver. As a result, the second receiver 230 may be rotatable about the L2 axis from the position shown in FIG. 12, to a rotated position as shown in FIG. 19C. For instances, the second receiver 230 can be rotated about the L1 axis from the position shown in FIG. 12 to the position shown in FIG. 19D. FIG. 19B shows a side view of the dual-head bone screw in FIG. 19C where the second receiver is rotated away for an acute angle from L1 axis. In some embodiments, the connection 220 may also enable translation of the second receiver relative to the first receiver to optimize the distance between the first and second rod channels.

In some embodiments, one of the first and second rod channels 203, 233, may be rotated one or more of L1, L2, and L3 axes. As an example, the first channel can be extending along L3 axis, and the second rod channel extending in a direction that is tilted by 15 degrees from L3 axis, but both directions are still perpendicular to L1 axis. In some embodiments, one or both of the rod channels, 203 and 233 may extend in a direction that is tilted from one or more of the L1, L2, L3 axes, and the three axes are shown in FIGS. 19A-19D.

In some embodiments, the dual head screws with parallel rod channels can be advantageously used to allow for a medial and lateral rod to be placed next to one another in a construct or assembly having multiple rods, e.g., three or four rods. In some embodiments, the dual head screws with parallel rod channels may advantageously provide an improvement over traditional rod to rod connectors and pedicle screws where one head is a pedicle screw with an open or closed tulip or receiver to capture one rod and the other head medially or laterally away from the first head is a tulip that can be either open, closed, or side loading. The two rod connections, or the two bone screw heads can either be fixed to one another or translatable, or rotatable relative to one another. The dual head bone screws disclosed herein and their assemblies may replace the traditional need to have both a pedicle screws and a rod to rod connector at each level when placing satellite rods.

Spinal Rods

Disclosed herein, in some embodiments, are spinal rods that fit into rod channels of the bone screws disclosed herein, connectors, or any other existing fixation devices. The spinal rods herein may include an elongate body with a non-circular cross section.

Figure 15A:
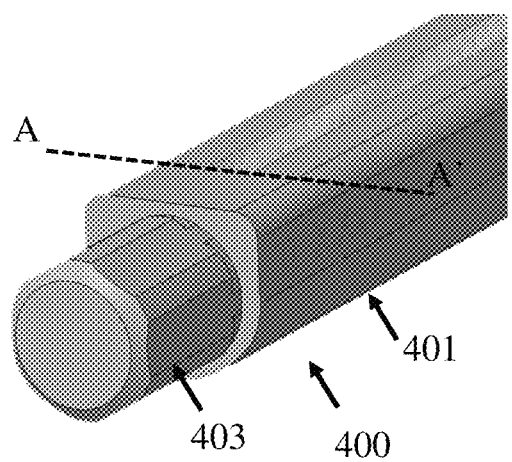
FIGS. 15A-15H show exemplary embodiment of the spinal rod with a non-circular cross section, in accordance with embodiments herein.
Figure 15B:
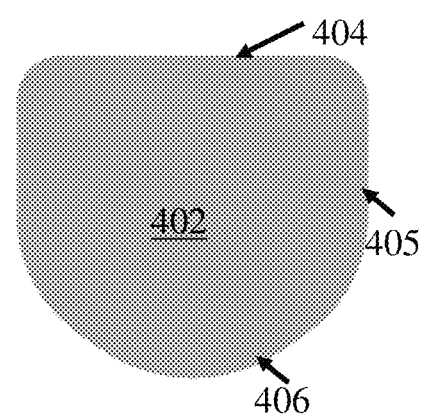
Figure 15C:
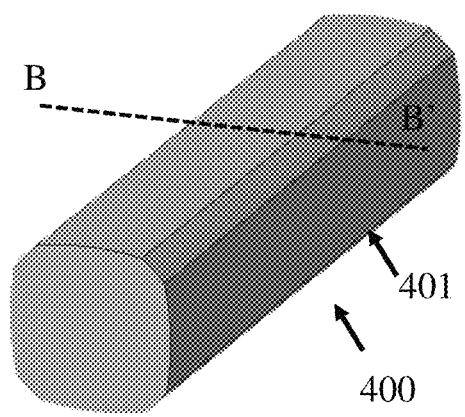

Referring to FIGS. 15A-15H, in some embodiments, the spinal rod 400 may include an elongate body 401 with a non-circular cross section 402 that is perpendicular to the elongate body. The cross section in FIG. 15B can be obtained by cutting along A-A' as shown in FIG. 15A. The cross section in FIG. 15D can be obtained by cutting along B-B' as shown in FIG. 15C. The spinal rods 400 disclosed herein may be shaped and sized so that they can be inserted into a spinal rod channel of a bone screw receiver, e.g., 200, a rod to rod connector 800, or other spinal fixation devices. In some embodiments, the spinal rods disclosed herein are configured to be secured within the spinal rod channel 203 or a bore 801a, 801b, by a closure top 700 pressing against the elongate body.

In some embodiments, the non-circular cross section 401 may include different shapes and/or sizes. FIGS. 15B, 15D, 15F, and 15H show exemplary embodiments of the non-circular cross sections. As shown in FIG. 15B, the cross section 401 may comprise a flat top edge 404, two flat side edges 405, and a curved V-shaped bottom edge 406. The cross section may also include curved corners. The curved corners may connect two adjacent edges of the cross section.

The spinal rod may include a protrusion 403 extending from an end surface of the elongate body 401, the protrusion integral to the elongate body. The protrusion can have a second non-circular cross section that is smaller than the non-circular cross section of the elongate body. The second non-circular cross section may or may not have a shape that is different from the non-circular cross section of the elongate body. Referring to FIG. 15A, in a particular embodiment, the second non-circular cross section comprises a hexagon shape with rounded corners. The protrusion may be configured to be to provide a holding means for a surgeon or a maneuver tool so that the positioning of the spinal rod in the rod channel can be adjusted.

In some embodiments, the spinal rods disclosed herein can be used for different functions during a spinal procedure. For example, the spinal rods herein can be used as a working rod or a final locking rod.

In some embodiments, the cross section of the spinal rods disclosed herein are optimized to fit within the bone screw receiver 200 disclosed herein and has rounds on all corners to aid with manufacturing and to prevent stress concentrations. The spinal rod may resist torsion within the receiver of the pedicle screw. The spinal rods with a non-circular cross section may provide resistance to torsion that is greater than that of a spinal rod of circular cross section that fits into spinal rod channel of the bone screw receiver. The shape and/or size of the cross section may help the rod to self-center in the load ring of the receiver when tightened down due to the wedge/V-shape and flat on top. The rod may have a better lockdown interface with a set screw because now it has a flat to flat connection that maximizes the surface area in contact to increase rod resistance to slippage.

In some embodiments, these spinal rods disclosed herein can be advantageously used as the contra-lateral rods following a rod roll technique, where straightness of the rod in the sagittal plane needs to be maintained. In some embodiments, the spinal rods may be bent to what the corrected spine should be so that after an initial rod roll technique using a circular rod, one rod can be placed on the contra-lateral side and then locked down, then the other can replace the lateral circular rod. In some embodiments, the spinal rods herein can be used as an alternative to a global distractor where instead of dropping in satellite rods, this is a hop-scot technique, where a non-implantable rod can be used for the correction then drop in the opposing rod to lock down correction and then replace the working rod with a final locking rod. The working rod in this technique could be reused just for rigidity in correction but replaced with smaller profile rods out of titanium for a less rigid final construct to help prevent screw pullout.

In some embodiments, the spinal rods with a non-circular cross section herein can be advantageously used as deformity rods in order to increase strength and rigidity relative to circular cross section rods but with an overall lower profile of rods with equivalent polar moment of inertia. These rods may have flat edge(s) on the lateral sides to aid with rotational stiffness and allow rotational control over the rod through alignment with the walls of the rod slot feature on the screw. The rod may have a flat edge on the posterior side to maximize or optimize surface contact with the set screw during lock down. The anterior portion of the rod may a wedge shape to self-center in the pedicle screw when being locked down and further drive lateral alignment with the tulip of the pedicle screw. In some embodiments, the spinal rods disclosed herein with non-circular cross section are configured to provide a contact surface that is greater than that provided by a traditional spinal rod, either on the proximal side or distal side of the rod.

Figure 15D:
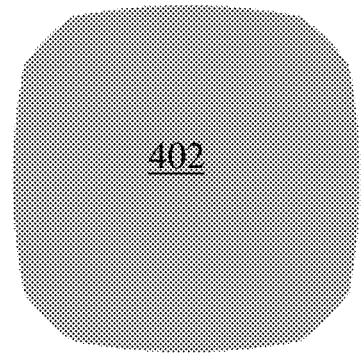
Figure 15E:
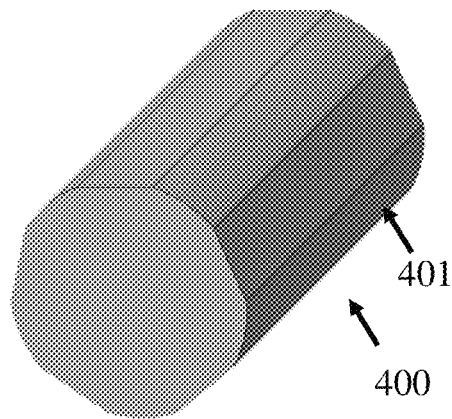

Continuing referring to FIGS. 15A-15B, the cross section are shaped like a shield, horizontally flat on the top, vertically flat on the sides with a rounded V-shape on the bottom. Referring to FIGS. 15C-15D, in one embodiment, the non-circular cross section comprises a curved top edge, two curved side edges, and a curved bottom edge. Referring to FIGS. 15E-15H, wherein the non-circular cross section comprises a flat top edge and a curved or flat bottom edge.

In some embodiments, the spinal rod may include a top surface, a bottom surface, or both that increases the contacting surface with the rod channel or a closure top. In some embodiments, the cross section of the spinal rod may be a polygon shape but the connecting point between two adjacent edges is rounded.

Figure 15F:
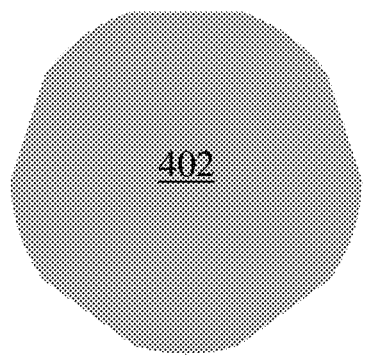
Figure 15G:
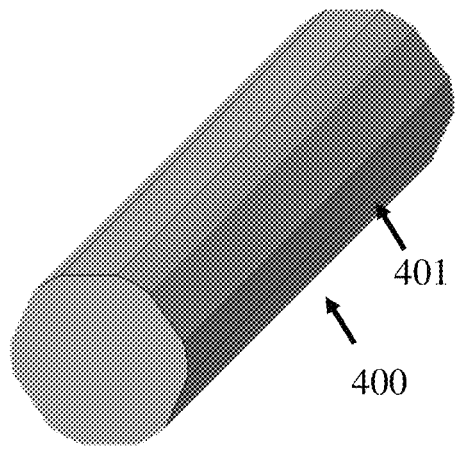
Figure 15H:
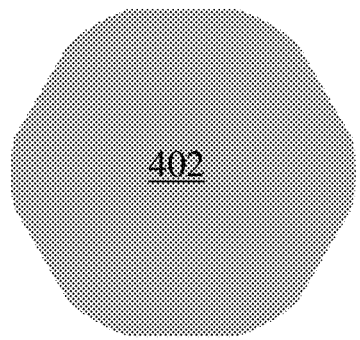
Figure 16A:
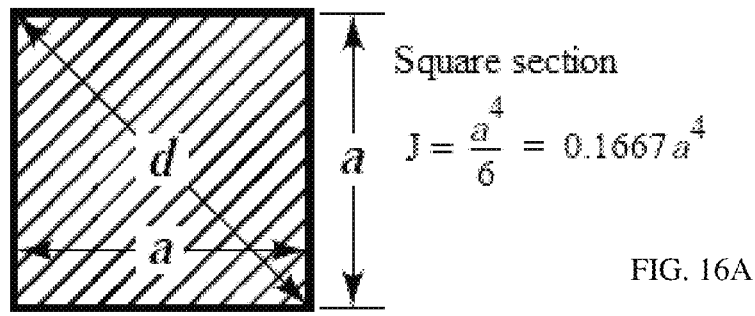
FIGS. 16A-16D show exemplary cross section of spinal rods with the corresponding calculation of polar moment of inertia for torsion of the spinal rods, in accordance with embodiments herein.
Figure 16B:
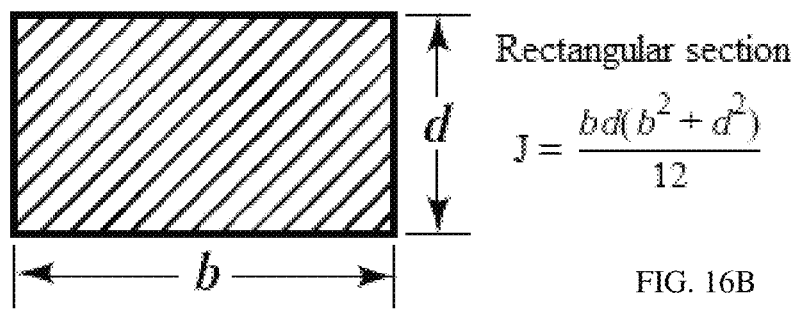
Figure 16C:
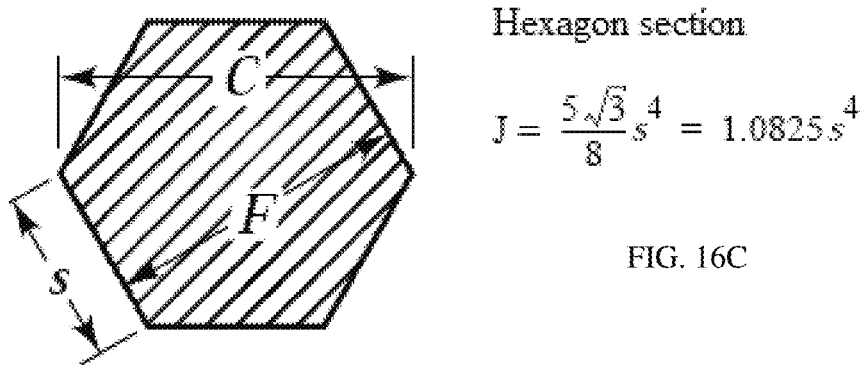
Figure 16D:
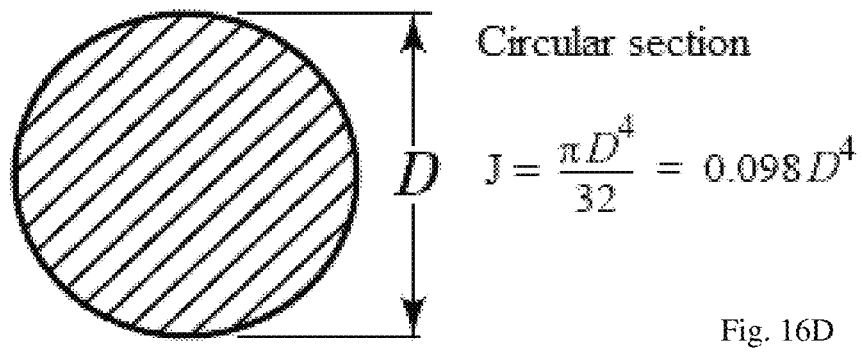

In some embodiments, the non-circular cross section may comprise curved connection(s) or curved corner(s) between two adjacent edges. For example, between the curved top edge and either one of the two curved side edges, and/or between the curved bottom edge and either one of the two curved side edges. In some embodiments, one or more of the curved top edge, curved bottom edge, and two curved side edges are convex. In some embodiments, the spinal rods disclosed herein may include a cross section with 4 edges, as shown in FIGS. 15B and 15D. In some embodiments, the spinal rods herein may include a cross section with 6 edges with each pair of adjacent edges connected with a rounded corner, as shown in FIG. 15F. In some embodiments, the spinal rods herein may include a cross section with 12 edges and rounded corners, as shown in FIG. 15H.

In some embodiments, the spinal rods with non-circular cross section may be used to advantageously provide more strength than conventional fixation rod with a circular cross section without making a higher profile since this profile of the spinal rod may drive the overall height of the tulip or receiver. In some embodiments, the spinal rod may be more resistant to torsion and may create a more rigid engagement within the receiver of the pedicle screw than traditional spinal rods with circular cross section.

In some embodiments, the spinal rod herein includes an increased cross-sectional width than the traditional rods with circular cross section. This increased width may help eliminate the ability to roll the rod within a pedicle screw, resist torsion and allow greater axial rotation correction operatively. In some embodiments, the size and shape of the spinal rods disclosed herein may help maximize the connection between the rod and the receiver to make the combination as rigid as possible, maximize the polar moment of inertia relative to height, maximize the mating surface between the set screw and rod to increase lockdown strength and prevent slippage.

Moment of inertia, I, can be considered as stiffness relative to cross section. Referring to FIGS. 16A-16D, polar moment of inertia for torsion, J, with different cross sections can be calculated differently.

Iliac Screws

In some embodiments, disclosed herein are bone screws, e.g., iliac screws that do not require insertion of a rod to lock the shank relative to the receiver. Instead, the receiver or tulip may have a low profile and can lock to the shank via a lock screw or other closure tops. A strut or rod off the lateral side of the tulip allows for connection of a rod to rod connector or has a tulip/rod slot to connect directly to a spinal rod of the construct. In some embodiments, the bone screws herein can be either preassembled or modular. In some embodiments, the rods herein can be either a straight or angled rod as the strut or a tulip/rod slot.

The bone screws disclosed herein may be an alternative implant to the existing open or closed iliac screws which can be placed on the ilium, sacrum, or sacroiliac region and require either a sharp bend in the longitudinal rod to join with screws at superior levels or a secondary horizontal rod or offset tulip connector. The bone screws herein may be used in a streamlined offering to reduce the number of different connectors and overall bulk of the construct while making a more rigid construct by reducing the number of connection points/places to fail. The bone screws herein may be modular for ease of placement but can also be made as a preassembled variant.

Figure 17A:
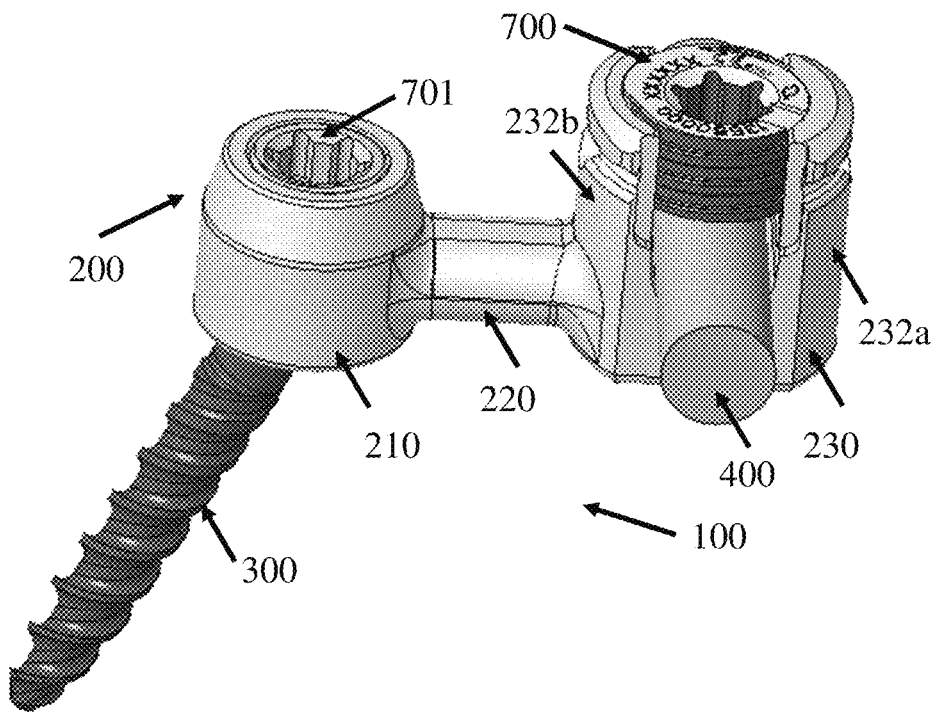
FIGS. 17A-17B show exemplary embodiments of the bone screws disclosed herein, in accordance with embodiments herein.
Figure 17B:
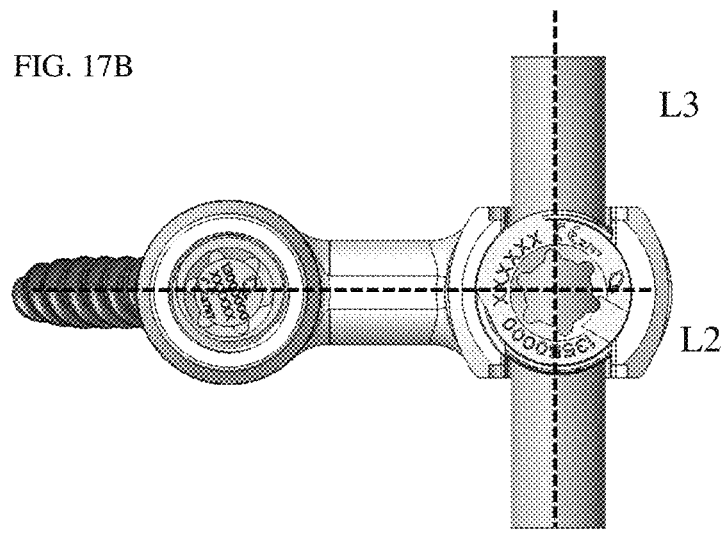
Figure 18:
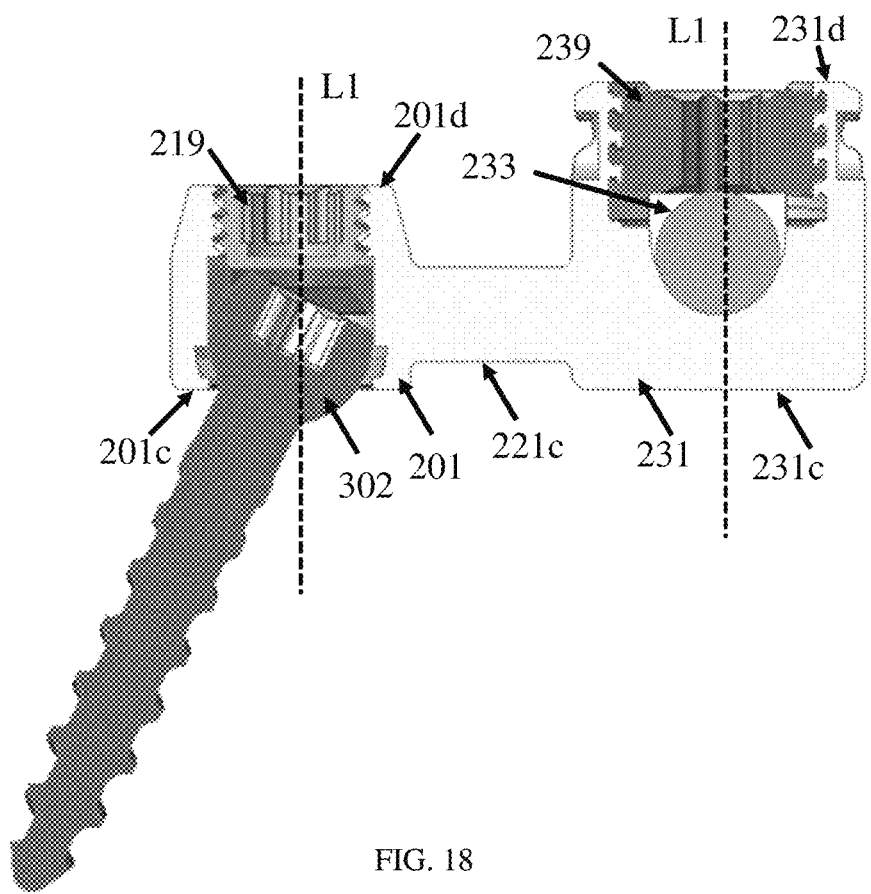
FIG. 18 shows a cross-sectional view of the bone screw in FIGS. 17A-17B, in accordance with embodiments herein.
Figure 20:
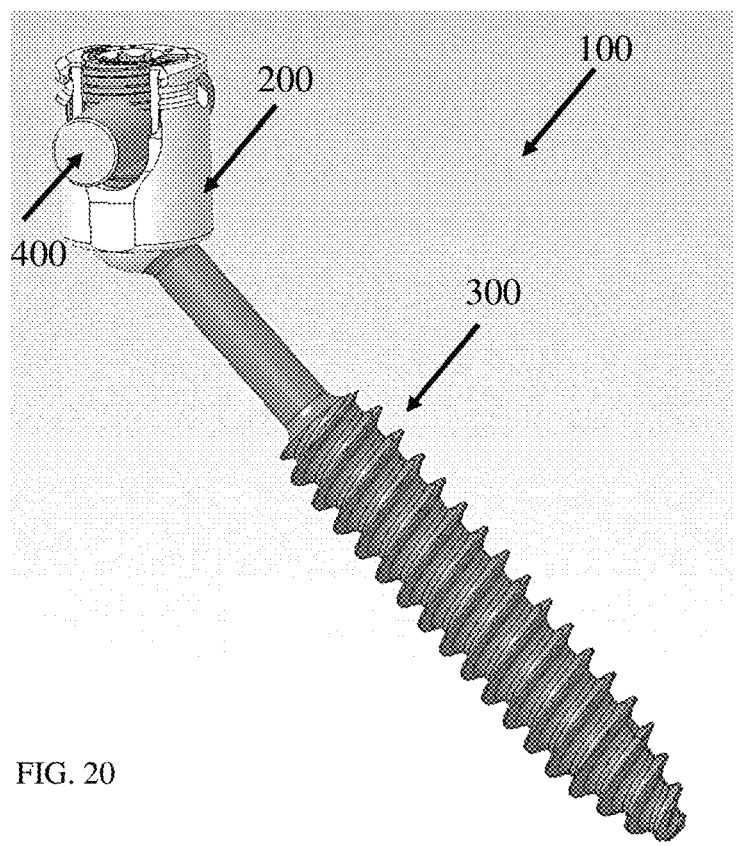
FIG. 20 shows an exemplary embodiment of the bone screws disclosed herein, in accordance with embodiments herein.

Referring to FIGS. 17A, 17B, and 18, in a particular embodiment, the bone screw 100 includes a bone screw shank 300 comprising a shank head 302, a dual-head receiver 200 having a first receiver 210 comprising a first base 201 having a cavity 209 therewithin, a first top having a top opening 219 to receive a locking element 701 therewithin thereby locking the shank head 302 within the cavity, without insertion of a spinal rod therewithin the receiver. The bone screw also includes a second receiver 230 comprising a second base 231 having a rod channel 233 defined between a pair of arms 232a, 232b; and a connection 220 between the first receiver 210 and the second receiver 230, the connection integral to the first and second receivers.

In some embodiments, a bottom surface 231c of the second base 231 is proximal or distal to a bottom surface 201c of the first base 201c. As shown in FIG. 18, the bottom surface of the second base 231c and a bottom surface of the first base 201c sit at an identical level along a proximal to distal direction, L1. In some embodiments, a top surface 201d of the first top is distal to a top surface 231d of the pair of arms of the second receiver 230, along L1 axis. In some embodiments, the first receiver 210 has a lower profile than the second receiver 230 along a proximal to distal direction, L1.

Continue to refer to FIGS. 17A, 17B, and 18, in this embodiment, the connection 220 between the first receiver and the second receiver extends along an axis that is substantially perpendicular to the longitudinal axis of the second receiver, L1. The L2 axis can also be substantially perpendicular to the L3 axis in which the spinal rod channel 233 is extending. The connection between the first receiver and the second receiver may extend laterally from an outer surface of one arm 231b of the pair of arms, along L2. On the opposite side, the connection between the first receiver and the second receiver may extend laterally from an outer surface of the first top, the first base 201, or both of the first receiver 210. A bottom surface of the connection 221c between the first receiver and the second receiver is proximal to a bottom surface of the first base 201c and/or a bottom surface of the second base 231c. The connector 220 is narrower than the first receiver and/or the second receiver in a direction L3, which is perpendicular to L1 and L2 axes as can be seen in FIGS. 17B and 18.

In some embodiments, the connection 220 may be integral to or fixed to both receivers. In some embodiments, the connection 220 may be integral to one of the first receiver 210 and the second receiver 230, but rotatable and/or translatable to the other one of the first and second receivers. As a result, one of the receiver, e.g., the second receiver 230 may be rotatable about the L1 or L3 axis. In some embodiments, the connection 220 may also enable translation of the second receiver relative to the first receiver to optimize the distance between the first and second rod channels.

In some embodiments, the connection 220 may be substantially straight, as shown in FIGS. 17A-17B. In some embodiments, the connection contains a curved portion, a bent portion, or a portion that is not substantially straight.

In some embodiments, the connection 220 may be extending along the L2 axis, as shown in FIG. 17B. In some embodiments, the connection 220 may be tilted away from the L2 axis for an acute angle, e.g., about 10-20 degrees. In some embodiments, the connection 220 may be tilted away from the L3 axis for an acute angle. In some embodiments, the direction along which the connection is extending may in the plane determined by L2 and L3 axes, so that the direction of extension of the lateral rod remains substantially perpendicular to the L1 axis. In some embodiments, the direction along which the connection is extending may be in the plane determined by L1 and L2 axes, thus it remains perpendicular to L3 axis instead. In some embodiments, the lateral rod may be tilted away for different acute angle(s) from any one, two, or three of the L1, L2, and L3 axes dependent on the need of the spinal applications.

In some embodiments, the top opening 219 of the first receiver is smaller in its longitudinal cross section than the top opening 239 of the second receiver. In some embodiments, a maximal dimension in a longitudinal cross section of the first base is smaller than a maximal dimension in the longitudinal cross section of the second base. In some embodiments second receiver is longer than the first receiver along a proximal to distal direction, L1.

In some embodiments, the bone screw 100 is a polyaxial screw. In some embodiments, the bone screw is an iliac screw. In some embodiments, the bone screw is configured to be inserted in the ilium, sacrum, or sacroiliac region and require either a sharp bend in the longitudinal rod to join with screws at superior levels or a secondary horizontal rod or offset tulip connector. An exemplary embodiment of the bone screw(s) inserted in a subject is shown in FIG. 19.

Lumbo-Sacral-Pelvic Bone Screws

The bone screws disclosed herein may be pedicle screw that can be bottom loaded and provide more than 40 degrees of polyaxial angulation. Such polyaxial angulation may even be achieved with an oversized shank head. The oversized shank head may include a maximal outer diameter that is greater than or equal to the outer diameter of a closure top that fits in the receiver. In some embodiments, the oversized head includes a diameter of greater than 8.5 mm. In some embodiments, the oversized head includes a diameter of greater than 9 mm or 9.5 mm. In some embodiments, the oversized head includes a diameter of greater than 9.8 mm or 9.9 mm. The receiver may be a modified version of existing pedicle screws which may retain some or even all of the proximal engagement features for instrument compatibility but may have a unique distal geometry. The screw can be assembled uniquely in that the load ring may be bottom loaded and may be twisted and pushed proximally into the tulip to allow the shank head to be bottom loaded with enough space for a clip ring or a lock ring to be assembled below the shank head. Once the clip ring is assembled the shank and load ring may be forced distally and then the load ring is rotated into placed to lock the bone screw. This design may be intended for large diameter screws used in the iliac and sacrum where a marginal increase in tulip height can be tolerated for increased angulation.

Figure 22E:
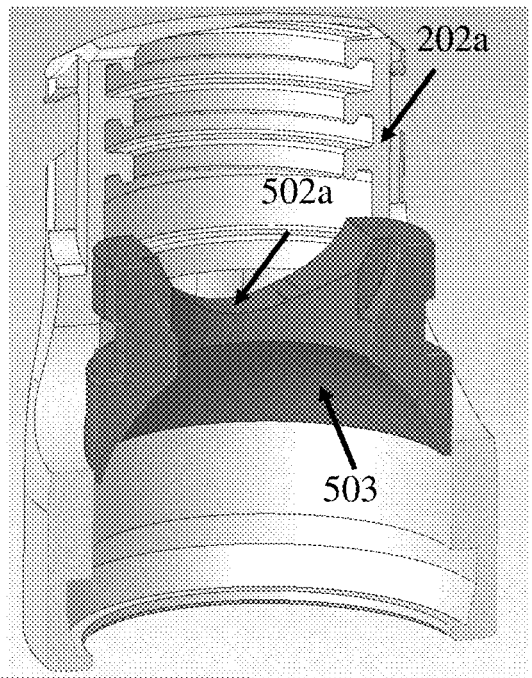

FIGS. 20, 21A-21B, 22A-22I, and 23A-23C show exemplary embodiments of such bone screws 100. The bone screws 100 may include a bone screw shank 300 comprising a shank head 302, a receiver 200 having a base 201 with a cavity 209 therewithin, the cavity configured to securely accept insertion of the shank head from a top of the receiver. The bone screw may include a pair of arms 202a, 202b extending upwardly from the base 201, and a rod channel 203 defined between the pair of arms. The bone screw may include a load ring 500 that can be bottom-loaded into the receiver prior to the insertion of the shank head 302, wherein the load ring comprises a pair of legs 501a, 501b connected by two concave surfaces 502a, 502b at its proximal side, as shown in FIGS. 22A-22B. The bone screw may also include a clip ring 600 that can be inserted into a groove 214 located in an inner surface at or near the bottom of the receiver in an open position when the load ring and the shank head are pushed proximal to a locking position. An exemplary embodiment of the locking position is shown in different views in FIGS. 23A (top view), 23B (cross section view cutting along F-F' in FIG. 23A), and 23C (cross section view rotated from FIG. 23B). An exemplary embodiment of the open position is shown in FIGS. 22F-22I. In the open position, each of the pair of legs 501a, 501b, faces an opening of the rod channel 203 and each of the concave surfaces 502a, 502b is aligned with one of the pair of arms. When in an open position, the top end of the legs 501a, 501b of the load ring is at a first location that is proximal to the second location in a locked position, as shown in FIGS. 22I and 23B.

In some embodiments, the bone screw is a polyaxial screw. The bone screw shank may rotate from a longitudinal axis of the receiver, L1, for about 0 degrees to about 40 degrees, as shown in FIG. 21B. In some embodiments, the rotation may be before a rod is secured in the rod channel 203. A maximal polyaxial angulation between the bone screw shank, L4, and a longitudinal axis of the receiver, L1, can be greater than 40 degrees. The load ring 500 may be pushed proximally and rotated away from the locked position during insertion of the shank head into the receiver, as shown in FIGS. 22A-22I.

Figure 23B:
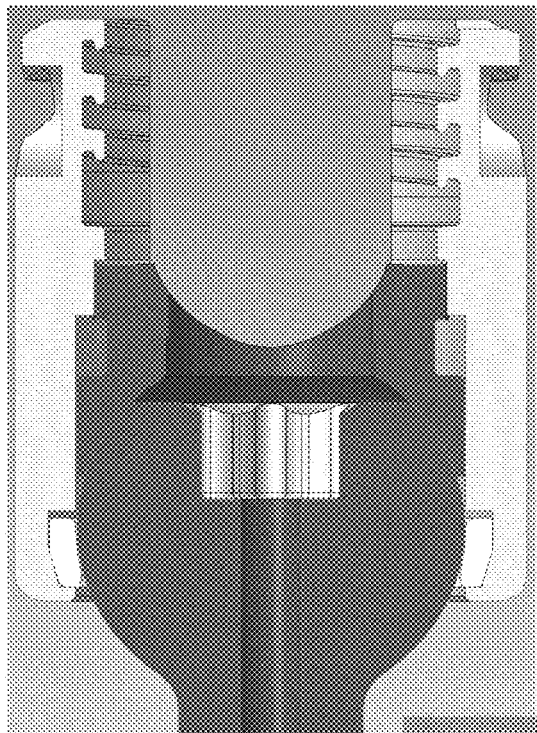
Figure 23C:
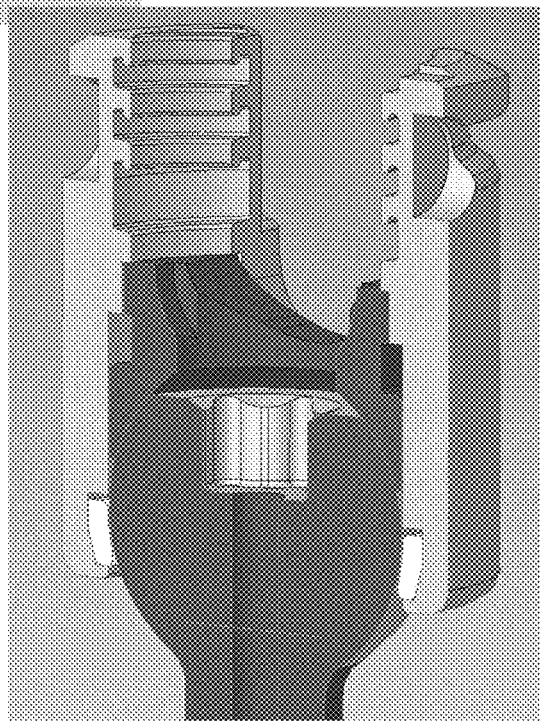

The load ring may be pushed distally and rotated to the lock position subsequent to insertion of the clip ring, as shown in FIGS. 23A-23C. In some cases, the load ring is rotated about a longitudinal axis of the receiver, L1, for about 90 degrees from the open position to the lock position. In some embodiments, the shank head is configured to be pushed distally from the open position to the lock position subsequent to insertion of the clip ring. The load ring may have an inner surface 503 and a distal portion thereof accommodates a shape of at least part of the shank head. The load ring may include a top opening allowing access to the shank head from a top of the receiver. The load ring can have an outer groove 504 between the pair of legs and a bottom portion thereof. The bottom portion of the load ring may be substantially cylindrical. The cross section at the bottom portion of the load ring can be greater than a cross section at the pair of legs thereof.

In some embodiments, the pair of arms comprises a protrusion 213 on an inner surface thereof, the protrusion 213 configured to prevent proximal translation of the load ring 500. As shown in FIG. 21B, at least part of the shank head may extend beyond the distal portion of the inner surface of the load ring when the bone screw shank is rotated from the longitudinal axis of the receiver.

In some cases, the bone screws 100 herein include an iliac screw or a sacral screw. The bone screw may comprise a tool engagement groove at an outer surface of the pair of arms at or near a top thereof.

Disclosed herein, in some embodiments, are methods for assembling a bone screw 100. The methods disclosed herein may include one or more method steps or operations disclosed herein but not necessarily in the order that the steps or operations disclosed herein.

In some embodiments, a method of assembly of a bone screw 100 includes providing a bone screw shank 300 comprising a shank head 301, providing a receiver 200 comprising a base 201 having a cavity 209 therewithin, the cavity configured to securely accept insertion of the shank head from a bottom of the receiver; a pair of arms 202a, 202b extending upwardly from the base; and a rod channel 203 defined between the pair of arms. The methods herein includes providing a load ring 500 configured to be bottom-loaded into the receiver prior to the insertion of the shank head, wherein the load ring comprises a pair of legs 501a, 501b connected by two concave surfaces 502a, 502b at its proximal side; and providing a clip ring 600 configured to be inserted into a groove 214 located in an inner surface at or near the bottom of the receiver thereby pushing the load ring and the shank head into an open position that is proximal to a locking position, wherein in the open position, each of the pair of legs 501a, 501b is at least partly facing an opening of the rod channel and each of the concave surfaces 502a, 502b are aligned with the pair of arms.

Figure 22F:
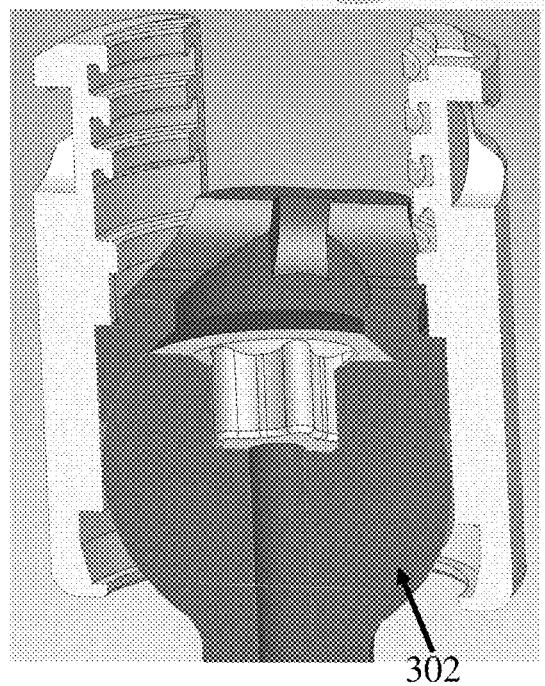

In some embodiments, the methods of assembly of a bone screw 100 include one or more of the disclosed method steps. The methods of assembly may include loading a load ring 500 from a bottom end of a receiver 200 of the bone screw through a cavity 209 thereof prior to the insertion of the shank head, as shown in FIGS. 22A-22D. Loading the load ring can include twisting the load ring about L1 axis so that each of two opposing concave surface 502a, 502b at a proximal surface of the load ring is aligned with an upwardly extending arm of the receiver and pushing the load ring proximally, as shown in FIGS. 22E-22F. The twisting may be of about 90 degrees. The load ring may be inserted with the pair of legs 501a, 501b facing the opening of the rod channel 203 as shown in FIGS. 22C-22D. FIG. 22C shows a cross section of the receiver along E-E' in FIG. 22D, and FIG. 22E shows a cross section of the receiver along C-C' in FIG. 22D. FIG. 22F shows the cross section along B-B' with the bone screw shank. Subsequent to the top-loading of the load ring, the load ring 500 and the shank head 302 may be pushed distally as shown in FIG. 22G to allow insertion of a clip ring 600 from the bottom. Subsequent to inserting the load ring, the methods may include inserting the shank head into the receiver from the bottom end thereof till access to a groove in an inner surface of the receiver at or near a distal end thereof is open. Afterwards, a clip ring 600 may be inserted into the groove 214 in the inner surface of the receiver, as shown in FIGS. 22G-22I. The methods then may include pushing the load ring and the shank head back distally; and twisting the load ring in to a locked position so that each of the two concave surfaces at the top surface of the load ring is aligned with an opening of the rod channel of the receiver, wherein the load ring and the shank head is locked from distal movement, as shown in FIGS. 23A-23C.

Uni-Directional Favored Angle Bone Screws

Disclosed herein, in some embodiments, are bone screws with the tulip or receiver custom designed around the shank. For instances, the shank neck geometry can be specifically designed such that the tulip or receiver has a channel to allow the shank to move directionally within the tulip as well as to control medial to lateral and caudal to cranial angulation (e.g., along L3 axis). The tulip or receiver may include a spherical pocket to match the shank head and may have threaded reliefs to allow the bone screw shank to be top-loaded into the tulip or receiver with threading on larger diameter screws, e.g., a diameter of about 8 mm. The load ring may have a spherical pocket and collet style fingers that are undersized to impart a frictional fit on the shank head once assembled. The load ring also may have material relieved to aid in the favored direction angulation of the screw shank. Once the rod is placed and locked down, the bone screw, the spinal rod, and the shank relative to the receiver can be locked. With or without a rod placed in the rod channel and with or without a lock screw placed in the receiver, the bone screw disclosed herein may provide a hard stop for the rotation on the receiver. In some embodiments, the hard stop is where the longitudinal axis of the receiver and the longitudinal axis of the bone screw shank are coaxial. The hard stop provided by the bone screw disclosed herein may allow for derotation movements without the need to provisionally lock the bone screw, reduce a rod, or use an outer or inner lock screw to lock the shank relative to the receiver. In some embodiments, this design of the bone screw is simple in nature and requires less steps when used in a surgical procedure where both favored angle screws and provisionally locking screw requirements are needed. For example, in a neuromuscular scoliosis case, the bone screw may be placed, the receiver may be rotated or angled in the lateral direction to facilitate rod capture in the rod channel, then rotated back medially until the longitudinal axis of the receiver and the longitudinal axis of the shank are coaxially aligned, then the receiver may continue to rotate to the contra-lateral side for rotational correction.

FIGS. 24-32 show exemplary embodiments of the bone screws with a favored angle. The bone screws 100 may include a bone screw shank 300 comprising a shank head 302, a receiver 200 having a base 201 with a cavity 209 therewithin, the cavity configured to securely accept insertion of the shank head from a top or proximal end of the receiver; a pair of arms 202a, 202b extending upwardly from the base 201; and a rod channel 203 defined between the pair of arms, wherein the base comprises a cut-out 211a and a recess 211 formed in a bottom surface of the receiver, wherein the cut-out and the recess are shaped and sized to allow angulation in a range of about 0 degrees to about 60 degrees, for example, in a first lateral direction D1. In some embodiments, the angulation allowed is in a range of about 0 degrees to about 40 degrees. In some cases, the angulation allowed is in a range of about 0 degrees to about 45 degrees. In some cases, the angulation allowed is in a range of about 0 degrees to about 50 degrees. In some embodiments, the bone screw shank can spin or rotate about L4 axis when the shank is rotated about longitudinal axis of the receiver, L1.

Figure 29:
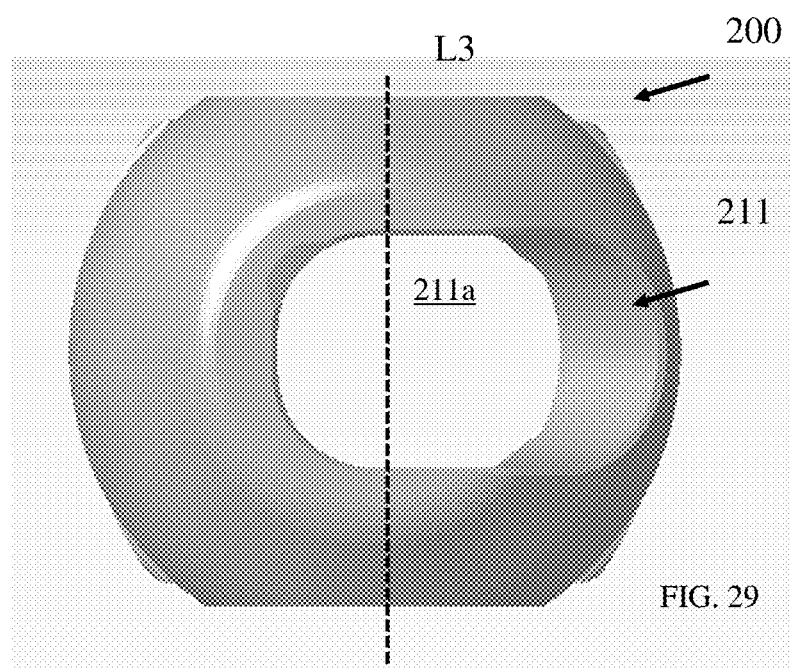
FIGS. 29-31 show exemplary embodiments of the receiver of the bone screws disclosed herein in different views, in accordance with embodiments herein.

The bone screw shank can be configured to rotate about L3 axis, which is shown in FIG. 29. The L3 axis may be perpendicular to the longitudinal axis of the receiver, L1, and the lateral axis, L2, of the receiver. In some cases, the rotation may be before a rod is secured in the rod channel. A maximal angulation, a, between a longitudinal axis of the bone screw shank, L1, and a longitudinal axis of the receiver, L4, can be in a range of about 0 degrees to about 65 degrees. The maximal angulation between a longitudinal axis of the bone screw shank and a longitudinal axis of the receiver is greater than about 45 degrees, 50 degrees, 55 degrees, or 60 degrees.

In some embodiments, the bone screw disclosed herein has about 0 to about 60 degrees in one direction along the medial-lateral axis (e.g., along D1 direction), about 0 degree in the opposite direction (e.g., along D2), and about 0 to 60 degrees the cranial-caudal direction (e.g., along L3 axis), or a combination thereof. In some embodiments, the bone screw disclosed herein has about 0 to about 60 degrees in one direction along the medial-lateral axis (e.g., along D1 direction), about 0 degrees in the opposite direction (e.g., along D2), and about −10 to 10 degrees the cranial-caudal direction (e.g., along L3 axis), or a combination thereof. In some embodiments, the bone screw disclosed herein has 55-60 degrees of angulation in the medial-lateral direction (e.g., along D1). In some embodiments, the bone screws disclosed herein has about −10 degrees to 10 degrees in the cranial-caudal direction.

In some embodiments, the distal geometry of the receiver may prevent angulation of greater than about 0 degrees in a second or opposite lateral direction D2, e.g., opposite the first lateral direction. In some embodiments, when a longitudinal axis of the receiver, L1, and a longitudinal axis of the bone screw shank, L4, are aligned, the bone screw is configured to allow derotation movement in the second or opposite lateral direction. In some embodiments, when a longitudinal axis of the receiver and a longitudinal axis of the bone screw shank are aligned, the receiver is configured to provide a hard stop to rotational movement of the bone screw shank relative to the receiver in the second lateral direction, D2, without using a rod, a closure top, or any other locking element external to the bone screw. The angulation of the bone screw shank may include movement in a medial to lateral direction (e.g., along D1 and/or D2 axis) and/or movement in a cranial to caudal direction (e.g., along L3 axis).

In some embodiments, a load ring 500 may be top-loaded into the receiver 200 subsequent to the insertion of the bone screw shank 300 via top-loading. The load ring may have a pair of legs 501a, 501b connected by two concave surfaces 502a, 502b at its proximal side, as shown in FIG. 32. In some embodiments, the load ring 500 comprises a top or proximal opening 505 allowing access to the shank head from a top of the receiver. The load ring may comprise an inner surface 503 and a distal portion of the inner surface accommodating a shape of at least part of the shank head. The load ring can include multiple fingers 504 at its distal end as shown in FIG. 32, and the fingers can be are configured to impart a frictional fit on the shank head. The load ring may comprise a distal recess 506 at its distal end, the distal recess aligned with the recess 211 of the receiver. The distal recess may aid angulation of the bone screw shank, e.g., in the first lateral direction, D1.

Figure 30:
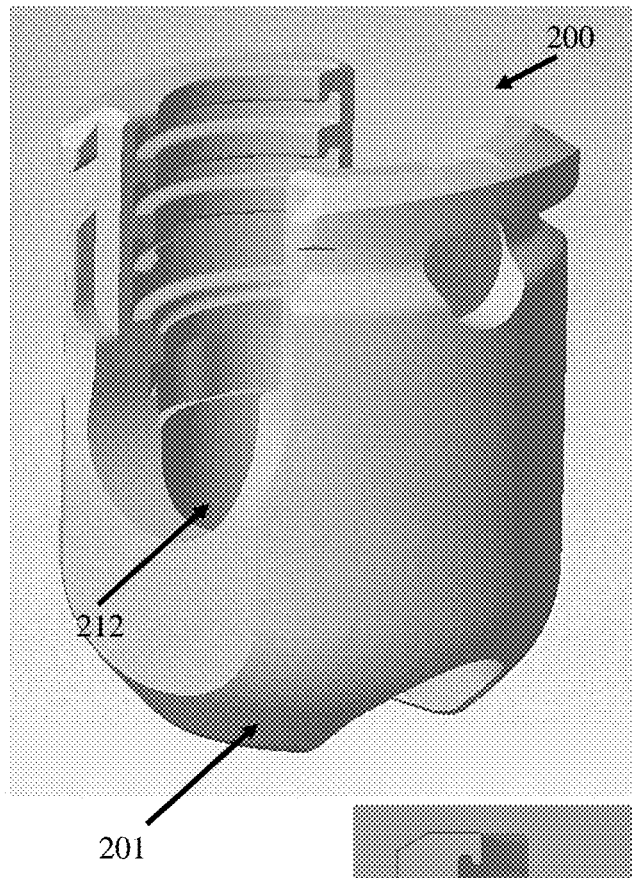
Figure 31:
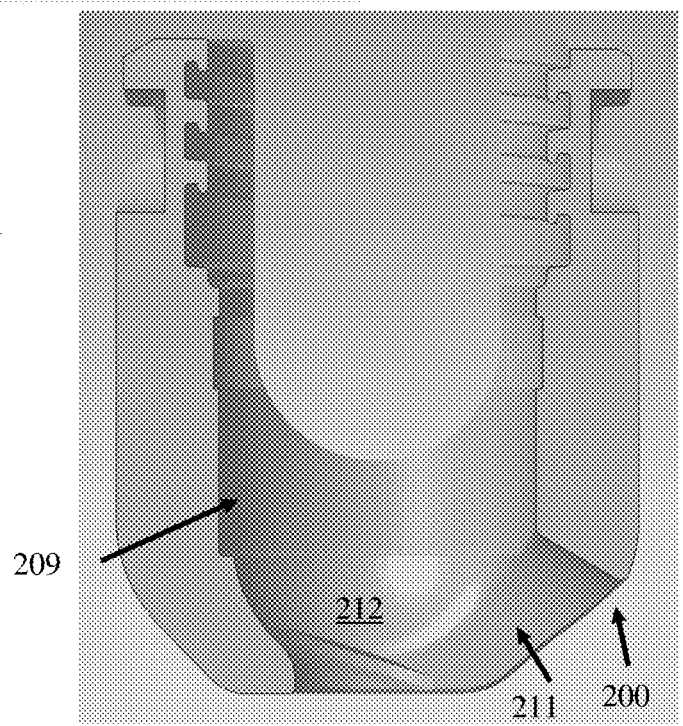

FIGS. 29-31 show different views of the receiver 200 disclosed herein. In some embodiments, the pair of arms 202a, 202b comprises a first protrusion 213 on an inner surface, the first protrusion configured to prevent proximal translation or movement of the load ring. A second protrusion 213b may be distal to the first protrusion and prevents distal translation or movement of the load ring. The first protrusion and the second protrusion may define a groove therebetween.

Figures 24, 25, 26:
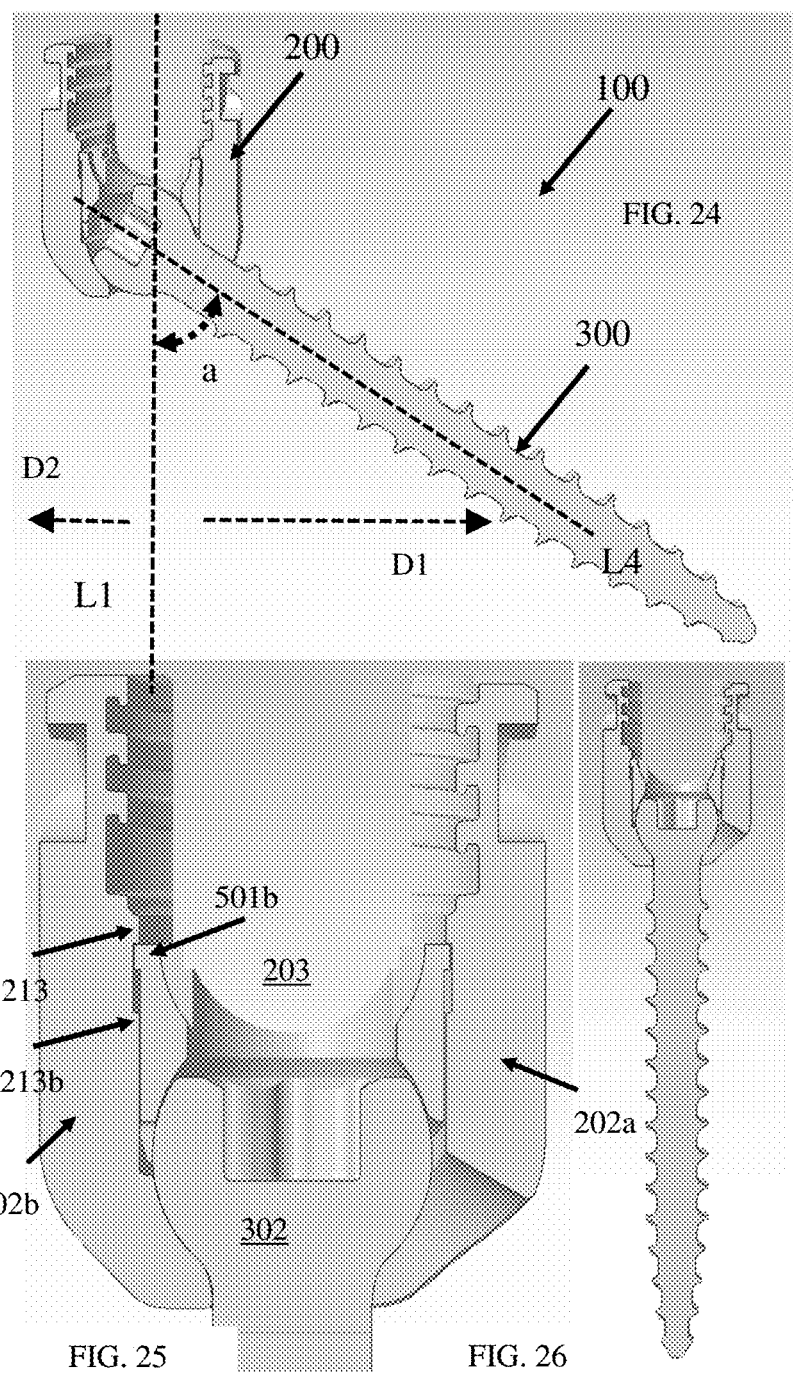
FIGS. 24-28 show exemplary embodiments of the bone screws disclosed herein; in this case, a bone screw that provides a hard stop and a tactile feedback when the longitudinal axis of the receiver is aligned with the longitudinal axis of the shank, in accordance with embodiments herein.
Figures 27, 28:
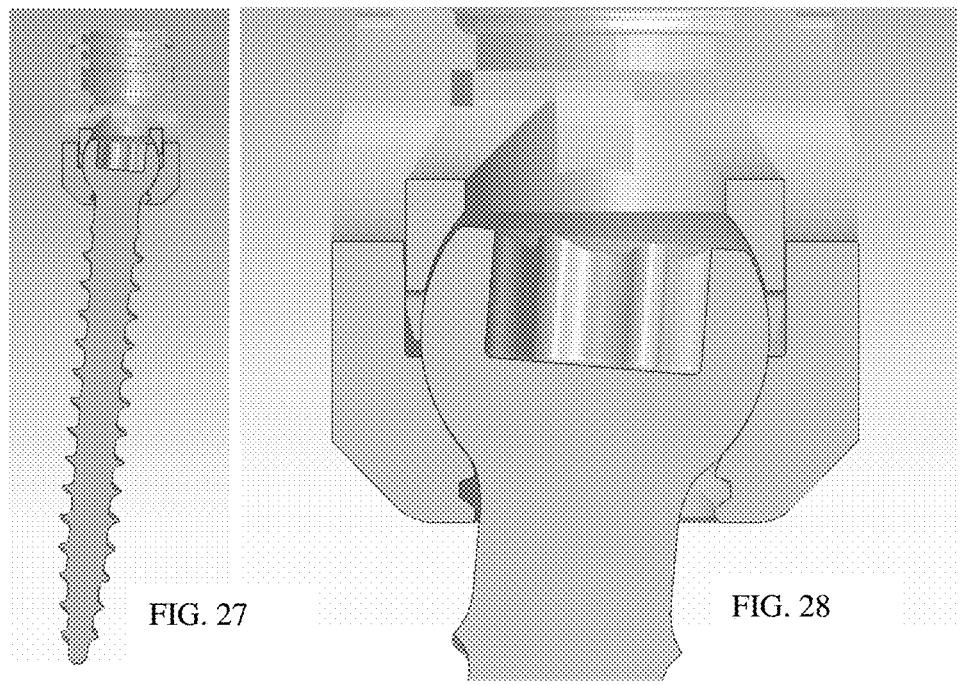

The receiver may comprise a pocket 212 in connection with the cavity at a distal portion thereof, the pocket 212 configured to receive the shank head and allow directional rotation therewithin. The pocket may comprise a pocket surface having at least part of a spherical surface that accommodates a spherical outer surface of the shank head 302. In some embodiments, at least part of the shank head extends beyond the distal portion of the inner surface of the load ring when the bone screw shank is rotated from the longitudinal axis of the receiver L1, e.g., as shown in FIG. 24.

The cavity 209 may comprise at least two bottom edges that are substantially flat, as shown in FIG. 29. Each of the at least two bottom edges are connected with a curved edge of the recess.

In some embodiments, the bone screw disclosed herein may be top loaded or bottom loaded during assembly. For top assembly, the bone screw shank 300 may be top-loaded into the receiver 200. Subsequently, the load ring 500 may be inserted from the top opening of the receiver.

In some embodiments, the shank head may comprise a head diameter or a maximal dimension in a range from about 4.0 mm to about 8.0 mm. The bone screw shank may comprise a length, including or excluding the shank head, from about 20 mm to about 120 mm.

In some embodiments, the bone screw may include a diameter of about 4.0 mm to about 8.0 mm. In some embodiments, the bone screw may include a length from about 20 mm to about 120 mm. The bone screw may have about 0 degree to about 60 degree angulation. Such range of angulation may be in a single lateral plane. In some embodiments, such range of angulation may be in a single lateral plane. In some embodiments, the range of angulation may be provided in more than one directions including but not limited to the first lateral direction.

The bone screws disclosed herein may advantageously provide a hard stop at about 0 degree when the longitudinal axis of the receiver and the longitudinal axis of the bone screw shank are coaxially aligned. When coaxially aligned, the hard stop may allow derotation movements of the receiver in the direction opposite of the favored direction to aid for capture of rods prior to derotation.

In some embodiments, the bone screw receiver disclosed herein may be sized and shaped to include a different cut-out from that shown in FIG. 29 so that the bone screw shank 300 may rotate symmetrically in two opposite directions, e.g., D1 and D4. The bone screws 200 may be uniplanar bone screws that the screw shank 300 can rotate within a single plane, e.g., a plane determined by L1 and L3 axes and perpendicular to L2 axis.

Figure 6:
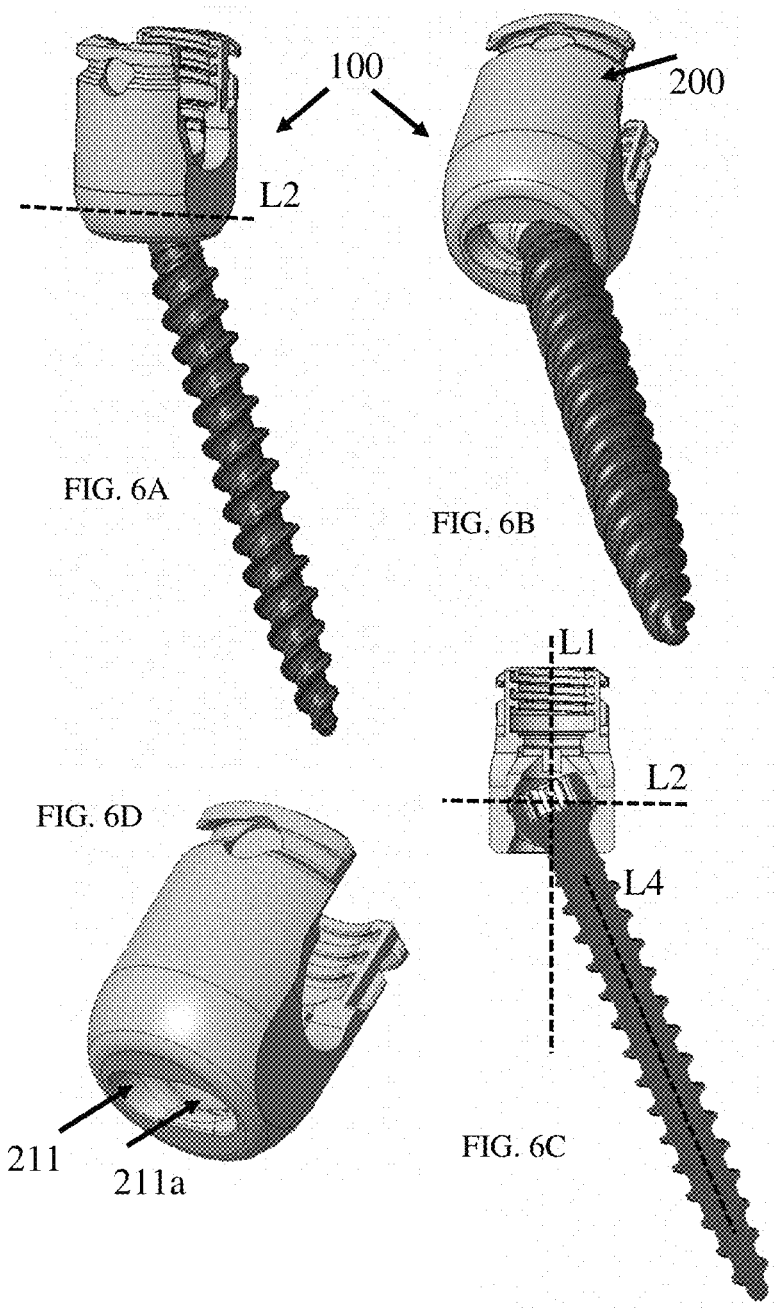
FIGS. 6A-6D show exemplary embodiments of the bone screws disclosed herein; in this case, a uniplanar bone screw that allow the bone screw shank to rotate symmetrically in two opposite directions, in accordance with embodiments herein.

Referring to FIGS. 6A-6D, in a particular embodiment, the base of the receiver 200 may include a cut-out 211a that is sized and/or shaped to allow the bone screw shank 300 to rotate in a single plane determined by L1 and L3 axes. FIGS. 6A-6B are perspective views of the bone screw 100, FIG. 6C shows a cross-sectional view of the bone screw, and FIG. 6D shows a perspective view of the receiver 200 with the cut-out 211a at a distal end thereof. The cut-out 211a may include two curved edges symmetrically located at two opposite ends and each connected to the same two substantially flat edges. The receiver may include two recesses 211 that each works with the cut-out to facilitate angulation of the screw shank about L2 axis. The screw shank may also be allowed to rotate about a longitudinal axis of the screw shank, L4, when the shank is rotated by an angle away from L1 axis. In some embodiments, the size and/or shape of the cut-out 211a, the recess(es) 211, or both may be customized to control angulation of the bone screw shank from L1 axis.

In some embodiments, the angulation from L1 axis may be in the range of about 0 degrees to about 60 degrees. The maximal angulation allowed from L1 axis may be in the range of about 30 degrees to about 60 degrees. The maximal angulation allowed from L1 axis may be in the range of about 35 degrees to about 50 degrees. The maximal angulation allowed from L1 axis may be in the range of about 40 degrees to about 50 degrees.

Polyaxial and Favored Angle Bone Screws

Disclosed herein, in some embodiments, are bone screws 100 having a bone screw shank 300 comprising a shank head 302, a receiver 200 comprising a base having a cavity therewithin, the cavity configured to securely accept insertion of the shank head from a top of the receiver, a pair of arms extending upwardly from the base, and a rod channel defined between the pair of arms, a compression element 500 configured to be top-loaded into the receiver subsequent to the insertion of the shank head. The compression element may comprise a pair of legs connected by two concave surfaces at its proximal side, and a lock screw configured to be top-loaded into the receiver thereby locking the shank head relative to the receiver.

FIGS. 33A-33D shows exemplary embodiments of different bone screw shanks 300 compatible with the receiver 200 disclosed herein.

FIGS. 34A-34B show exemplary embodiment of top loading the bone screw shank 300 into the receiver 200 in cross sectional views.

Figures 35A, 35B:
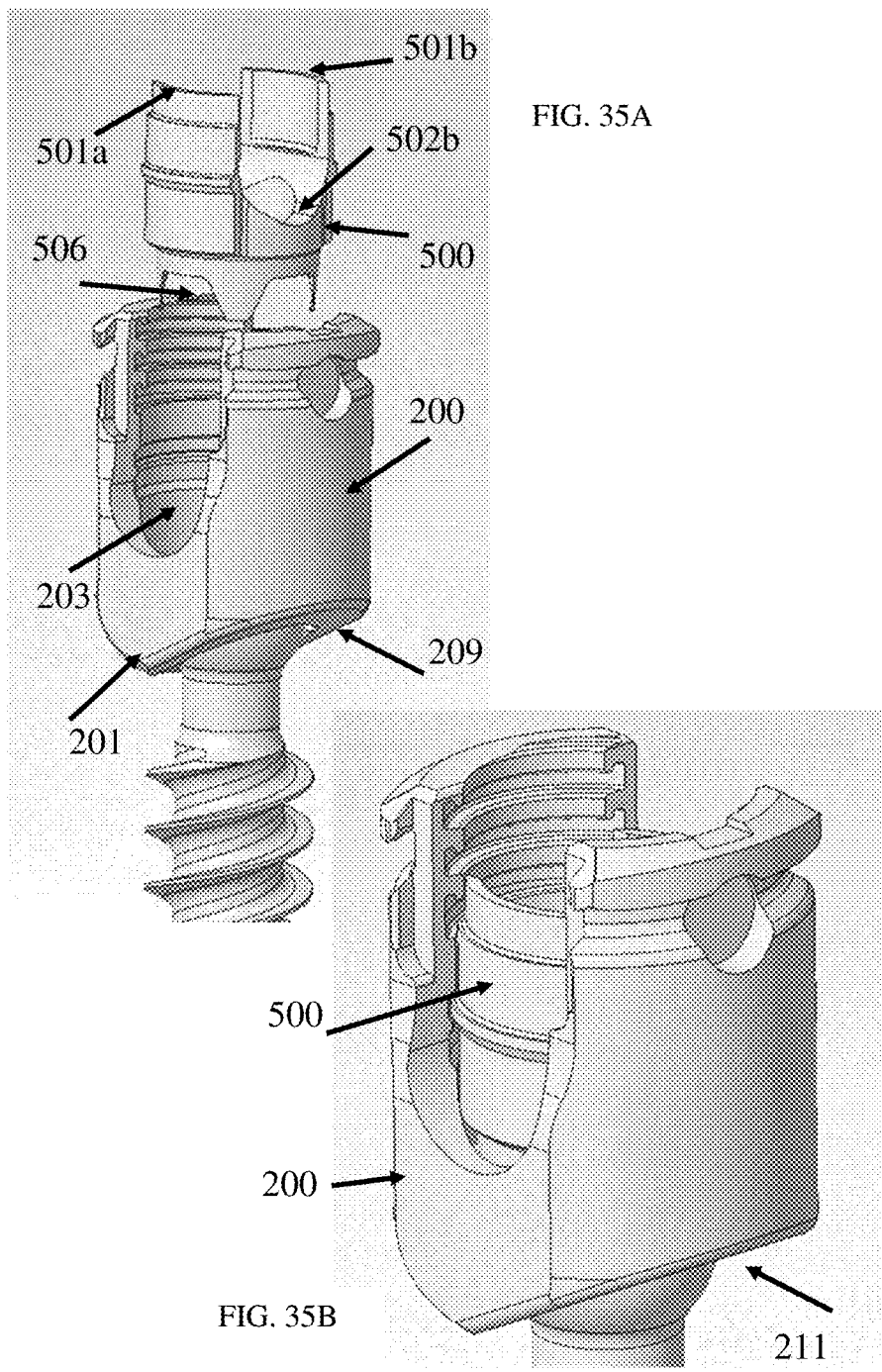
FIGS. 35A-35G show exemplary embodiments of the bone screws disclosed herein; in this case, the compression element during top-loading assembly of the bone screw, in accordance with embodiments herein.
Figure 35D:
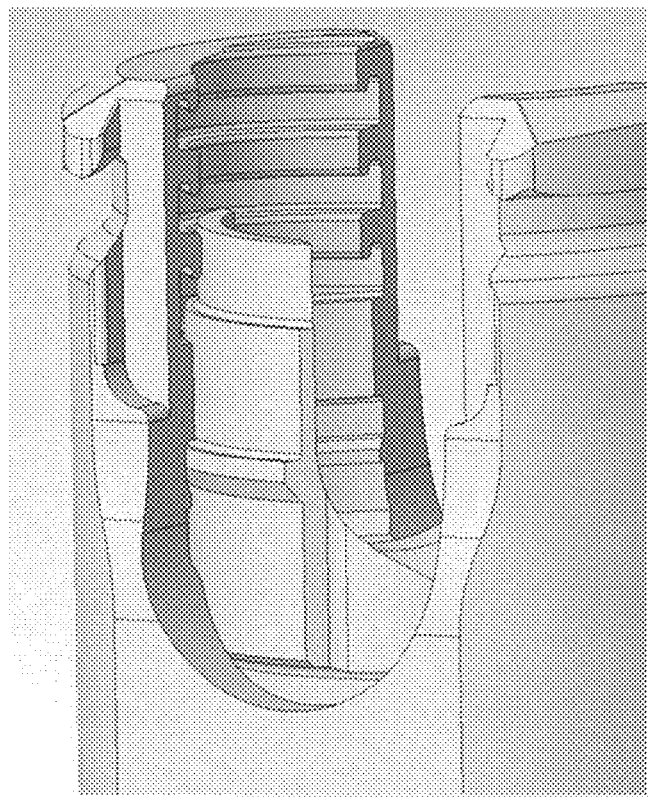
Figure 35C:
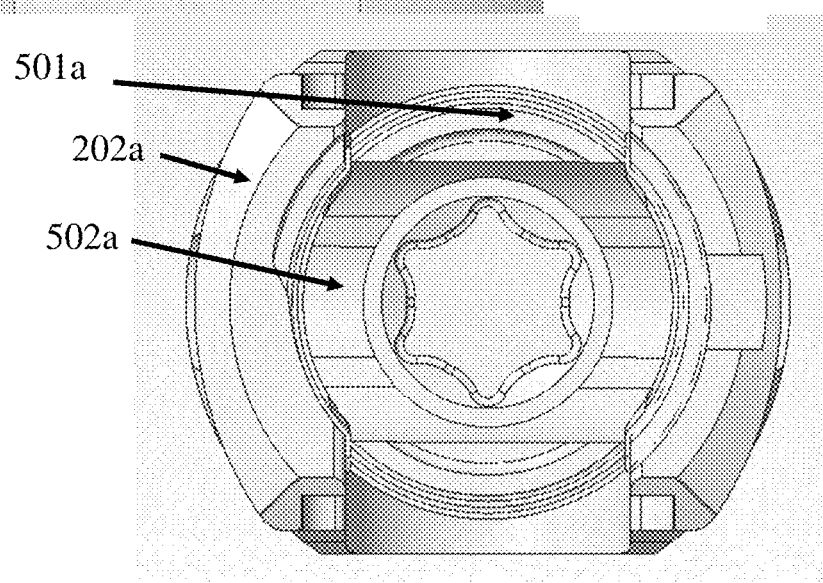
Figure 35E:
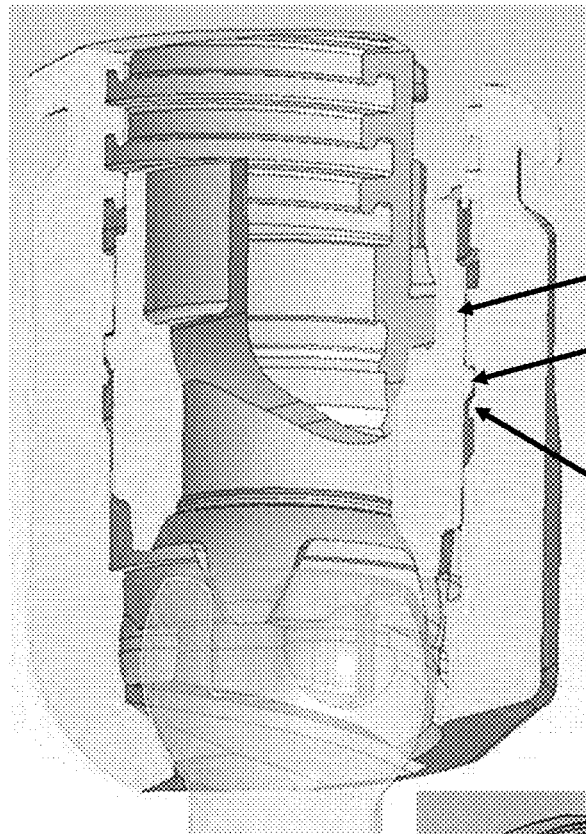
Figure 35F:
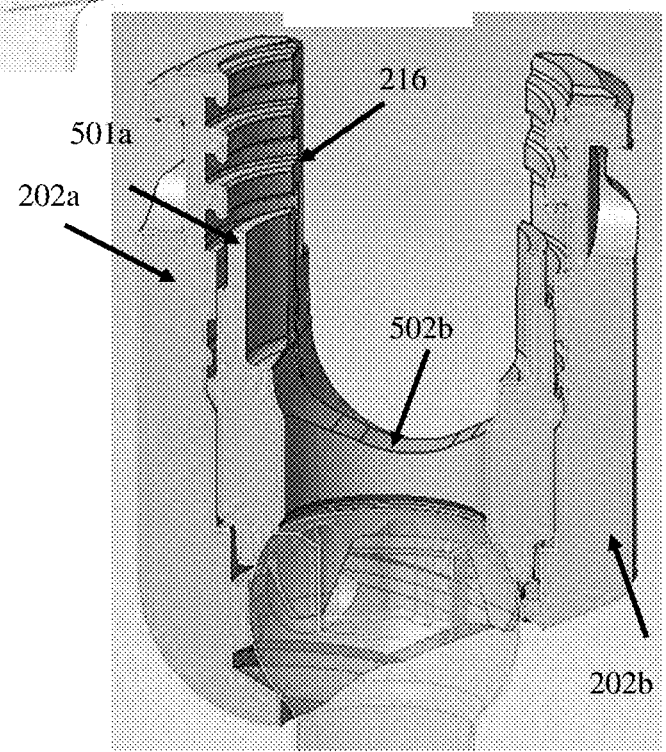
Figure 35G:
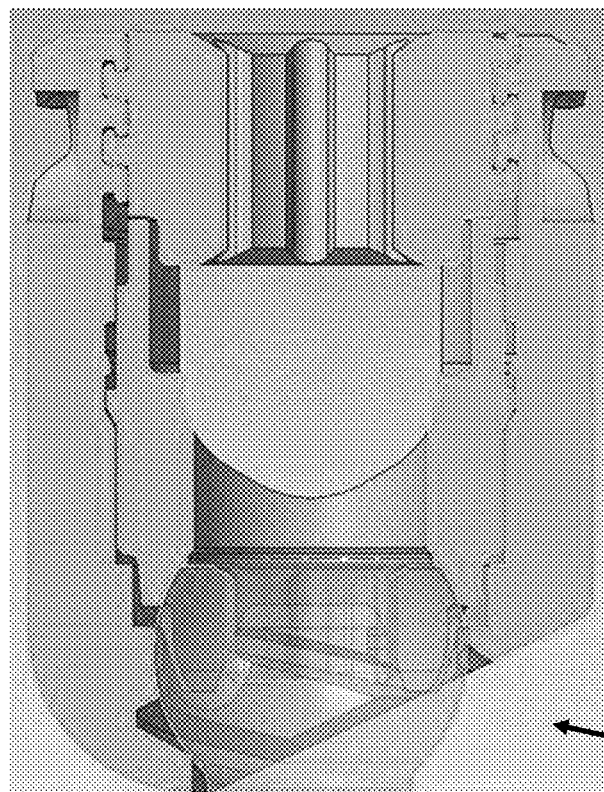
Figure 35H:
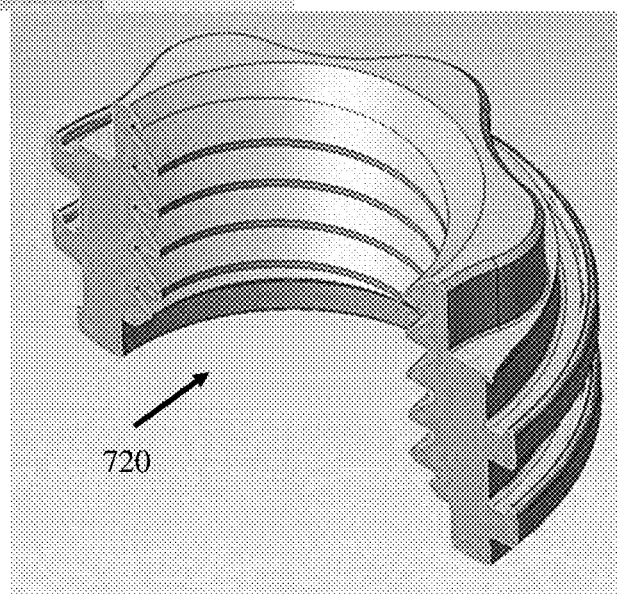
Figure 35I:
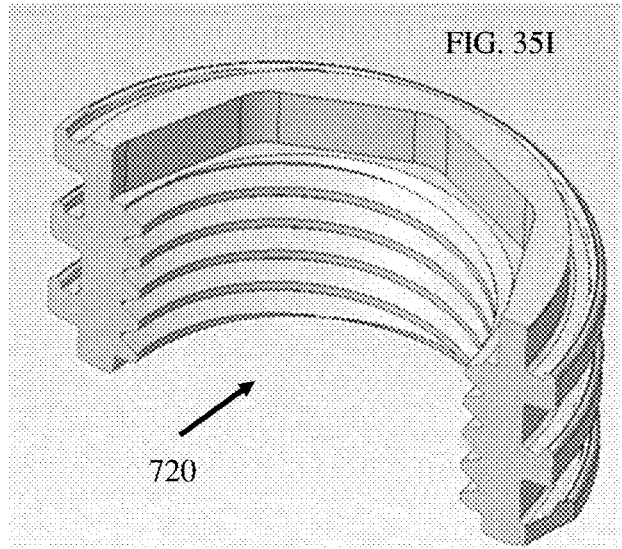
Figure 35J:
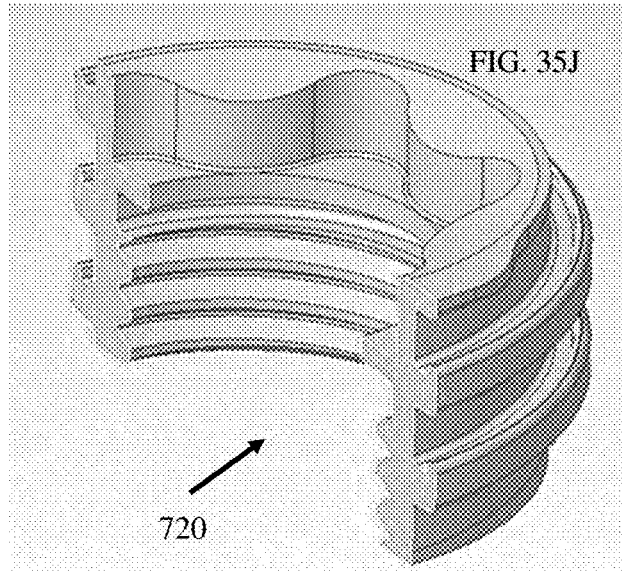

FIGS. 35A-35G show an exemplary embodiment of top loading the compression element 500 into the receiver 200 and rotating the compression element into position relative to the receiver, subsequent to top-loading the bone screw shank 300. In some embodiments, the compression element 500 can be loaded with each of the pair of legs 501a, 501b facing an opening of the rod channel 203 as shown in FIGS. 35A-35C. FIGS. 35A-35B are perspective views and FIG. 35C is a top view of the bone screw 100. Referring to FIGS. 35D-35G, subsequent to the top-loading of the compression element, the compression element 500 can be rotated for about 90 degrees so that each of the pair of legs 501a, 501b faces one of the pair of arms 202a 202b of the receiver, and pushed distally into a secured position relative to the receiver 200. In some embodiments, the compression element is configured to be rotated at a first location proximal to a second location where the compression element is in the secured position, as shown in FIGS. 35D and 35G. FIG. 35D shows a perspective view of the bone screw 100 and FIGS. 35E-35G are perspective views of the bone screw 100.

The compression element 500 can include a barb feature 515 on an outer surface of each of the pair of legs 501a, 501b. The barb feature can be configured to interact with a corresponding protrusion 215 on an inner surface of each of the pair of arms 202a, 202b thereby allowing distal insertion and preventing proximal movement of the compression element 500 relative to the receiver 200. The barb feature may include a ramping edge on its distal side, which interacts with a complementary proximal ramping edge on the receiver to allow distal movement of the compression element relative to the receiver. The compression element can have a through bore from a proximal end to a distal end thereof, the through bore configured to allow access of a drive tool to the bone screw shank. The compression element 500 may comprise an inner surface and a distal portion of the inner surface accommodating a shape of at least part of the shank head. The compression element may comprise a distal recess 506 at its distal end, the distal recess aligned with the recess of the receiver when the compression element is in a secured position. The distal recess of the compression element may be configured to aid angulation of the bone screw shank, e.g., in the first lateral direction. The angulation of the bone screw shank may include movement in a medial to lateral direction (e.g., along D1, D2, or both) and movement in a cranial to caudal direction (e.g., along L3 axis). At least part of the shank head may extend beyond the distal portion of the inner surface of the compression element when the bone screw shank is rotated from the longitudinal axis of the receiver.

The compression element 500 or the receiver 200 may comprise a coaxial indicator configured to provide a feedback when a longitudinal axis of the bone screw shank, L4, is aligned with a longitudinal axis of the receiver, L1. The feedback may be a tactile feedback. The feedback may be prevention of rotation in a second lateral direction. In some embodiments, the cavity is sized and shaped to prevent pulling off of the shank head from a bottom of the cavity.

The bone screws disclosed herein may include a lock screw 710. The lock screw 710 may be a dual lock screw as shown in FIGS. 35H-35L. The lock screw can have an outer element 720 that couples with an inner surface of the pair of arms 202a, 202b, and an inner element 730 that is configured to be inserted within the outer element and couples with the outer element, e.g. via threads. Exemplary embodiments of the outer element 720 are shown in FIGS. 35H-35L. The outer element 720 may comprise a helical flange threadform 721 that couples with a matching helical flange threadform 216 on the inner surface of the pair of arms. The outer element may include an outer drive feature 722 at or near a proximal end thereof, the outer drive feature configured to engage a driver tool. The outer drive feature 722 may be located on an outer surface, inner surface, or both of the outer element. Referring to FIGS. 35K-35L, in some embodiments, the outer drive feature may comprise a hexalobe at an inner surface of the outer element, the hexalobe extending distally but remaining proximal to a proximal end of the inner element. The outer element comprises a protrusion 723 located between the outer drive feature, e.g., the hexalobe, and a matching inner threading 724 configured to couple to the inner element. In some embodiments, the outer drive feature may include an external hexalobe as in FIG. 35H, an internal octagon as in FIG. 35I, or internal hexalobe driver feature as in FIG. 35J.

In some embodiments, the inner element comprises an inner drive feature 732, the inner drive feature configured to engage a second driver tool. The inner drive feature can include a second hexalobe at an inner surface of the inner element, the second hexalobe extending from at or near a distal end to at or near a proximal end of the inner element 730. The inner drive feature may include shapes other than hexalobe that may couple to a desired drive tool. The inner element may have an outer threading 734 that couples to an inner threading of the outer element 724. The dual lock screw can be configured to provisionally lock the bone screw head 302 relative to the receiver 200 prior to inserting a rod in the rod channel of the bone screw.

In some embodiments, the lock screw 710 is a single lock screw. The single lock screw can have a helical flange threadform 711 that couples with a matching helical flange threadform 216 on the inner surface of the pair of arms. The single lock screw may include a drive feature 712 extending from at or near a proximal end to at or near a distal end thereof. The drive feature may be configured to engage a driver tool. The single lock screw may lock the shank head 302 relative to the receiver 300 when a rod 400 is inserted in the rod channel 203 of the bone screw 100.

In some embodiments, the drive feature herein may be on an outer surface and/or inner surface to facilitate engagement with a drive tool without effecting coupling of the lock screw with the receiver. In some embodiments, the drive feature may be optimized in its shape and/or size to allow engagement with a specific drive tool.

The base 201 of the receiver comprises a recess 211 formed in a bottom surface of the base, wherein the cut-out 211a and the recess are shaped and sized to allow angulation in a range of about 0 degrees to about 40 degrees. In some embodiments, the base and the recess are sized and shaped to allow favors angulation in a single direction, e.g., in the first lateral direction, or in a single plane. In some embodiments, the base 201 and recess are shaped and sized to prevent angulation of greater than about 0 degrees in a second lateral direction opposite the first lateral direction. In some embodiments, the base and recess are shaped and sized to allow angulation in multiple directions. In some embodiments, the bone screw is polyaxial. FIGS. 37-38 show cross sectional views of different angulation of the shank head relative to the receiver.

The bone screw shank may be allowed to rotate about a direction in which the rod channel extends, e.g., L3 axis, of the receiver. A maximal angulation between the bone screw shank and a longitudinal axis of the receiver, L1, can be greater than about 50 degrees or about 55 degrees. A maximal angulation of the bone screw shank and a longitudinal axis of the receiver can be in a range of about 0 degrees to about 60 degrees. In some embodiments, the bone screw shank may be allowed to rotate about L1 axis of the receiver. In some embodiments, the bone screw shank is limited to rotate only in a lateral direction, e.g., in D1 direction as shown in FIG. 33B. In some embodiments, the bone screw shank is allowed to rotate along one or more directions other than D1, some or all of the directions forming an acute angle with the D1 direction. In some embodiments, the direction of rotation is determined by connecting the location of the shank right before the rotation, and the new location of the shank right after the rotation within the plane determined by L2 and L3 axes.

In some embodiments, the receiver may comprise a pocket in connection with the cavity at a distal portion thereof, the pocket configured to receive the shank head and allow directional or polyaxial rotation therewithin. The pocket can have a pocket surface having at least part of a spherical surface that accommodates a spherical outer surface of the shank head.

In some embodiments, wherein the shank head has a head diameter in a range from about 4.0 mm to about 8.0 mm. The bone screw shank may have a length from about 20 mm to about 120 mm. A diameter or a maximal dimension of a cross section of the dual lock screw is in a range of about 5.5 mm to 6.0 mm. A diameter or a maximal dimension of a cross section of the single lock screw can be in a range of about 5.5 mm to 6.0 mm. The rod channel may be configured to receive a spinal rod therewithin, wherein the spinal rod comprises a non-circular cross section.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bone screw comprising:
   a bone screw shank comprising a shank head;
   a dual-head receiver comprising:
      a first receiver comprising a first base having a cavity therewithin, the cavity configured to securely receive the shank head; a first pair of arms extending upwardly from the first base; a first rod channel defined between the first pair of arms;
      a second receiver comprising a second base having a second rod channel defined between a second pair of arms; and
      a connection between the first receiver and the second receiver,
      wherein the connection between the first receiver and the second receiver extends laterally from an outer surface of one of the first pair of arms, and extends laterally from an outer surface of the second base adjacent an opening of the second rod channel.

2. The bone screw of claim 1, wherein the connection is integral to one of the first receiver or the second receiver and is movable relative to the other one of the first receiver or the second receiver.

3. The bone screw of claim 1, wherein the first receiver comprises a longitudinal axis extending in a proximal to distal direction and the second receiver comprises a longitudinal axis extending in the proximal to distal direction, wherein the first rod channel extends in a first direction, and the second rod channel extends in a second direction substantially perpendicular to the first direction, or wherein the second rod channel extends in a second direction that is tilted by an angle from the first direction within a common plane that is perpendicular to the longitudinal axes of the first and second receivers in the proximal to distal direction.

4. The bone screw of claim 1, wherein the first receiver comprises a longitudinal axis extending in a proximal to distal direction, and wherein the connection between the first receiver and the second receiver extends substantially perpendicular to the longitudinal axis of the first receiver.

5. The bone screw of claim 1, wherein the first rod channel and the second rod channel comprise an identical size or shape.

6. The bone screw of claim 1, wherein the first receiver comprising a first tool engagement groove at an outer surface of the first pair of arms at or near a top surface thereof, and wherein a top edge of the connection between the first receiver and the second receiver is distal to the first tool engagement groove.

7. The bone screw of claim 1, wherein a bottom surface of the connection between the first receiver and the second receiver is proximal to a bottom surface of the first base.

8. The bone screw of claim 1, wherein the connector is narrower than the first receiver along a direction of extension of the first rod channel or the second rod channel.

9. The bone screw of claim 1, wherein second receiver is shorter than the first receiver along a proximal to distal direction.

10. The bone screw of claim 1, wherein the bone screw is a polyaxial screw.

11. The bone screw of claim 1, wherein an axis of the second rod channel is oriented parallel to a direction in which the connection extends from the outer surface of the second receiver.

12. The bone screw of claim 11, wherein an axis of the first rod channel is oriented perpendicular to the direction in which the connection extends from the outer surface of the first pair of arms.

13. The bone screw of claim 12, wherein the first receiver comprises a longitudinal axis extending in a proximal to distal direction, wherein the axis of the first rod channel, the axis of the second rod channel, and the direction in which the connection extends from the outer surface of the first pair of arms are approximately perpendicular to the longitudinal axis in the proximal to distal direction.

14. The bone screw of claim 1, wherein the connection extends laterally from the second base of the second receiver between the second pair of arms.

15. A bone screw assembly comprising:
a first bone screw comprising:
a first bone screw shank comprising a first shank head; a first dual-head receiver comprising: a first receiver comprising a first base having a first cavity therewithin, the first cavity configured to securely receive the first shank head; a first pair of arms extending upwardly from the first base; a first rod channel defined between the first pair of arms; a second receiver comprising a second base having a second rod channel defined between a second pair of arms; and a first connection between the first receiver and the second receiver, wherein the first receiver comprises a longitudinal axis extending in a proximal to distal direction and the second receiver comprises a longitudinal axis extending in the proximal to distal direction;
a second bone screw comprising:
a second bone screw shank comprising a second shank head; a second dual-head receiver comprising: a third receiver comprising a third base having a second cavity therewithin, the second cavity configured to securely receive the second shank head; a third pair of arms extending upwardly from the third base; a third rod channel defined between the third pair of arms; a fourth receiver comprising a fourth base having a fourth rod channel defined between a fourth pair of arms; and a second connection between the third receiver and the fourth receiver; and
a lateral rod securely received in the second rod channel and the fourth rod channel thereby securely connecting the first bone screw and the second bone screw,
wherein the first rod channel extends in a first direction, and the second rod channel extends in a second direction substantially perpendicular to the first direction within a common plane that is perpendicular to the longitudinal axes of the first and second receivers in the proximal to distal direction.

16. The bone screw assembly of claim 15, wherein the first connection comprises a substantially straight portion extending along an axis (L2) that is substantially perpendicular to a longitudinal axis of the first receiver, and wherein the connection comprises a curved portion connecting the straight portion and the second receiver.

17. A bone screw comprising:
a bone screw shank comprising a shank head;
a dual-head receiver comprising:
a first receiver comprising a first base having a cavity therewithin, the cavity configured to securely receive the shank head; a first pair of arms extending upwardly from the first base; a first rod channel defined between the first pair of arms;
a second receiver comprising a second base having a second rod channel defined between a second pair of arms,
wherein the first receiver comprises a longitudinal axis extending in a proximal to distal direction and the second receiver comprises a longitudinal axis extending in the proximal to distal direction; and
a connection between the first receiver and the second receiver,
wherein the connection between the first receiver and the second receiver extends laterally between an outer surface of one of the first pair of arms and an outer surface of one of the second pair of arms,
wherein the first rod channel and the second rod channel are either:
a) at an identical level along the proximal to distal direction, aligned substantially parallel with one another, and offset in each of two dimensions in a plane defined by the identical level, or
b) at two different levels along the proximal to distal direction and are aligned substantially perpendicularly with one another.

18. The bone screw of claim 17, wherein the first rod channel and the second rod channel are at the identical level along the proximal to distal direction, aligned substantially parallel with one another, and offset in each of two dimensions in the plane defined by the identical level, wherein the connection extends tangentially between the outer surface of one of the first pair of arms to the outer surface of one of the second pair of arms.

19. The bone screw of claim 17, wherein the first rod channel and the second rod channel are at two different levels along the proximal to distal direction and are aligned substantially perpendicularly with one another.

20. The bone screw of claim 19, wherein the connection comprises a substantially straight portion extending along an axis (L2) that is substantially perpendicular to a longitudinal axis of the first receiver, and wherein the connection comprises a curved portion connecting the straight portion and the second receiver,
wherein the connection has a first thickness in the substantially straight portion and a second, distinct thickness in the curved portion such that the first rod channel and the second rod channel are at distinct levels along an axis (L1) that is substantially perpendicular to L2.

* * * * *